(12) United States Patent
Davis et al.

(10) Patent No.: US 12,188,028 B1
(45) Date of Patent: Jan. 7, 2025

(54) METHODS FOR MAKING GENETIC REGULATORY ELEMENTS

(71) Applicant: MONSANTO TECHNOLOGY, LLC, St. Louis, MO (US)

(72) Inventors: Ian W. Davis, Durham, NC (US); Tedd D. Elich, Durham, NC (US)

(73) Assignee: MONSANTO TECHNOLOGY, LLC, Saint Louis, MO (US)

( * ) Notice: Subject to any disclaimer, the term of this patent is extended or adjusted under 35 U.S.C. 154(b) by 0 days.

(21) Appl. No.: 15/408,402

(22) Filed: Jan. 17, 2017

Related U.S. Application Data

(63) Continuation of application No. 13/599,255, filed on Aug. 30, 2012, now abandoned.

(60) Provisional application No. 61/535,117, filed on Sep. 15, 2011, provisional application No. 61/529,001, filed on Aug. 30, 2011.

(51) Int. Cl.
*C12N 15/82* (2006.01)

(52) U.S. Cl.
CPC ................................ *C12N 15/8202* (2013.01)

(58) Field of Classification Search
None
See application file for complete search history.

(56) References Cited

U.S. PATENT DOCUMENTS

| | | |
|---|---|---|
| 4,945,050 A | 7/1990 | Sanford et al. |
| 5,240,855 A | 8/1993 | Tomes |
| 5,316,931 A | 5/1994 | Donson et al. |
| 5,322,783 A | 6/1994 | Tomes et al. |
| 5,324,646 A | 6/1994 | Buising et al. |
| 5,380,831 A | 1/1995 | Adang et al. |
| 5,405,765 A | 4/1995 | Vasil et al. |
| 5,436,391 A | 7/1995 | Fujimoto et al. |
| 5,563,055 A | 10/1996 | Townsend et al. |
| 5,589,367 A | 12/1996 | Donson et al. |
| 5,605,793 A | 2/1997 | Stemmer |
| 5,736,369 A | 4/1998 | Bowen et al. |
| 5,837,458 A | 11/1998 | Minshull et al. |
| 5,866,785 A | 2/1999 | Donson et al. |
| 5,879,918 A | 3/1999 | Tomes et al. |
| 5,886,244 A | 3/1999 | Tomes et al. |
| 5,889,190 A | 3/1999 | Donson et al. |
| 5,889,191 A | 3/1999 | Turpen |
| 5,932,782 A | 8/1999 | Bidney et al. |
| 5,981,840 A | 11/1999 | Zhao et al. |
| 6,072,050 A | 6/2000 | Bowen et al. |
| 7,063,947 B2 | 2/2006 | Hahm |
| 7,645,919 B2 | 1/2010 | Anderson et al. |
| 2004/0175727 A1 | 9/2004 | Draghia-Akli et al. |
| 2013/0117883 A1* | 5/2013 | Elich ................. C12N 15/8216 800/278 |

FOREIGN PATENT DOCUMENTS

| | | |
|---|---|---|
| EP | 1877575 B1 | 9/2011 |
| EP | 2521439 | 11/2012 |
| WO | 1994000977 | 1/1994 |
| WO | 1995006722 | 3/1995 |
| WO | 0028058 A2 | 5/2000 |
| WO | 2001053476 A2 | 1/2002 |
| WO | 2006110852 A1 | 10/2006 |
| WO | 2011084370 A1 | 7/2011 |
| WO | 2012006426 A2 | 1/2012 |
| WO | 2012077020 A1 | 6/2012 |
| WO | 2012101191 A1 | 8/2012 |

OTHER PUBLICATIONS

Ross et al. Activation of the Oryza sativa non-symbiotic haemoglobin-2 promoter by the cytokinin-regulated transcription factor, ARR1. Journal of Experimental Biology. 2004. 55(403): 1721-1731.*
Rombauts et al. PlantCARE, a plant cis-acting regulatory element database. Nucleic Acids Research. 1999. 27(1): 295-296.*
Venter. Synthetic promoters: genetic control through cis engineering. TRENDS in Plant Science. 2007. 118-124.*
Bhullar et al. Strategies for Development of Functionally Equivalent Promoters with Minimum Sequence Homology for Transgene Expression in Plants: cis-Elements in a Novel DNA Context versus Domain Swapping. Plant Physiology. 2003. 132(2): 988-998.*
Scarmozzino et al. Comparison of Flavivirus Universal Primer Pairs and Development of a Rapid, Highly Sensitive Heminested Reverse Transcription-PCR Assay for Detection of Flaviviruses Targeted to a Conserved Region of the NS5 Gene Sequences. Journal of Clinical Microbiology. 2001. 39(5): 1922-1927.*
Damien. Gibbs sampling for Bayesian non-conjugate and hierachical models by using auxiliary variables. J. R. Statistics Society. 1999. 61(part 2): 331-344.*
Pilpel et al. Identifying regulatory networks by combinatorial analysis of promoter elements. Nature Genetics. 2001. 29: 153-159.*
Holt et al. ModuleFinder and CoReg: alternative toold for linkning gene expression modules with promoter sequences motifs to uncover gene regulation mechanisms in plants. Plant Methods. 2006. 2(8): 2-8.*
Luo et al. Promoter recognition based on the Interpolated Markov Chains optimized via simulated annealing and genetic algorithm. Pattern Recognition Letters. 2006. 27: 1031-1036.*
Callis et al. Introns increase gene expression in cultured maize cells. Genes & Development. 1987. 1: 1183-1200.*

(Continued)

*Primary Examiner* — Joseph Woitach
(74) *Attorney, Agent, or Firm* — Harness, Dickey & Pierce, P.L.C.

(57) ABSTRACT

The present invention provides methods, computer systems and computer-implemented products for making synthetic regulatory elements, and provides polynucleotide's, transgenic cells, and transgenic organisms (including viruses and viral vectors) produced by these methods. The invention thereby provides regulatory sequences to meet various gene expression objectives, including the ability to stack a plurality of heterologous genes for expression in a single cell, while avoiding gene silencing or reduced expression levels.

14 Claims, 2 Drawing Sheets

Specification includes a Sequence Listing.

(56) References Cited

OTHER PUBLICATIONS

Ohta et al. Construction and Expression in Tobacco of a β-Glucuronidase (GUS) Reporter Gene Containing an Intron Within the Coding Sequence. Plant and Cell Physiology. 1990. 31(6): 805-813.*
Rushton et al. Synthetic plant promoters containing defined regulatory elements provide novel insights into pathogen-and wound-inducible signaling. 2002. 14: 749-762.*
Deuschle et al. (1990) Science 248:480-483.
Gossen (1993) Ph.D. Thesis, University of Heidelberg.
Reines et al. (1993) PNAS 90:1917-1921.
Labow et al. (1990) Mol. Cell. Biol. 10:3343-3356.
Zambretti et al. (1992) PNAS 89:3952-3956.
Bairn et al. (1991) PNAS 88:5072-5076.
Wyborski et al. (1991) Nucleic Acids Res. 19:4647-4653.
Hillenand-Wissman (1989) Topics Mol. Struc. Biol. 10:143-162.
Degenkolb et al. (1991) Antimicrob. Agents Chemother. 35:1591-1595.
Kleinschmidt et al. (1988) Biochemistry 27:1094-1104.
Bonin (1993) Ph.D. Thesis, University of Heidelberg.
Gossen et al. (1992) PNAS 89:5547-5551.
Oliva et al. (1992) Antimicrob. Agents Chemother. 36:913-919.
Hlavka et al. (1985) Handbook of Experimental Pharmacology, vol. 78 ( Springer-Verlag, Berlin).
Gill et al. (1988) Nature 334:721-724.
An, G. et al. (1986) Plant Pysiol., 81:301-305.
Fry, J., et al. (1987) Plant Cell Rep. 6:321-325.
Block, M. (1988) Theor. Appl Genet. 76:767-774.
Hinchee, et al. (1990) Stadler. Genet. Symp. 203212.203-212.
Cousins, et al. (1991) Aust. J. Plant Physiol. 18:481-494.
Chee, P. P. and Slightom, J. L. (1992) Gene 118:255-260.
Christou, et al. (1992) Trends. Biotechnol. 10:239-246.
D'Halluin, et al. (1992) Bio/Technol. 10:309-314.
Dhir, et al. (1992) Plant Physiol. 99:81-88.
Casas et al. (1993) PNAS 90:11212-11216.
Christou, P. (1993) In Vitro Cell. Dev. Biol.-Plant; 29P:119-124.
Davies, et al. (1993) Plant Cell Rep. 12:180-183.
Dong, J. A. and Mchughen, A. (1993) Plant Sci. 91:139-148.
Franklin, C. I. and Trieu, T. N. (1993) Plant. Physiol. 102:167.
Golovkin, et al. (1993) Plant Sci. 90:41-52.
Guo Chin Sci. Bull. 38:2072-2078.
Asano, et al. (1994) Plant Cell Rep. 13.
Ayeres N. M. and Park, W. D. (1994) Crit. Rev. Plant. Sci. 13:219-239.
Barcelo, et al. (1994) Plant. J. 5:583-592.
Becker, et al. (1994) Plant. J. 5:299-307.
Borkowska et al. (1994) Acta. Physiol Plant. 16:225-230.
Christou, P. (1994) Agro. Food. Ind. Hi Tech. 5: 17-27.
Eapen et al. (1994) Plant Cell Rep. 13:582-586.
Hartman, et al. (1994) Bio-Technology 12: 919-923.
Ritala, et al. (1994) Plant. Mol. Biol. 24:317-325.
Wan, Y. C. and Lemaux, P. G. (1994) Plant Physiol. 104:3748.
Bilang et al. (1991) Gene 100: 247-250.
Scheid et al., (1991) Mol. Gen. Genet. 228: 104-112.
Guerche et al., (1987) Plant Science 52: 111-116.
Neuhause et al., (1987) Theor. Appl Genet. 75: 30-36.
Klein et al., (1987) Nature 327: 70-73.
Howell et al., (1980) Science 208:1265.
Horsch et al., (1985) Science 227: 1229-1231.
DeBlock et al., (1989) Plant Physiology 91: 694-701.
Crossway et al. (1986) Biotechniques 4:320-334.
Riggs et al. (1986) PNAS 83:5602-5606.
Paszkowski et al. (1984) EMBO J. 3:2717-2722.
Methods for Plant Molecular Biology (Weissbach and Weissbach, eds.) Academic Press, Inc.
Methods in Plant Molecular Biology (Schuler and Zielinski, eds.) Academic Press, Inc. (1989).
Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin).
McCabe et al. (1988) Biotechnology 6:923-926.
Weissinger et al. (1988) Ann. Rev. Genet. 22:421-477.
Sanford et al. (1987) Particulate Science and Technology 5:27-37.
Christou et al. (1988) Plant Physiol. 87:671-674.
Finer and McMullen (1991) In Vitro Cell Dev. Biol. 27P:175-182.
Singh et al. (1998) Theor. Appl. Genet. 96:319-324.
Datta et al. (1990) Biotechnology 8:736-740.
Klein et al. (1988) Biotechnology 6:559-563.
Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize).
Klein et al. (1988) Plant Physiol. 91:440-444.
Fromm et al. (1990) Biotechnology 8:833-839.
Hooykaas-Van Slogteren et al. (1984) Nature (London) 311:763-764.
Bytebier et al. (1987) PNAS 84:5345-5349.
De Wet et al. (1985) in The Experimental Manipulation of Ovule Tissues, ed. Chapman et al. (Longman, New York), pp. 197-209 (pollen).
Kaeppler et al. (1990) Plant Cell Reports 9:415-418.
Kaeppler et al. (1992) Theor. Appl. Genet. 84:560-566.
D'Halluin et al. (1992) Plant Cell 4:1495-1505.
Li et al. (1993) Plant Cell Reports 12:250-255.
Christou and Ford (1995) Annals of Botany 75:407-413.
Ishida et al. (1996) Nature Biotechnology 14:745-750.
McCormick et al. (1986) Plant Cell Reports 5:81-84.
Crossway et al. (1986) Mol Gen. Genet. 202:179-185.
Nomura et al. (1986) Plant Sci. 44:53-58.
Hepler et al. (1994) PNAS 91: 2176-2180.
Hush et al. (1994) The Journal of Cell Science 107:775-784.
Sheen, J. 2002. A transient expression assay using maize mesophyll protoplasts. http://genetics.mgh.harvard.edu/sheenweb/.
Clough and Bent (1998) Plant J. 16:735.
Brown et al. (1996) Plant Mol. Biol. 32:531-535.
Hirose et al. (2007) Plant Cell Physiol. 48:523-539.
Jain et al. (2007) Plant Physiology 143:1467-1483.
MSU/TIGR rice genome, version 6.1, http://rice.plantbiology.msu.edu/index.shtml.
Ouyang, S. et al. (2007) Nucleic Acids Res. 35:D883-D887.
Www.ncbi.nlm.nih.gov/genomes/GenomesHome.cgi.
Brady et al. (2007) Science 318:801-806.
TAIR *Arabidopsis* genome, version 9; http://www.Arabidopsis.org/.
Swarbreck et al. (2008) Nucleic Acids Res. 36:D1009-D1014.
Schmid et al. (2005) Nature Genetics 37:501-506.
Klein et al. (1988) PNAS 85:4305-4309.
Venter et al. Synthetic promoters: genetic control through cis engineering. TRENDS in Plant Science. 2007. 12(3): 118-124.
Damien et al. Gibbs sampling for Bayesian non-conjugate and hierarchial models by using auxiliary variables. Journal for Royal Statistical Society. 1999. 61(2): 331-344.
Holt et al. ModuleFinder and CoReg: alternative tools for linking gene expression modules with promoter sequences motifs to uncover gene regulation mechanisms in plants. Plant Methods. 2006. 2(8): 1-15.
Puente et al. (1996) EMBO J 15:3732-3743.
Rushton et al., (2002) Plant Cell 14:749-762.
Kinkhabwala and Guet (2008) PLoS One 3:e2030.
Gertz et al. (2009) Nature 457:215-218.
Edelman et al. (2000) PNAS 97:3038-3043.
Troukhan et al. (2009) OMICS 13(2):139-151.
Van Kerm (2003) "Adaptive kernel density estimation", 9th UK Stata Users meeting, Royal Statistical Society, London, May 19-20, 2003.
Linhad et al. Genome Research, 2008, 18:1180-1189.
Stemmer (1994) PNAS 91:10747-10751.
Stemmer (1994) Nature 370:389-391.
Crameri et al. (1997) Nature Biotech. 15:436-438.
Moore et al. (1997) J. Mol. Biol. 272:336-347.

(56) References Cited

OTHER PUBLICATIONS

Zhang et al. (1997) PNAS 94:4504-4509.
Crameri et al. (1998) Nature 391:288-291.
Sambrook et al. (1989) Molecular Cloning: A Laboratory Manual (2d ed., Cold Spring Harbor Laboratory Press, Plainview, New York).
Innis et al., eds. (1990) PCR Protocols: A Guide to Methods and Applications (Academic Press, New York).
Innis and Gelfand, eds. (1995) PCR Strategies (Academic Press, New York).
Innis and Gelfand, eds. (1999) PCR Methods Manual (Academic Press, New York).
Karlin and Altschul (1990) PNAS 87:2264.
Karlin and Altschul (1993) PNAS 90:5873-5877.
Altschul et al. (1990) J. Mol. Biol. 215:403.
Altschul et al. (1997) Nucleic Acids Res. 25:3389.
Myers and Miller (1988) CABIOS 4:11-17.
Edgar (2004) Nucleic Acids Res. 32(5):1792-1797.
Guerineau et al. (1991) Mol. Gen. Genet. 262:141-144.
Proudfoot (1991) Cell 64:671-674.
Sanfacon et al. (1991) Genes Dev. 5:141-149.
Mogen et al. (1990) Plant Cell 2:1261-1272.
Munroe et al. (1990) Gene 91:151-158.
Ballas et al. (1989) Nucleic Acids Res. 17:7891-7903.
Joshi et al. (1987) Nucleic Acids Res. 15:9627-9639.
Campbell and Gown (1990) Plant Physiol. 92:1-11.
Murray et al. (1989) Nucleic Acids Res. 17:477-498.
Elroy Stein et al. (1989) Pnas USA 86:6126-6130.
Gallie et al. (1995) Gene 165(2):233-238.
Allison et al. (1986) The nucleotide sequence of the coding region of tobacco etch virus genomic RNA: evidence for the synthesis of a single polyprotein. Virology 154: 9-20.
Macejak et al. (1991) Nature 353:90-94.
Jobling et al. (1987) Nature 325:622-625.
Gallie et al. (1989) in Molecular Biology of RNA, ed. Cech (Liss, New York), pp. 237-256.
Lommel et al. (1991) Virology 81:382-385.
Della-Cioppa et al. (1987) Plant Physiol. 84:965-968.
Su et al. (2004) Biotechnol Bioeng. 85:610-9.
Fetter et al. (2004) Plant Cell 16:215-28.
Bolte et al. (2004) J. Cell Science 117:943-54.
Kato et al. (2002) Plant Physiol. 129:913-42.
Yarranton (1992) Curr. Opin. Biotech. 3:506-511.
Christopherson et al. (1992) PNAS 89:6314-6318.
Yao et al. (1992) Cell 71:63-72.
Reznikoff (1992) Mol. Microbiol. 6:2419-2422.
Barkley et al. (1980) in The Operon, pp. 177-220.
Hu et al. (1987) Cell 48:555-566.
Brown et al. (1987) Cell 49:603-612.
Figge et al. (1988) Cell 52:713-722.
Deuschle et al. (1989) PNAS 86:5400-5404.
Fuerst et al. (1989) PNAS 86:2549-2553.

\* cited by examiner

SEQUENCE LISTING

<160> NUMBER OF SEQ ID NOS: 39

<210> SEQ ID NO 1
<211> LENGTH: 500
<212> TYPE: DNA
<213> ORGANISM: Artificial Sequence
<220> FEATURE:
<223> OTHER INFORMATION: SP1

<400> SEQUENCE: 1 aaataggggtt tttctccccc cacggcccac cacggcccac ctaggcccac cctaaaaaaa    60
ccctaggtgg gtgggcccat tttttttttt ttttttttt ttttaggtgg ggtgggccgt    120 gggggggaggt gggccgtggg cccatgaaaa aaaaaaaata gggttgggcc cacctaaaaa    180
aaaaacccta gggtgggccc aaaaaaaaaa aaaaaatgg gcccacccta tagggttttt    240 tttttttta agagtccgga cttccagaag aataataatc tcggcccacg tctaaaaaag    300
aaaccaccca tccgtccatg ggcccacctc agaccggccc accaagacaa agcccaccaa    360
cggtgggccg gcccattggt tcacagtcac ggcccacggc ccaccgcc caccgctcta    420 taaaccctat ataagaaacc ctccacctcc tcgccctctt ggtttcctcc ctcttccgcc    480
gcacacaccc acccagagat                                                 500

<210> SEQ ID NO 2

```
<211> LENGTH: 600
<212> TYPE: DNA
<213> ORGANISM: Artificial Sequence
<220> FEATURE:
<223> OTHER INFORMATION: SP2

<400> SEQUENCE: 2
gctagcgctt atggagcgtg atggactgaa agagacccct accacgtgtt gacgtaagca    60
atgacataaa accgatccta atctctccta cgaacgacag cggagagtac tgctgaaagc   120
tatgctttta ttttctttta tttttctcgt cagtggaata cacgttttgt cggtgtgtgt   180
ccttttccaa agaaagacgg aactgcctag acaacgtcg gctaccaaag cacaatgtaa    240
agtagacatg atgatcgacg acgtcatgca tgacgtttaa catgcattgt atgtgtccgt   300
cagtctataa ataggtcaag aacaaacatc gagaaaggc agaggcgaaa tacccatctg    360
cctatctctc aagaaataac tctctcttgt tcttcatcct ttctttcata gtttaaaaac   420
ctgaaattgg gcaagcccca taggcatttt ggtatcagag cgagtaagga caagtaggta   480
agtccctaaa atacttctat caataaaatt tctacgccaa gaagggtaag ttgtacgttt   540
atcctacacc cttgtgtttg taaccaggct tggtcaagtg cacaagggta tttgagtccc   600

<210> SEQ ID NO 3
<211> LENGTH: 500
<212> TYPE: DNA
<213> ORGANISM: Artificial Sequence
<220> FEATURE:
<223> OTHER INFORMATION: SP3

<400> SEQUENCE: 3
aacataactt gtatatttaa acataaagat aaaccttctt agagagaaca tatttaaatt    60
gtgttatcca ttacttttaa taaggaaata taatcttttc agtttgaatt gaaataact    120
ttatcaaaat ttatgacaaa tacaataaaa aaccaaaaca acaaaagaat tgtgtatatg   180
ttattgagaa acgattttta ttcactcgta catgattcat agaaaatttt aatttagtat   240
aaaaagtata aatataatat taatcaaata aattcttatg aaataaataa attcttcttc   300
aagggtaaat gaaaccttat gagtaaagtc tattctgcac ttaaaagaaa agagaattga   360
gtatttttg gaagcccatt tgggcccatt ttaaaatata ataagaaag cccaataatg     420
agaattaaaa accctagttt tcttcccctc ctatataaat cgacattttg ttcgttcctt   480
ctcttctctt ctcttcctct                                                500

<210> SEQ ID NO 4
<211> LENGTH: 500
<212> TYPE: DNA
<213> ORGANISM: Artificial Sequence
<220> FEATURE:
<223> OTHER INFORMATION: SP4

<400> SEQUENCE: 4
aaattgttga tagaatttca acataacat aacttaacat gaaatcttaa ttaattatca     60
gaaatacgat cactatcatc cgattttgtc ttttcgattt tattaatttt caactaaaac   120
atctcaacag ataaaacaaa accactttgt tgataatcca atattttaat tttattgaga   180
agatgatatg ataaagtata cagttatata caaaatgttt tctgcatatt tccaattttg   240
tcaaatgtca cttttaagtg tcaaacacta ataaaataaa ataaaataaa taatacttgg   300
attaatgagt aaaaaaatgg gcctaaacaa attatatcac taaaaagtaa tttagaaatt   360
cataattggc ccatttgacc gagttttta agctaaaatt ttaaaggccc aaaacccctta   420
```

```
ttagggtttc aacagaaacc tataaggaga ctctatataa accctctctt cgttcattag    480
ggtttctcct tctctgaaga                                                500

<210> SEQ ID NO 5
<211> LENGTH: 500
<212> TYPE: DNA
<213> ORGANISM: Artificial Sequence
<220> FEATURE:
<223> OTHER INFORMATION: SP5

<400> SEQUENCE: 5
acatttcggt tatctgggta ctacataaag attgccaagt ccattgattg aattgtgtgt    60 gttttatgg ctcacttata cgttgtcttt tttaacaaaa aatgttttca actaatttga    120
attttgttta caaacaaata caaataacca ttggtttctc aagaatcaat caagaattag    180
aaatgatatg atagatttct caataaaaga caaaattttc aattttttca gttttttgtaa   240 atctacagca tcatttgtga tatgtctatc aaattttgct taaataaata aatcctcaaa    300
tactttgaat gagtaaaaat gaaataatta ggcttacata gtaattaaat aggcttcaaa    360
aaggctaagg cccaaatttg ttaaattaag aattgaagtc caaaaaccta tgttaaaaca    420
atctaggtta gggtttcttc tctcctatat attctataaa ctaggtcatt ccattcgtca    480
aactcctctc ttgcaaactc                                                500

<210> SEQ ID NO 6
<211> LENGTH: 307
<212> TYPE: DNA
<213> ORGANISM: Artificial Sequence
<220> FEATURE:
<223> OTHER INFORMATION: SI1

<400> SEQUENCE: 6
caggtaagtt tctcttcttc agctcttctt cttcttcttg gatctcgatt ttcgtgtaca    60
tttcgtagtt cgatctgatt ttcgttgttg atctagattc ttgcgatttg ggttttgttg    120
tgttgataat tttcttagtg atctgataga ttgtttatag tgtttcagat tgtttagaaa    180
tcttctatga atttaggttt gatcggtttc ttgatcgatt tgatgatttc tatcaattga    240
ttagtggatc tgttttgttg tgatttctaa tattgatctg ttttgtttgc ttttttccga    300
tgcaggt                                                              307

<210> SEQ ID NO 7
<211> LENGTH: 307
<212> TYPE: DNA
<213> ORGANISM: Artificial Sequence
<220> FEATURE:
<223> OTHER INFORMATION: SI2

<400> SEQUENCE: 7
caggtaaaat ttctcctctc ctttcctctc tctcttctga ttctgatttc gttttcgctc    60
gatttggatc gtatttgtcg ttagttttta atcgtttgga ttcttggttg gtgtttgttt    120
gaattttcag ttgtagatct ttatagatct ctgtgtttta tgcatttaca tttaagattt    180
tagaaattgt tctagattgg tcttttttgtt tagattcatc tgatcaattc aatgattgat    240
tgtttgaatt gtgatttgat aagtttctac tttgatctgt atattgattt gtttgttcct    300
tgcaggt                                                              307

<210> SEQ ID NO 8
```

```
<211> LENGTH: 305
<212> TYPE: DNA
<213> ORGANISM: Artificial Sequence
<220> FEATURE:
<223> OTHER INFORMATION: SI3

<400> SEQUENCE: 8
caggtttaca tctttattcc ttgtgttctc ttatacttga atctttcatt ttggttttcg    60
atttgggttt ttcgatttgt ttagattaat ctgatttgag ctgtgtttat cattgtttcg   120
atctgtgata ttgaccaaat gatttgtgtt ttggttttct tagcttgtat tattattgat   180
tgaattcatt tcccattgat atttcgtttc tttttagcat tccaatctcc attgtttttt   240
ctgattatgc ttgtggatct ttacattttc aaaactttgt ggtctaatgt ttttttggtt   300
taggt                                                               305

<210> SEQ ID NO 9
<211> LENGTH: 310
<212> TYPE: DNA
<213> ORGANISM: Artificial Sequence
<220> FEATURE:
<223> OTHER INFORMATION: SI4

<400> SEQUENCE: 9
tcaaggtact actttctcat ccctctttca tactttttatt ctcttttgca ttttgatttg    60
gttttactct gagttttcta tctctcgatc tttgatttaa tctaattagg ttttttctag   120
atctagatct agatttgaaa atttaatagc tgttggtctt ccttgattttt gtttagctt   180 gagttttatg tatagaatgg tgtttctctt tgaatctgtt gcattctctt tatgaatctg   240
attaatcttt tgatttgtgt ttatcgtttc ttaaataaac ttgttgtttg gttttgagtt   300
tgcagagagg                                                          310

<210> SEQ ID NO 10
<211> LENGTH: 308
<212> TYPE: DNA
<213> ORGANISM: Artificial Sequence
<220> FEATURE:
<223> OTHER INFORMATION: SI5

<400> SEQUENCE: 10
caggtaaact tttcttctcc tcttctagat ctctcttctc tcgatttctg aattatttcg    60
taatttccga tctctgattt ttggtgttag attttgtttt ctgtgatcga tttgatttga   120
ttttcagttg tagagtaaag cttgtttgtt gtttgagggt tagatatatc agattatgat   180
ttccgatatt gttgtttctc tgtttcgttt tgattcatca tcttatctgt ggatttagat   240
tatttagtgt gattcgtatg tactctgatt gaatttgtgt gatctttgtg tttggttttt   300
gtgcaggt                                                            308

<210> SEQ ID NO 11
<211> LENGTH: 857
<212> TYPE: DNA
<213> ORGANISM: Arabidopsis thaliana

<400> SEQUENCE: 11
tgcgagtggg cgaattccgg agcactctga ttggctgaaa aaatagaaat agtagtgatg    60
ttgctcctcc tctcctcctc tattattaat tttcgtcgt tcttcttctg aaagttgtgt   120 ggttttttaga ggtcaccaaa aaaaatctat tttgagatac taaaaatatt tcgttttgca   180
ttttgttgtg cagccatttg ttacacaggt tgaagcttat aactgaaaat tggattcaaa   240
```

```
gaatcgtaga tgaagaaatc gaagtgagtt gaatattttc tgaacatatg aaaattggaa      300
caagtttttt ctcattttgc tagtttcctg tttttatgtt ttcttgactt taggagatga      360
catatggagg tgaactatac aaaggttgtt gcaacgataa cattctcctt aattcagttt      420
ttgcaactcg gttacaagca ctcagtggac ttttggccaa gacaattttt tttttttttt      480
ctctctctct aaaatgttat agatacgaat cctttgttga ataaaggaaa aagttgaaca      540
tttgattaca cataagactt taacataatc caactttttt ttatatgaag ctacaaacaa      600
gatttaaaac atcaaagatt ccatctaaac ttcattcatc ttcaatcttc aacatccttc      660
aatgactagt atgtatgtac ataagtaaaa ttgttgataa gaaacaaaa caatgatggg       720 ctaaaatagc ccataaaagg cccattaaac ttgggtttag actttagatt caacgacgcc      780
agattagtga gtcacataac cctcttggaa agagtctcaa cacttgcaga gaaaagaac      840 aaggaagatc ccggaaa                                                    857

<210> SEQ ID NO 12
<211> LENGTH: 815
<212> TYPE: DNA
<213> ORGANISM: Arabidopsis thaliana

<400> SEQUENCE: 12
ggaggaggat atgattgttg cttcaacaac tatatatgga tttgataaca atcctttatc       60
ctcggaagat aaaccaaatt tcttaccaaa cccaccaaaa taagtaatta ccagtgttct      120
tcttctaaag acttctataa accaaaacaa gatcacatat aatcattaac ttaaagcaaa      180
acccaaagtc ttgttttatt tgttagtcag ctcaaccatc tttatctgaa actaaactgt      240
ttctctcttc tttgtttctg acaagtcaat gagattggtg tcttctctct gttgcacatt      300
taatattaac ttttgaaaaa ctacaaaacg aaacaaaaca aagaaaagca gacatttaca      360
cgaaattatg cagacatata cacgaaattc aatctacctg aaaatgagaa taagttttga      420
gtaaatttcg tggagactcc tggaaataag tttgtttgtt ttcctatttt tatgtaactt      480
cgcttaaatt tctaattgcc taatcaaggt attaaaatag caaagcttgg tttggctcag      540
tcttcgcgta aactccaaga aacaatcata aaaacaaata aaaagacaa gaaaccaaaa      600 aaaaaaaaaa agttgagaga tttcagtaga tgaaagttgg atagaagatt cgtgtagtta      660
gctacttaat gggccgttaa aatatttaat aaggcccatt gggtctaaac tgtgttagga      720
ttactagggc acagaatcgg tctctgtccc atttcgcgaa cttttctcctt agaatcggaa      780 cggacgaaga aggaagacaa ggaagaagat cggag                                815

<210> SEQ ID NO 13
<211> LENGTH: 421
<212> TYPE: DNA
<213> ORGANISM: Artificial Sequence
<220> FEATURE:
<223> OTHER INFORMATION: IN1

<400> SEQUENCE: 13
cagtgagtca cataaccctc ttggaaagag tctcaacact tgcagagaaa agaacaagg       60 aagatcccgg aaacaggtaa tttctctcct ctctattttt accatttttcc attgacgacg     120 atctaggttt tctgatttga ttttggagaa cgcctcgatg agtttataga ttcgtagatt      180
ggttttgaga ttcagtataa tttcacccgg attccaattt ttgaaccgat acctaatttt      240
gaattgattt ggtagatcga ttggtcaaat ttgaaattga ttttctccca taatatctga      300
```

| | |
|---|---|
| agcgtcttat tggatcaaat ctacaacatt tctctgttga aaggatcgat ttttttttc | 360 |
| ttggaacatg ataacttttg attattcatc aaagttttgt tcttttaat atttcacagg | 420 |
| t | 421 |

<210> SEQ ID NO 14
<211> LENGTH: 819
<212> TYPE: DNA
<213> ORGANISM: Artificial Sequence
<220> FEATURE:
<223> OTHER INFORMATION: IN2

<400> SEQUENCE: 14

| | |
|---|---|
| cagatttcgc gaactttctc cttagaatcg gaacggacga agaaggaaga caaggaagaa | 60 |
| gatcggaggt aagccttttc gatcctttaa tcgtcgatgt tggatcttag atctggattc | 120 |
| ttcacgttct tgtgttctcg attcctgatt tgttttgag taatttgttg gaataatctg | 180 |
| atttcctaaa agttatcgga attaagtgga aagtgaatca tctgcttctg gatttgatct | 240 |
| tcgattttgc atttaacctt tcctctgctt ctggatttga tcagttcaat actatcttca | 300 |
| tacaatgttg ttatgtccaa attgttgaat ttttcattta gagttagctt cagagaaaac | 360 |
| aacaaaacta gtagtatgtg tgaaacaaga acatgaagaa gatggaaagc tgattgggaa | 420 |
| cattgcattt agatgtcttt tctcgtttat gtttggatct caattcttca tgttcttgtt | 480 |
| gtgtgtcatt gaaattgttg gaatacgtag atatcagagt aggtcatttt gggaaagcta | 540 |
| ttgaatttaa gaggaagatg aatcatttta acaagctcca tcgattttgc gcttaatctg | 600 |
| tctctcttct gcttctggat tgattaatt tcattctatt tgttttctc ataagttgtt | 660 |
| gttatgttca aattgttgaa tttggaatga tttcatttct caaatagggt ttactgagac | 720 |
| aatgattcca gatttagtct atctgaaaat ggttcagctt tcttcttgtt gatccatttg | 780 |
| tctaacattc tctcatgttt ttgttttttcc ttgacaggt | 819 |

<210> SEQ ID NO 15
<211> LENGTH: 1326
<212> TYPE: DNA
<213> ORGANISM: Artificial Sequence
<220> FEATURE:
<223> OTHER INFORMATION: SP1/IN2

<400> SEQUENCE: 15

| | |
|---|---|
| aaatagggtt tttctccccc cacggcccac cacggcccac ctaggcccac cctaaaaaaa | 60 |
| ccctaggtgg gtgggcccat tttttttttt tttttttttt ttttaggtgg ggtgggccgt | 120 |
| gggggaggt gggccgtggg cccatgaaaa aaaaaaata gggttgggcc cacctaaaaa | 180 |
| aaaaaccta gggtgggccc aaaaaaaaaa aaaaaatgg gcccacccta tagggttttt | 240 |
| tttttttta agagtccgga cttccagaag aataataatc tcggcccacg tctaaaaaag | 300 |
| aaaccaccca tccgtccatg ggcccacctc agaccggccc accaagacaa agcccaccaa | 360 |
| cggtgggccg gcccattggt tcacagtcac ggccacggc ccaccggcc caccgctcta | 420 |
| taaaccctat ataagaaacc ctccacctcc tcgccctctt ggtttcctcc ctcttccgcc | 480 |
| gcacacaccc acccagagat cggaccgcag atttcgcgaa cttctccctt agaatcggaa | 540 |
| cggacgaaga aggaagacaa ggaagaagat cggaggtaag ccttttcgat cctttaatcg | 600 |
| tcgatgttgg atcttagatc tggattcttc acgttcttgt gttctcgatt cctgatttgt | 660 |
| ttttgagtaa tttgttggaa taatctgatt tcctaaaagt tatcggaatt aagtggaaag | 720 |
| tgaatcatct gcttctggat ttgatcttcg attttgcatt taacctttcc tctgcttctg | 780 |

-continued

```
gatttgatca gttcaatact atcttcatac aatgttgtta tgtccaaatt gttgaatttt     840
tcatttagag ttagcttcag agaaaacaac aaaactagta gtatgtgtga aacaagaaca     900
tgaagaagat ggaaagctga ttgggaacat tgcatttaga gtctttttct cgtttatgtt    960
tggatctcaa ttcttcatgt tcttgttgtg tgtcattgaa attgttggaa tacgtagata   1020
tcagagtagg tcattttggg aaagctattg aatttaagag gaagatgaat cattttaaca   1080
agctccatcg atttttgcgct taatctgtct ctcttctgct tctggatttg attaatttca   1140
ttctattttg ttttctcata agttgttgtt atgttcaaat tgttgaattt ggaatgattt    1200
catttctcaa atagggttta ctgagacaat gattccagat ttagtctatc tgaaaatggt   1260
tcagctttct tcttgttgat ccatttgtct aacattctct catgttttg tttttccttg    1320 acaggt                                                               1326
```

<210> SEQ ID NO 16
<211> LENGTH: 1028
<212> TYPE: DNA
<213> ORGANISM: Artificial Sequence
<220> FEATURE:
<223> OTHER INFORMATION: SP2/IN1

<400> SEQUENCE: 16

```
gctagcgctt atggagcgtg atggactgaa agagacccct accacgtgtt gacgtaagca     60
atgacataaa accgatccta atctctccta cgaacgacag cggagagtac tgctgaaagc    120 tatgcttttta tttttctttta tttttctcgt cagtggaata cacgttttgt cggtgtgtgt    180
ccttttccaa agaaagacgg aactgcctag acaacgtcg gctaccaaag cacaatgtaa     240
agtagacatg atgatcgacg acgtcatgca tgacgtttaa catgcattgt atgtgtccgt    300
cagtctataa ataggtcaag aacaaacatc gagaaaggc agaggcgaaa tacccatctg     360
cctatctctc aagaaataac tctctcttgt tcttcatcct ttctttcata gtttaaaaac    420
ctgaaattgg gcaagcccca taggcatttt ggtatcagag cgagtaagga caagtaggta    480
agtccctaaa atacttctat caataaaatt tctacgccaa gaagggtaag ttgtacgttt    540
atcctacacc cttgtgtttg taaccaggct tggtcaagtg cacaagggta tttgagtccc    600
cggaccgcag tgagtcacat aaccctcttg gaaagagtct caacacttgc agagaaaaag   660
aacaaggaag atcccggaaa caggtaattt ctctcctctc tattttacc attttccatt     720 gacgacgatc taggttttct gatttgattt tggagaacgc ctcgatgagt ttatagattc   780
gtagattggt tttgagattc agtataattt cacccggatt ccaattttg aaccgatacc    840 taattttgaa ttgatttggt agatcgattg gtcaaatttg aaattgattt ttctccataa   900
tatctgaagc gtcttattgg atcaaatcta aacatttct ctgttgaaag gatcgatttt    960
ttttttcttg gaacatgata acttttgatt attcatcaaa gttttgttct ttttaatatt   1020
tcacaggt                                                             1028
```

<210> SEQ ID NO 17
<211> LENGTH: 1426
<212> TYPE: DNA
<213> ORGANISM: Artificial Sequence
<220> FEATURE:
<223> OTHER INFORMATION: SP2/IN2

<400> SEQUENCE: 17

```
gctagcgctt atggagcgtg atggactgaa agagacccct accacgtgtt gacgtaagca     60
```

| | |
|---|---|
| atgacataaa accgatccta atctctccta cgaacgacag cggagagtac tgctgaaagc | 120 |
| tatgctttta tttttcttta tttttctcgt cagtggaata cacgttttgt cggtgtgtgt | 180 |
| ccttttccaa agaaagacgg aactgcctag acaacgtcg gctaccaaag cacaatgtaa | 240 |
| agtagacatg atgatcgacg acgtcatgca tgacgtttaa catgcattgt atgtgtccgt | 300 |
| cagtctataa ataggtcaag aacaaacatc gagaaaggc agaggcgaaa tacccatctg | 360 |
| cctatctctc aagaaataac tctctcttgt tcttcatcct ttctttcata gtttaaaaac | 420 |
| ctgaaattgg gcaagcccca taggcatttt ggtatcagag cgagtaagga caagtaggta | 480 |
| agtccctaaa atacttctat caataaaatt tctacgccaa gaagggtaag ttgtacgttt | 540 |
| atcctacacc cttgtgtttg taaccaggct tggtcaagtg cacagggta tttgagtccc | 600 |
| cggaccgcag atttcgcgaa ctttctcctt agaatcggaa cggacgaaga aggaagacaa | 660 |
| ggaagaagat cggaggtaag ccttttcgat cctttaatcg tcgatgttgg atcttagatc | 720 |
| tggattcttc acgttcttgt gttctcgatt cctgatttgt ttttgagtaa tttgttggaa | 780 |
| taatctgatt tcctaaaagt tatcggaatt aagtggaaag tgaatcatct gcttctggat | 840 |
| ttgatcttcg attttgcatt taaccttttcc tctgcttctg gatttgatca gttcaatact | 900 |
| atcttcatac aatgttgtta tgtccaaatt gttgaattt tcatttagag ttagcttcag | 960 |
| agaaaacaac aaaactagta gtatgtgtga acaagaaca tgaagaagat ggaaagctga | 1020 |
| ttgggaacat tgcatttaga tgtcttttct cgtttatgtt tggatctcaa ttcttcatgt | 1080 |
| tcttgttgtg tgtcattgaa attgttggaa tacgtagata tcagagtagg tcattttggg | 1140 |
| aaagctattg aatttaagag gaagatgaat cattttaaca agctccatcg attttgcgct | 1200 |
| taatctgtct ctcttctgct tctggatttg attaatttca ttctattttg ttttctcata | 1260 |
| agttgttgtt atgttcaaat tgttgaattt ggaatgattt catttctcaa atagggttta | 1320 |
| ctgagacaat gattccagat ttagtctatc tgaaaatggt tcagctttct tcttgttgat | 1380 |
| ccatttgtct aacattctct catgtttttg tttttccttg acaggt | 1426 |

<210> SEQ ID NO 18
<211> LENGTH: 928
<212> TYPE: DNA
<213> ORGANISM: Artificial Sequence
<220> FEATURE:
<223> OTHER INFORMATION: SP3/IN1

<400> SEQUENCE: 18

| | |
|---|---|
| aacataactt gtatatttaa acataaagat aaaccttctt agagagaaca tatttaaatt | 60 |
| gtgttatcca ttactttttaa taaggaaata taatctttc agtttgaatt gaaaataact | 120 |
| ttatcaaaat ttatgacaaa tacaaataaa aaccaaaaca acaaaagaat tgtgtatatg | 180 |
| ttattgagaa acgattttta ttcactcgta catgattcat agaaaatttt aatttagtat | 240 |
| aaaaagtata aatataatat taatcaaata aattcttatg aaataaataa attcttcttc | 300 |
| aagggtaaat gaaaccttat gagtaaagtc tattctgcac ttaaaagaaa agagaattga | 360 |
| gtattttttg gaagcccatt tgggcccatt ttaaaatata ataagaaag cccaataatg | 420 |
| agaattaaaa accctagttt tcttcccctc ctatataaat cgacattttg ttcgttcctt | 480 |
| ctcttctctt ctcttcctct cggaccgcag tgagtcacat aaccctcttg gaaagagtct | 540 |
| caacacttgc agagaaaaag aacaaggaag atcccggaaa caggtaattt ctctcctctc | 600 |
| tattttttacc atttttccatt gacgacgatc taggttttct gatttgattt tggagaacgc | 660 |
| ctcgatgagt ttatagattc gtagattggt tttgagattc agtataattt cacccggatt | 720 |

```
ccaattttg aaccgatacc taattttgaa ttgatttggt agatcgattg gtcaaatttg      780
aaattgattt ttctccataa tatctgaagc gtcttattgg atcaaatcta caacatttct      840
ctgttgaaag gatcgatttt tttttcttg gaacatgata acttttgatt attcatcaaa      900
gttttgttct ttttaatatt tcacaggt                                         928
```

```
<210> SEQ ID NO 19
<211> LENGTH: 1326
<212> TYPE: DNA
<213> ORGANISM: Artificial Sequence
<220> FEATURE:
<223> OTHER INFORMATION: SP3/IN2

<400> SEQUENCE: 19
aacataactt gtatatttaa acataaagat aaaccttctt agagagaaca tatttaaatt       60
gtgttatcca ttactttaa taaggaaata taatcttttc agtttgaatt gaaaataact      120
ttatcaaaat ttatgacaaa tacaaataaa aaccaaaaca caaaagaat tgtgtatatg      180 ttattgagaa acgattttta ttcactcgta catgattcat agaaaatttt aatttagtat      240
aaaaagtata aatataatat taatcaaata aattcttatg aaataaataa attcttcttc      300
aagggtaaat gaaaccttat gagtaaagtc tattctgcac ttaaaagaaa agagaattga      360
gtattttttg gaagcccatt tgggcccatt ttaaaatata ataaagaaag cccaataatg      420
agaattaaaa accctagttt tcttcccctc ctatataaat cgacattttg ttcgttcctt      480
ctcttctctt ctcttcctct cggaccgcag atttcgcgaa cttttctcctt agaatcggaa      540 cggacgaaga aggaagacaa ggaagaagat cggaggtaag ccttttcgat cctttaatcg      600
tcgatgttgg atcttagatc tggattcttc acgttcttgt gttctcgatt cctgatttgt      660
ttttgagtaa tttgttggaa taatctgatt tcctaaaagt tatcggaatt aagtggaaag      720
tgaatcatct gcttctggat ttgatcttcg attttgcatt taacctttcc tctgcttctg      780
gatttgatca gttcaatact atcttcatac aatgttgtta tgtccaaatt gttgaatttt      840
tcatttagag ttagcttcag agaaaacaac aaaactagta gtatgtgtga aacaagaaca      900
tgaagaagat ggaaagctga ttgggaacat tgcatttaga tgtcttttct cgtttatgtt      960
tggatctcaa ttcttcatgt tcttgttgtg tgtcattgaa attgttggaa tacgtagata     1020
tcagagtagg tcattttggg aaagctattg aatttaagag gaagatgaat catttaaca      1080 agctccatcg attttgcgct taatctgtct ctcttctgct tctggatttg attaatttca     1140
ttctattttg ttttctcata agttgttgtt atgttcaaat tgttgaattt ggaatgattt     1200
catttctcaa atagggttta ctgagacaat gattccagat ttagtctatc tgaaaatggt     1260
tcagctttct tcttgttgat ccatttgtct aacattctct catgttttg tttttccttg     1320 acaggt                                                                1326
```

```
<210> SEQ ID NO 20
<211> LENGTH: 928
<212> TYPE: DNA
<213> ORGANISM: Artificial Sequence
<220> FEATURE:
<223> OTHER INFORMATION: SP5/IN1

<400> SEQUENCE: 20
acatttcggt tatctgggta ctacataaag attgccaagt ccattgattg aattgtgtgt       60
gtttttatgg ctcacttata cgttgtcttt tttaacaaaa aatgttttca actaatttga      120
```

```
attttgttta caaacaaata caaataacca ttggtttctc aagaatcaat caagaattag    180
aaatgatatg atagatttct caataaaaga caaaattttc aattttttca gttttgtaa    240 atctacagca tcatttgtga tatgtctatc aaattttgct taaataaata aatcctcaaa    300
tactttgaat gagtaaaaat gaaaaatta ggcttacata gtaattaaat aggcttcaaa    360
aaggctaagg cccaaatttg ttaaattaag aattgaagtc caaaaccta tgttaaaaca    420 atctaggtta gggtttcttc tctcctatat attctataaa ctaggtcatt ccattcgtca    480
aactcctctc ttgcaaactc cggaccgcag tgagtcacat aaccctcttg gaaagagtct    540
caacacttgc agagaaaaag aacaaggaag atcccggaaa caggtaattt ctctcctctc    600 tattttacc attttccatt gacgacgatc taggttttct gatttgattt tggagaacgc    660
ctcgatgagt ttatagattc gtagattggt tttgagattc agtataattt cacccggatt    720 ccaattttg aaccgatacc taattttgaa ttgatttggt agatcgattg gtcaaatttg    780
aaattgattt ttctccataa tatctgaagc gtcttattgg atcaaatcta caacatttct    840
ctgttgaaag gatcgatttt tttttcttg aacatgata actttgatt attcatcaaa    900 gttttgttct tttaatatt tcacaggt                                         928

<210> SEQ ID NO 21
<211> LENGTH: 500
<212> TYPE: DNA
<213> ORGANISM: Artificial Sequence
<220> FEATURE:
<223> OTHER INFORMATION: SP3good90

<400> SEQUENCE: 21
taaataaatt gtctttgtca acataaagat aaaccttctt agagagaaca tatttaaatt     60
ttgttatcca ttactttaa taaggaaaaa atatcttttc agtttgaatt gaaatccact    120
tcaaccacgc ttttgacaaa tacaaatcca aaccaaaaca acaaagaat tgtgtatatg    180 ttattgagaa acgattttc ttcactcgta catgattcgt acaaaaatct aatttagtat    240
aaaaagtata tataatat taatcaaata aagtcttatg aaataaatac attcttcttc    300
aagggtaaat gaaacctaat gagtaaagtc tattctgcac ttcaaagaaa atagaattgg    360
gtattcatgg gaagcccatt tgggcccatt ttaaaatggg gcaaataaag cccaataatg    420
agaataaaaa accctagttt tcttcccctc tatataaat cgacatttca ttcgttcctt    480
ctcttctctt ctcttctttt                                                500

<210> SEQ ID NO 22
<211> LENGTH: 500
<212> TYPE: DNA
<213> ORGANISM: Artificial Sequence
<220> FEATURE:
<223> OTHER INFORMATION: SP4good90

<400> SEQUENCE: 22
aaattgttga tagaattccg aacagaacat aacttaactt gaaatataaa tcaattatca     60
gaaatacgtt cacgttcatc cgattttgtc ttttcgattg tataacttgt caacttcgac    120
atctcaacag ataaaacaaa accactttgt tgagaatcca aaactaggtt ttgattgaga    180
agatgatatg attcagaata cagttatata caaaatgttt tctgcatatt tccaattttg    240
tcaaatgtca ctattcattg tcaaacacta ttcaattaaa ttagatgaaa caatacttgg    300
attaatgagt taaaaatgg gcctaagtta gttatcac tcaaagtaa ttgagcaatt    360 cataattggc ccatttgacc gagtttgtaa agctaaaatt ttaaaggccc aaaacccaga    420
```

```
ttagggtttc aacagaaacc tataaggaga ctctatataa actctctctt cgttcattag    480
ggtttctcct tctctgaaga                                                500

<210> SEQ ID NO 23
<211> LENGTH: 500
<212> TYPE: DNA
<213> ORGANISM: Artificial Sequence
<220> FEATURE:
<223> OTHER INFORMATION: SP5good90

<400> SEQUENCE: 23
attgctgggt tatctgggta ctacataaag attgccaagt ccattgatag aattgtgtgt     60
gttttgatgg ctcacttata cgttgtctgt tctaacaaaa tatgtttgca actaacttcg    120
attttatgaa caaacagata caaataacca ttggtttctc aagaatcctt caagagttag    180
aaatgatatg atagatttct caataaaaga caaaatttta cagttttca gttttgtaa     240 ctctacagca tcacttgtga tatgtctatc aaatttcgtt tgactaaata aatcctcaaa    300
tactttgaat gagtaaaaat gaataatta ggcttaagta gtaatttgat aggcttcaaa     360
acggctaagg cccaaatttg ttaagttaag aattgaagtc caaagcccaa tattaaaaca    420
atctacccta gggtttcttc tctcctatat attctataaa ctaggtcttc ccattggtca    480
aactcctctc ttgcaaactc                                                500

<210> SEQ ID NO 24
<211> LENGTH: 500
<212> TYPE: DNA
<213> ORGANISM: Artificial Sequence
<220> FEATURE:
<223> OTHER INFORMATION: SP3good80

<400> SEQUENCE: 24
ttccaaactt gtatgttaga acataacata aaacctactt agagagagaa ttgcatgtga     60
ttgtgatcca ttacttttat ctgcgaaatc cgattttttc agtttgaatt gaatgttact    120
ttatcaagac tcttgacaaa cacaaaattt cgccaaaaca acaaaagaat tgtgtatagg    180
tttttgagaa acgattttgg tgctctcgta catgattgga tggaaaatta aatttagtat    240
aaaaagtgtc actataatat gtgccaaaca tatacttatg aaataaataa attcttcttc    300
aagggtaaat gaatcctagt tggttaacgc aattctgcac tagatagaaa ggcctattga    360
gtattgatgg gaagcccatt tgggcccatt ttaagttaag ctaaggaaag cccaatagtg    420
agaataaaaa accctagttt tcttcccctc ctatataaat cgacattttg ttccttcgtt    480
cacttctctt ctcttcctct                                                500

<210> SEQ ID NO 25
<211> LENGTH: 500
<212> TYPE: DNA
<213> ORGANISM: Artificial Sequence
<220> FEATURE:
<223> OTHER INFORMATION: SP4good80

<400> SEQUENCE: 25
taattgttga gagaatccat aacataacat aacattacaa gaattctggt tcaaattgga     60
gaaatacttt agctgttttc tgtttttgtc ttttcgattg tttcagtttt caacttgaac    120
atctcaacag ataaaacgta accaacttgt tgagaatcca ataaaagaat tgtttgaga    180 agatgatatg atagataaaa cagttatact caaaatgttt tctgcatatt tccaatttttg    240
```

```
tcgaatgtca ctataaagtg tcaaacacta agacagata aataaataat gattacttgg      300
attgaggagc aaaaatttgg gcctaaacgc attaaaaacc tccctatcaa ggcccaagat      360
cattattggc ccatttttacc gagtttatta agctaaaatt ttaaaggccc aaaacctata    420
ttagggtttc aacagaaacc tataaggaga ctatatataa actctcgtct cgttcattag     480
ggtttctctt gctcataaga                                                 500

<210> SEQ ID NO 26
<211> LENGTH: 500
<212> TYPE: DNA
<213> ORGANISM: Artificial Sequence
<220> FEATURE:
<223> OTHER INFORMATION: SP5good80

<400> SEQUENCE: 26
atgtctgtgt tatctgggta ctacataaag aggcccaagt caattgagag aactgtgtgt     60
gtgttgatgg ctcacttcta cgttgagttt tttaacaaaa aatcatttca actagtttga    120
atttaacaaa caaacagata gaaataacca ttggtctctc aagaatcatt caagtataga    180
agatgatatg atagatttct ctaccaaaga caaaattgtc gtatttgtca gttttttgtaa  240 atctacagct tcatttgtga tatgtctatc aaagcttgaa taattaaatt tttcctcaaa    300
tccttggcct gagtaaaaat gaaagaaaa ggcttacata gtaattttat aggcttagat     360
gggcctaagg cccattattg taagttaaag aattgaagcc caaaccctag aattaaaaca    420
atccatatta gggttttgcc gcacctatat attctataaa ctaggtcaac tctttcgtcg    480
aacccttctc ttgcaaactc                                                500

<210> SEQ ID NO 27
<211> LENGTH: 500
<212> TYPE: DNA
<213> ORGANISM: Artificial Sequence
<220> FEATURE:
<223> OTHER INFORMATION: SP3good70

<400> SEQUENCE: 27
acgagacttt gttttgagtg agttgaagat aaacgttgag atagagagat gtgtgtgtgt     60
tttttatcca tcacttagcc aaatgcacaa aaatgttttc agtttgaatt ggacttcgct    120
tttccatcct tgttgacaaa tacaaatata atccaataca aaacgatcag aattagtttt    180
ccttttagaa acgatttaga ttctctcgta catgattgga gacaacatcc aatttaataa    240
acaaagtaat tcattgttac tattcaaaca cagccgtgag agataaatac attcttcttc    300
aagggtaaat gaaagccaat gagttaagtc tattctgcac taaaagcaaa atagaattgg    360
gtattgaccg gaagcccatt tgggcccatt ttaattctca ccaataacgg cccaatattg    420
agaattaaaa accctagttc tcttcccctc ctatatatat cgacatcgct gccattcgtt    480
cctctcttct cttctcttcc                                                500

<210> SEQ ID NO 28
<211> LENGTH: 500
<212> TYPE: DNA
<213> ORGANISM: Artificial Sequence
<220> FEATURE:
<223> OTHER INFORMATION: SP4good70

<400> SEQUENCE: 28
ccattgttga gagaatccat aacataacat aactgtgact taactgatct tcctgtgagt     60
gaaatactta tcacttcatc cgatttttgtt tttgcgatag tagttactct caacttcgac   120
```

```
atctcaacag ataagataat acagaaatag tgagaatcca aaacgaacat cagtttgaga    180
agatgatatg ataacaagta cagttgaagt gaaaatcttt tctgcatttt taaaatcttc    240
acgaatgtca ctaatctatg tcaaacacta ttcactgaaa tacgatttgg tgatactttg    300 aggaagggt taaaaatgg gcctaaactc taaaacacac taaaaaggcg tttaataggc      360
```
```
aggaaggggt taaaaatgg gcctaaactc taaaacacac taaaaaggcg tttaataggc     360
cataattggc ccattgggtc gagtatttta agttaaggcc caaaaggccc aaaccctaaa    420
ttagggtttc aaacctagcc tataaggaga ctctataaaa acccgcctct cgttcattag    480
ggtttctctt cttctgaaga                                                500
```

<210> SEQ ID NO 29
<211> LENGTH: 500
<212> TYPE: DNA
<213> ORGANISM: Artificial Sequence
<220> FEATURE:
<223> OTHER INFORMATION: SP5good70

<400> SEQUENCE: 29

```
acttttccgt attctgggta cttcagtaag attgccaagt ccagatagag aactgagtgt    60
gtgttgatgg ctcacttata cgttttctgt tttaacagag aaaaatttca acttgagtga    120
atgtacgaaa tcaacagata catagattca ttggtctctc aagaataatc aaaatataag    180
gaatgatatg ttagatttt ctcatagatt caacttttac attttgtca gttttgttc      240
```
(as printed):
```
gaatgatatg ttagattttt ctcatagatt caacttttac attttgtca gttttgttc      240 ctctacagca ccacgcgtgt tttgtgtttc aaagtcttta tgattaaatc ctcccacaaa    300
tcctttaaat gagtaaaaaa gcaacgtaaa ggctttagta gaaatttgat aggcctttac    360
agggctaagg cccattatta tttgggtaag aattgaagcc ctaaggcaag ggttaaaaca    420
caaccaccta gggtttctct ctccctataa actatataaa cttgttcatt tgttcgttc     480 ctctcttctc ttgcaaactc                                                500
```

<210> SEQ ID NO 30
<211> LENGTH: 500
<212> TYPE: DNA
<213> ORGANISM: Artificial Sequence
<220> FEATURE:
<223> OTHER INFORMATION: SP3bad90

<400> SEQUENCE: 30

```
aacataactt gtatatgtaa agatgaatgt aaaccttctt agagaggaca tatataaatt    60
gtgttatcca ttacttttaa taaggaaatc caagcttttc aggtccaatt gaaaataagt    120
ttatcaaaat ttatgaaaat tacaaataaa aaccaaaaca accaaagaat tatgtatatc    180
ttatggtgga acgattatta ttcactcgta catgattcat agcaaatttt aattgattac    240
aaaaagtata aatataatat taataaaata aacgcttatg aaaagataa attcttcttc     300 aaggccaaat gaaccctttat gagtaacgtc tattctgcac ttaaaaaaaa agagaattga   360
gtattttttt gaagcccata tggccccatt ttaaaatgta ataaagtaag cccaataatg    420
agaattataa agcttagttt tctttcactg ctttataaat cgaccttttg ttcgttcctt    480
cccttctctt atcttcatct                                                500
```

<210> SEQ ID NO 31
<211> LENGTH: 500
<212> TYPE: DNA
<213> ORGANISM: Artificial Sequence
<220> FEATURE:
<223> OTHER INFORMATION: SP4bad90

<400> SEQUENCE: 31

```
aaattgttga tagaatttca aacataatat aactgaacat taaatcttaa ttaattatca      60
gaaatatgat cactataatc cgactttgtc tttcggattt tattaatttt caactaaaaa     120
atctcaacag ataaaacaaa cctactctgt cgataatcca atattttaat tttattgaga     180
agctcatatg acaacgtgta cagatatcta caaaatgttt tctacatatt tccaattttg     240
tcacatgtca attttaagtg tcaaacacta ataaaataaa ctaaattaga ttattttcgt     300
attaatgagt aaaaaaatgg gcctaaacaa attgtatcac taaaaagtaa tttagaaatt     360
cataagtagg ctatatgagt tagttttaa agctataatt ttaaaggtcc aaaacccttc     420
ctaaggtttc gacagaaacc tataaggaga ctctatataa ctcctcccttt cgtgcattag    480
ggtatctcat tctctgaaga                                                 500
```

<210> SEQ ID NO 32
<211> LENGTH: 500
<212> TYPE: DNA
<213> ORGANISM: Artificial Sequence
<220> FEATURE:
<223> OTHER INFORMATION: SP5bad90

<400> SEQUENCE: 32

```
actgttcggt tgtctgggtt ctacataaag attaccaagt ccattgattg tattgcgtgt      60
tttttgtgg cgcacttata cgttgtattt tgtaacgaaa atgtttcca actaatttga      120
attttgtttc caaacaactt caaataatca ttggtttctc aagagtcaac caagaattag     180
aaatggtatg atagatttct caataaacaa caaaattgtc aatttatca gttttggtga     240
agctacagca tcatttgtga tctgtctttc aaattttgct taaataaata aatcctcaaa     300
tagttggaat gagtaaaaat gaaataatta ggcttacata gtatttaaat aggcttcaat     360
aaggctaagg cccaaatttg ttaaattaag aattgaggtc caaaaatcta tgttagaaca     420
ctgtaggtcg gggtttctac tctcctgtat attcgataaa ctcggtcatt ccattcgtct     480
aactaatctc tcgcaaactc                                                 500
```

<210> SEQ ID NO 33
<211> LENGTH: 500
<212> TYPE: DNA
<213> ORGANISM: Artificial Sequence
<220> FEATURE:
<223> OTHER INFORMATION: SP3bad80

<400> SEQUENCE: 33

```
aacatcaagc gtgcatttaa acataaagat aaaccatctt agagagcaca tatctaaatt      60
gtgttagtca tcacctttaa ttagtatata tgatctttc actaccaatg gaggattact     120
ttagctcaat ttatgggact ggcataggat atccaaaaca ataacagaac tgtggctatg     180
caaatgggga acgatttta ttcacttgtg catgatttct agaaggtttt tattttgtat      240
aaaaagtata aacataatat taatcaaata aatgcttttg aaatacataa atacttctgc     300
aagggtaaat gcaacctaat ctgtaacgtc tattctgctt gtaagaaaat agagatgtga     360
ttatattttg gaagcccata tggtgacatc ttaaaatata ataagaaat ccgaataatg      420
cgagttaaac accgtagttt tcttcccctg tcatatagat cgacatttag atcgttcctt     480
ctcttaggct gtcttcctct                                                 500
```

<210> SEQ ID NO 34
<211> LENGTH: 500

<212> TYPE: DNA
<213> ORGANISM: Artificial Sequence
<220> FEATURE:
<223> OTHER INFORMATION: SP4bad80

<400> SEQUENCE: 34

```
aaatcgctgt tataatttca aacataacag accataaaat taaattttac ttaattctca    60
tatatacgat aactatcatc ctatgttgtg ttttcgctat tattaatctt caactaaatc   120
atataaattg gcaaggcaaa cccacttttt tgataatcca atcttttaat tttattgaga   180
aggttatatg ctaaagtata ccgttatata caaaatgctt tctccatatt tgagattgtg   240
ttggaagtcc cacttaggtg tcgaacgcta aaaaaatcaa atatcgtaac tcatactttg   300
attaatgagt actaccatgg tcctaaacaa atgataacaa taagaagtaa tttagaaatt   360
cataagtggc tcatctaatt gagttttta agctacaatt ataagggggcc aacacccttc   420
tttggcttta taacataacc tctaaggagg ctctctttaa accctctatt cggtcattag   480
gctcttgcct tctctgaaga                                                500
```

<210> SEQ ID NO 35
<211> LENGTH: 500
<212> TYPE: DNA
<213> ORGANISM: Artificial Sequence
<220> FEATURE:
<223> OTHER INFORMATION: SP5bad80

<400> SEQUENCE: 35

```
acactcggat tatttgagta ctccattagg attgccgtct ccctagattg aattatgtgt    60
gattttctcg cccacttgta cgttgtcttg ttccacaaaa aatcttttt attaatttga   120
ctatcgtttc taaacaaata cacataacga ttggatcccc tagagtcaat gaagaattac   180
aaatgatatg gtagatttct aaagaaaaga caaaattgtc attttttttca gtgtatgtat   240
atcttcagag ccatttgtgt taggtctagc aagttctgct taaataaata aatcctcata   300
tacttagagt gcctaaaaag taaagtatta gtcttaaatg gtcgttagac taaccccaaa   360
aaggtcaagg cttaaatttg ttatatcaag tatttaagtc aaaaaaccta tctttaagga   420
atcaaggtta aggttgctta actcccattt atcctataaa cttggtcatt ccattcgtca   480
aattccgctc ttgcaaattc                                                500
```

<210> SEQ ID NO 36
<211> LENGTH: 500
<212> TYPE: DNA
<213> ORGANISM: Artificial Sequence
<220> FEATURE:
<223> OTHER INFORMATION: SP3bad70

<400> SEQUENCE: 36

```
aacctaattt gcgtatacaa atatagcgat tcaccttctt agaaacaaca tacttagtag    60
gtgtcataaa gtgcatgtaa taaggatgta taatctttt attctgaatt ttagataaca   120
ctattaatat taatgacaaa tataaacaga atcatagaca caacaagcaa ggagtaaatg   180
ggatcgagaa acgattttc tttactcgta cgtcatcgat agaaacttag aacgccctct   240
caaacgttta agtataatac caaccagaca aattcacatg aagttaaaaa atacttcttt   300
tggggtaaat gaaacctaac gaggaaagcc ttttcgctac ttaaacataa agagacatga   360
gacgtatatg gcttcccgtt aatccccaat ttaaaattta tcacacttag ccggattacg   420
tgagtataaa attctcgcct tcgtgccctc ctttatagat cgagactttt ttctttagtt   480
```

```
ctagcttctt gactatcctt                                              500

<210> SEQ ID NO 37
<211> LENGTH: 500
<212> TYPE: DNA
<213> ORGANISM: Artificial Sequence
<220> FEATURE:
<223> OTHER INFORMATION: SP4bad70

<400> SEQUENCE: 37
caattgctga aagaatttca gtcataacat aactcaacat gatttcctaa tccactattt    60
aatatacgtg ccccatcctc caggttagtc tcctcgcctt gagtaatttt taagtataaa   120
atcatgacag atgaaagaaa tgcactttgg tgaggatcca atattgtaat ataatttaga   180
cattgatatg aaaaaggctt caagtattta cataaggact catgcatata ttgaatttcg   240
cttagcgtca gtctcgcagc tgaaagacta ataaaataca atacgataaa taatacttgg   300
attaatgagt acaaaaatac gcctagtcga ctgtgatttg gcaaaaataa tttagaaatc   360
gctaatcaac caagttgact cattttttta ggcctaaatt tcacagttcc taccctctga   420
ttactgttac aatagagtcc tataggaatt ctctatctaa agctcgtgat cgttacacag   480
ggtgtcactt tctgtgaaaa                                              500

<210> SEQ ID NO 38
<211> LENGTH: 500
<212> TYPE: DNA
<213> ORGANISM: Artificial Sequence
<220> FEATURE:
<223> OTHER INFORMATION: SP5bad70

<400> SEQUENCE: 38
aggtcggacc tatcttggga cgacatagcc attgccaata ggcacaatcg tattctgtgc    60
gttttaatgg ctcccttatt gtttgccttt tttaaaaaga tatctgttca cctaattgct   120
attatgttca cgcacacttt ccaagaacga taggtatctc aagaaacagt caataagtag   180
aactactatg atagtcatct tattaaaaga ccaaatcttg aatcttttca gttttttga    240 atctatagca tctttggggt tacgtctttc aaccatggct taaataaaaa cttgcgcaaa   300
aactttggat tgctaaatat aaacttatta tcggtacatg gtgattataa aggcttcaaa   360
aacgcaaagc ccgtagttgg ttaatctcag agttgcgatt gagaataata tatttaaaca   420
gactcggtag gcgtcacctc tctccgattg aatcagtaaa ctaaatcaac cctttctgga   480
aaccgctctc ctgcaaacgc                                              500

<210> SEQ ID NO 39
<211> LENGTH: 7
<212> TYPE: DNA
<213> ORGANISM: Artificial Sequence
<220> FEATURE:
<223> OTHER INFORMATION: TATA box, where W indicates T or A

<400> SEQUENCE: 39 tatawaw                                                              7
```

METHODS FOR MAKING GENETIC REGULATORY ELEMENTS

CROSS-REFERENCE TO RELATED APPLICATIONS

The present application is a continuation application of U.S. application Ser. No. 13/599,255, filed Aug. 30, 2012, which claims the benefit of U.S. Provisional Application No. 61/529,001, filed Aug. 30, 2011, and U.S. Provisional Application No. 61/535,117, filed Sep. 15, 2011. The entire contents of the above applications are incorporated by reference as if recited in full herein.

TECHNICAL FIELD

The invention generally relates to methods for making regulatory elements, such as promoters and expression-enhancing introns, and relates to polynucleotides, transgenic cells, and transgenic organisms produced with these methods.

SEQUENCE LISTING

The contents of the text file submitted electronically herewith are incorporated herein by reference in their entirety: A computer readable format copy of the Sequence Listing (filename: GRAS-003-01US_ST25.txt, date recorded: Aug. 30, 2012, file size 22 kilobytes).

BACKGROUND OF THE INVENTION

The production of transgenic cells and organisms through incorporation of heterologous gene(s) is routinely practiced by molecular biologists. Methods for incorporating an isolated nucleotide sequence into an expression cassette, producing transformation vectors, and transforming many types of cells and organisms are well known. However, the regulation or control of the gene's expression can be critical in the development of transgenic cells and organisms for commercial use. For example, in transgenic plants containing a heterologous gene conferring tolerance to herbicide that is normally toxic to the plant, it can be critical for the heterologous gene to be expressed in a temporal and spatial manner, for example, corresponding to when the plant is exposed to the herbicide, and to what parts of the plant the herbicide normally exerts its phytotoxic effect.

The current ability to control expression of transgenes has its limitations. For example, while it is common to introduce or "stack" multiple transgenes into a single transgenic organism, such as a crop plant, stacking can be problematic when the same genetic regulatory elements are used more than once. The use of multiple copies of the same regulatory sequence within two or more transgenes in a single plant is known to promote the activation of gene silencing mechanisms (Halpin (2005) *Plant Biotech. J.* 3:141-155). Silencing of transgenes previously showing stable expression can also be triggered 'de novo' when a new transgene is added by crossing or re-transformation if, for example, the same promoter has been used in both transgenes in an effort to promote coordinated expression (Halpin (2005) *Plant Biotech. J.* 3:141-155). The problem is compounded by the lack of known promoters providing desired patterns and levels of expression. For example, the Cauliflower Mosaic Virus (CaMV) 35S promoter is frequently used as the promoter in plant transgenes because it provides for high-level constitutive expression of an operably linked gene of interest. Because suitable, well characterized promoters are few, the CaMV 35 promoter is often used to drive the high-level constitutive expression of two or more transgenes in the same plant.

Additional promoters and other genetic regulatory elements, and methods for their design, are needed.

SUMMARY OF THE INVENTION

The present invention provides methods for making genetic regulatory elements, and polynucleotides comprising the same. The invention further provides transgenic cells and organisms (including viruses and viral vectors) produced by these methods. The invention thereby provides regulatory sequences to meet virtually any gene expression objective, including the ability to stack a plurality of heterologous genes for expression in a single cell, while avoiding gene silencing or reduced expression levels.

The methods disclosed herein for making regulatory elements are fundamentally different from previous approaches. In the methods of the present invention, regulatory polynucleotide sequences are generated by a computational algorithm rather than by combining sequences from a defined group of sub-sequences (i.e., known cis-elements, consensus motifs, discrete n-mers, etc.). The algorithm can be probabilistic in nature and is used to design polynucleotide sequences to be similar to members of a set of naturally occurring sequences selected to share a known or predicted expression pattern; however, the designed sequences in most cases share little extended homology with the naturally occurring sequences. The algorithm does not require predetermined knowledge of functional motifs, cis-elements, transcription factor binding sites, or trans-acting factors, etc. Because of these characteristics, the computational methods described herein are widely applicable to both promoter and non-promoter regulatory elements, including, for example, introns and 5' and 3' untranslated regions (UTRs), even where little or no functional motif information is available. The invention is applicable to plants, animals, fungi, algae, bacteria, and viruses.

In certain embodiments, the method comprises providing a set of regulatory elements having a selected or predicted property of gene expression in a selected genus or species. Genetic regulatory elements of the present invention include, but are not limited to sequences that comprise promoters, enhancers, introns, terminators, polyadenylation signals, and chromatin control elements. The regulatory elements may comprise 5'-untranslated regions or parts thereof, or 3'-untranslated regions or parts thereof.

In accordance with embodiments of the invention, a set of regulatory elements are aligned, and analyzed for enriched sequences in a position-dependent and/or position-independent manner. The set of regulatory elements may be, for example, a set of regulatory elements from the selected species that are known to provide (or predicted to provide) strong constitutive expression (either in the source species or another species of interest). The set of regulatory elements may have expression properties that are specific to a target cell or tissue. Specifically, starting with a test nucleotide sequence, which may contain basic regulatory motifs (e.g., transcription start site and TATA Box in the case of a promoter) the nucleotide sequence is scored against an algorithm ("scoring function") disclosed herein, and then modified and scored in an iterative or non-iterative manner. In this fashion, a nucleotide sequence is designed that has a statistically significant score with the scoring function, and which is therefore likely to have the selected gene expression property.

As disclosed in detail herein, the scoring function calculates, for each oligomer window (or "word") of a selected size in the nucleotide sequence, a position-dependent or position-independent enrichment in the set of regulatory elements having the selected gene expression property. That is, a window size is selected (such as a 5-mer, 6-mer, 7-mer, 8-mer, 9-mer, or 10-mer), and each oligomer window in the nucleotide sequence is analyzed for a position-dependent or position-independent enrichment in the set of regulatory elements with the selected property. An aggregate score may then be determined, which represents a probability that the sequence has the selected gene expression property. Other properties of the nucleotide sequence may also be scored and incorporated into the analysis, such as sequence complexity and/or A, G, C, and T content.

In other aspects, the invention provides a method for making polynucleotides, expression vectors, transgenic cells, or non-human transgenic organisms, using the methods described herein for producing synthetic regulatory elements. The methods involve operably linking a synthetic regulatory element to a gene of interest so as to produce a polynucleotide for expression in a cell, or an expression construct, which may be introduced into cells, and which may further be propagated or regenerated to prepare transgenic organisms, including transgenic plants.

In still other aspects, the invention provides polynucleotide sequences, vectors, host cells, transgenic plants and non-human organism that are made, at least in part, by the methods described herein.

The invention further provides computer systems and computer-implemented products for performing the methods described herein.

DETAILED DESCRIPTION OF THE INVENTION

Figure 1:
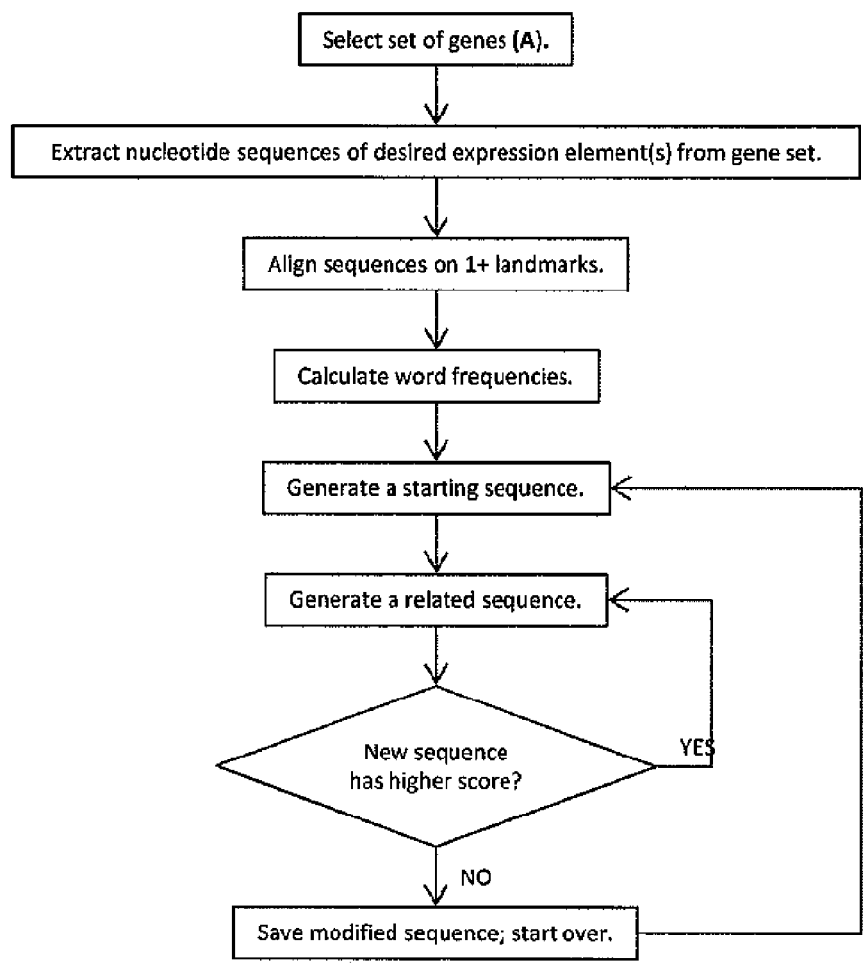
FIG. 1 is a flowchart depicting an embodiment of the method for making a synthetic genetic regulatory element in accordance with the present invention.

The present invention provides methods for making synthetic regulatory elements, and provides transgenic cells, organisms (including viruses and viral vectors), and polynucleotides produced by these methods. The invention thereby provides a variety of regulatory sequences to meet various gene expression objectives, including the ability to stack a plurality of heterologous genes for expression in a single cell, while avoiding gene silencing or reduced expression levels. The invention does not require a biological understanding of cis- and trans-acting factors involved for a particular gene expression pattern, and instead is based upon analysis of genomic data. The invention provides a number of advantages that include: (1) providing a vast source of unique regulatory elements; (2) providing expression patterns, regulation, and characteristics that are not available from naturally occurring regulatory elements; (3) alleviating gene silencing issues; and (4) providing more compact regulatory sequences.

There are relatively few published reports on synthetic regulatory element design, and reports that do exist are confined to designing synthetic promoters. One described approach involves taking well-characterized cis-elements associated with particular expression patterns and placing them upstream of a minimal promoter. As an example, synthetic promoters were produced by placing light responsive elements in front of a NOS-minimal promoter; the resulting sequence conferred light-inducible gene expression (Puente et al. (1996) EMBO J 15:3732-3743). In another example, cis-elements associated with pathogen-induced genes were placed upstream of the 35S-minimal promoter to create synthetic promoters that direct local pathogen-inducible expression (Rushton et al., (2002) Plant Cell 14:749-762). Similarly, U.S. Pat. No. 6,072,050 describes a synthetic core promoter that consists of a TATA motif, a transcription start site, and an intervening sequence that is at least 64% GC-rich, which can be operably linked to upstream activating sequences including a multimerized octapine synthase binding motif and an upstream activating region from the Ubi-1 gene. WO 2001/053476 describes the use of multimerized cis-elements with known regulatory function that can be operably linked to any promoter, synthetic or naturally occurring, to impart additional regulatory control. A second described approach involves random combinations of discrete nucleotide sequences for synthetic promoter construction. For example, combinatorial assembly of known cis-elements followed by screening for functional expression of a reporter has led to the identification of synthetic promoters in bacterial (Kinkhabwala and Guet (2008) PLOS One 3:e2030), yeast (Gertz et al. (2009) Nature 457:215-218), and mammalian (Hahm 2006, U.S. Pat. No. 7,063,947 B2; and U.S. Pat. App. Pub. No. 2004/0175727) cell systems. Randomness has also been incorporated into the cis-elements that are used in combinatorial library approaches (Edelman et al. (2000) PNAS 97:3038-3043). In Edelman, a retroviral synthetic promoter library, comprised of random 18-mers cloned in front of a minimal promoter-GFP cassette, was used to infect Neuro2A cells and cells expressing GFP were selected by FACS. The most active promoters contained combinations of up to 6 known elements.

The present invention in contrast provides methods for designing synthetic regulatory elements from computational analysis of genomic data, and is applicable to plants, animals, algae, fungi, bacteria, and viruses.

In certain embodiments, the method comprises providing a set of regulatory elements having a selected property of gene expression in a selected genus or species. As used herein, the term "regulatory element" refers to a nucleotide sequence that is involved in controlling gene expression in an organism of interest. Genetic regulatory elements of the present invention include, but are not limited to sequences that comprise promoters, enhancers, introns, terminators, polyadenylation signals, and chromatin control elements. The regulatory elements may comprise 5'-untranslated regions or parts thereof, 3'-untranslated regions or part thereof, or intronic sequences. It is recognized that a genetic regulatory element of the present invention such as, for example, an element comprising a promoter, can also comprise one or more additional genetic regulatory elements such as, for example, an enhancer. It is further recognized that genetic regulatory elements can act in concert with other genetic regulatory elements to control the regulation of an operably linked gene of interest. Moreover, it is recognized that an enhancer can, at times, be separated from the transcribed region a gene of interest by 1, 2, 3, or more kilobases of DNA.

In accordance with the invention, a set of regulatory elements are aligned, and analyzed for enriched sequences in a position-dependent and/or position-independent manner. The set of regulatory elements may be, for example, a set of regulatory elements that are known to provide or predicted to provide strong constitutive expression in a species of interest, or which may be specific to a target cell or tissue. Specifically, starting with a test nucleotide sequence, which may contain basic regulatory motifs (e.g., transcription start site and TATA Box in the case of a promoter) the nucleotide sequence is scored against an algorithm ("scoring function") disclosed herein, and then modified and scored in an iterative or non-iterative manner. In this fashion, a nucleotide sequence is designed that has a statistically significant score with the scoring function, and which is therefore likely to have the selected gene expression property. In this context, the term "statistically significant" means that the nucleotide sequence contains a position-dependent or position-independent enrichment of window sequences found in the set of regulatory sequences having the selected gene expression property, and that the level of enrichment is unlikely to occur by chance. For example, a statistically significant score may have a p-value of 0.05 of less, or a p-value of 0.005 or less.

As disclosed in detail herein, the scoring function calculates, for each oligomer window (or "word") of a selected size in the nucleotide sequence, a position-dependent or position-independent enrichment in the set of regulatory elements having the selected gene expression property. That is, a window size is selected (such as a 5-mer, 6-mer, 7-mer, 8-mer, 9-mer, or 10-mer), and each oligomer window in the nucleotide sequence (or in a portion of the nucleotide sequence) is analyzed for a position-dependent and/or position-independent enrichment in the set of regulatory elements with the selected property. An aggregate score may then be determined, which represents a probability that the sequence has the selected gene expression property in a species of interest. Known algorithms may be employed to predict the likelihood that the nucleotide sequence has the selected property, such as Bayes' rule in some embodiments.

The method therefore comprises determining the frequency of short oligomer windows or "words" of predetermined length in these known nucleotide sequences. As used herein, the terms "word" and "oligomer window" are used interchangeably, and mean a short nucleotide sequence. Furthermore, "frequency" may refer to a count of the number of occurrences of each such word; or to the fraction or percentage of all words which such count comprises; or to a ratio of such fractions between two sets of known nucleotide sequences, and thus, reflecting the frequency "enrichment" of a word in one set relative to the other.

The invention can be applied to regulatory sequences in the 5' or 3' untranslated regions of genes, as well as introns. For example, the synthetic regulatory element may comprise one or more of a promoter, an enhancer, a terminator, a polyadenylation signal, an intron, or a chromatin control element, or other expression control signal or motif capable of affecting RNA transcription, mRNA processing, RNA turnover or abundance, or translation of RNA.

The selected property of gene expression may be characterized by one or a combination of gene expression properties. Examples include temporal or spatial control of gene expression in a target organism. In other embodiments, the selected gene expression property includes constitutive expression (e.g., high or low constitutive expression), cell specific expression, tissue specific expression, or organ specific expression. The selected gene expression property in some embodiments is expression in response to biotic stress (e.g., fungal, bacterial and viral pathogens, insects, herbivores and the like) and/or abiotic stress (e.g., wounding, drought, cold, heat, high nutrient levels, low nutrient levels, metals, light, herbicides and other synthetic chemicals, and the like). In further embodiments, the selected property of gene expression is developmental control in one or more of plant stem, leaves, roots, and seeds. In one embodiment, the selected pattern of expression is constitutive expression, such as constitutive expression in plant root, such as constitutive expression in all the tissues of the root.

The natural set of regulatory elements from a source species or organism with the selected gene expression property can be identified from genomic data by known methods, or in some instances such expression patterns have been described. Methods include microarray or RNA-seq analysis to quantify transcripts in cells and tissues of interest, with correlation of expression patterns to the cognate genetic regulatory elements. Examples of gene expression analysis at a genomic level can be found in Hirose et al. (2007) Plant Cell Physiol. 48:523-539; Jain et al. (2007) Plant Physiology 143:1467-1483; Brady et al. (2007) Science 318:801-806; Wang et al. (2009) Plant Cell 21:1053-1069; Li et al. (2010) Nature Genetics 42:1060-1067; and Davidson et al. (2011) Plant Genome (2011) 4:191-203. The target species may be a plant, and various types and species of target plants are described elsewhere herein. Genetic data from these target species may be used for preparing synthetic regulatory elements.

The set of regulatory elements having the selected gene expression property may include all known sequences from a selected species or genus (or virus family), and which are known to exhibit the selected property. Of course, the invention is operable with a subset of these sequences. The set of regulatory elements may comprise at least about 10 regulatory elements up to about 10,000 or more. Preferably, the set of regulatory elements comprises from about 25 to about 300. In certain embodiments of the invention, the set of regulatory elements with the selected gene expression property comprises at least about 25, at least about 30, at least about 35, or at least about 40 elements, or at least about 100 elements. In other embodiments, the invention employs at least about 300, at least about 350, or at least about 400 of such regulatory elements. Sequences can be obtained from the various publicly available genomes. The method does not depend on a particular number of genes in the set of regulatory elements. It is recognized that the number of genes will vary depending on a number of factors including, for example, the choice of target organism, the genetic regulatory element, and the word or window length. Generally, a sufficient number of sequences should be used to provide enough statistical power.

In certain embodiments, when determining position-dependent or position-independent enrichment of window oligomers, the enrichment may be determined with respect to a set of background elements (also referred to herein as the "second set") that do not have (or are not predicted to have) the selected property. Generally, the second set of regulatory elements comprises all or the majority of the class of regulatory elements in an organism. In some embodiments, the second set can comprise from about 20,000 to 60,000 regulatory elements but in other embodiments the second set comprises a subset from the target organism. Typically, the second set comprises at least about 100 regulatory elements. In certain other embodiments, a "simulated background"

process is used as described herein, rendering this second set of elements unnecessary. The simulated background approach can be used, for example, in the design of virus promoters. Briefly, the simulated background method involves determining the position-dependent enrichment of the window oligomers in the first set of regulatory elements, with respect to the total occurrence of the window oligomer in the set of regulatory elements.

In certain embodiments, the methods construct a genetic regulatory element that can appear more than once in a gene of interest such as, for example, an intron. In such embodiments, the first set of genetic regulatory elements can comprise all introns that occur in a specified position (e.g., the first or last intron in a gene) and the second set of genetic regulatory elements can comprise all introns in the genome of the organism that fall outside of the specified position. In one embodiment of the invention, the first set of genetic regulatory elements comprise first introns from highly expressed constitutive genes that occur in either the 5' UTR or the coding region and within 500 base pairs (bp) of the transcription start site (TSS). The second set of nucleotide sequences then comprise all non-first introns of all genes in the target organism.

The set of regulatory elements are aligned around a conserved sequence or "landmark" sequence for position-dependent analysis of enriched sequences. The conserved sequence or landmark may be a transcription start site (TSS), a TATA box, a transcription termination signal, a polyadenylation signal, a splice acceptor site, a splice donor site, or a branch site. In certain embodiments, the conserved sequence is a TSS or TATA box. In some embodiments, the landmark sequence includes the 5' and/or 3' end of the element, or other a conserved motif or sub-element within the genetic element. However, any method of aligning the sequences known in the art can be used. For example, when the genetic regulatory element is an intron, intron sequences can be aligned on both 5' and 3' splice sites, and the middle sequence duplicated or truncated as needed to make them all the same length.

The transcription start sites (TSSs) annotated in public genome databases may not always be the most frequently used TSS in vivo; e.g. see, Troukhan et al. (2008) *OMICS* 13(2):139-151. However, many of the constitutive high-expressing genes (such as those of *Arabidopsis*) have a putative TATA box near their annotated TSS, and aligning this subset of promoters on their TATA box can improve the quality of the designed promoters. Alternately, databases of cDNAs and/or ESTs can be used to predict TSS positions, in the style of Troukhan et al. (2008) OMICS 13(2):139-151. Finally, TSSs can be mapped directly using RNA-seq based methods such as PEAT (Ni et al., 2010, Nature Methods 7:521-527), nanoCAGE and CAGEscan (Plessy et al., 2010, Nature Methods 7:528-534).

The methods involve selecting a word or window length to use in comparing the sequences. A "word" is short nucleotide sequence and "word length" is the number of contiguous nucleotides in a word. For a given application of the methods disclosed herein, the word length is fixed. The word length is typically about 4, 5, 6, 7, 8, 9, or 10. For each word length x, there are $4^x$ possible words, due to the possibility of an A, G, C, or T at each nucleotide position in a word, although all words might not be represented in the nucleotide sequences of a set of genetic regulatory elements.

In iteratively or non-iteratively modifying the nucleotide sequence to improve its score, any suitable method may be used. In some embodiments, a simulated annealing algorithm is employed. Other types of algorithms that can be used for this purpose include genetic algorithms, tabu search, simplex algorithm, steepest descent, conjugate gradients, and dynamic programming.

As disclosed in detail herein, the scoring function in some embodiments calculates a position-dependent and/or position independent score for a plurality of oligomer windows, and determines a probability that the nucleotide sequence will have the selected property based on an aggregate or factor of said position-dependent scores. The position-dependent enrichment of an oligomer window in the set of regulatory sequences with the selected property means that the oligomer sequence is enriched at the same position or a position defined as within ±200, or in some embodiments within ±100, or in some embodiments within ±30 nucleotides. In some embodiments, position-dependent enrichment is constrained to within +20 nucleotides or within ±10 nucleotides.

In various embodiments, only part of the nucleotide sequence is analyzed for position-dependent enrichment of the oligomer window, since the predicted importance of the positioning may depend on the type of element or vary within an element. For example, where the synthetic regulatory element is a promoter, the position-dependent enrichment of the windows may be less important at regions distant from the TSS or TATA box. Therefore, in some embodiments, the position-dependent enrichment of the windows may be determined in the set of regulatory elements with the selected property within at least the 20 bp region upstream and/or downstream from the TSS or TATA box. For example, relative to the TSS, a region comprising −50 to +20, or −100 to +20, or −200 to +20, or −50 to +50, or −100 to +50, or −200 to +50 may be analyzed for position-dependent enrichment of oligomer windows. In other embodiments, position-dependent enrichment is determined for at least about 50 bases, or at least about 100 bases upstream of the TSS or TATA Box. Other oligomer windows outside of these regions may be analyzed in a position-dependent or position-independent manner.

In some embodiments, the process maintains a level of sequence complexity or weights local sequence complexity such that the synthetic regulatory element approximates the sequence complexity (including locally in some embodiments) of the set of regulatory elements with the desired property. Sequence complexity can be defined by the GC or AT content, or defined by dinucleotide content (e.g., AA, AT, AC, AG, TT, TA, TC, TG, CC, CG, CT, CA, GG, GC, GA, and GT), or defined by the A, T, G, and/or C fractions. A separate score for local sequence complexity may be determined for various segments of the polynucleotide. Such segments may be at least 30 base pairs, and in some embodiments are at least 50 base pairs, or at least 100 base pairs, or at least 125 base pairs in length. In such embodiments, the invention employs an algorithm to calculate local sequence complexities, and the method thereby constrains local sequence complexity to approximate the local sequence complexity of the elements having the selected property.

In some embodiments, the synthetic regulatory element is a promoter and comprises a nucleotide sequence having at least 40%, at least 50%, at least 60%, at least 70%, at least 80%, or at least 90% sequence identity to SEQ ID NO: 1, 2, 3, 4, 5, 21, 22, 23, 24, 25, 26, 27, 28, or 29.

In some embodiments, the synthetic regulatory element is an expression-enhancing intron, and the synthetic regulatory element comprises a nucleotide sequence having at least 40%, at least 50%, at least 60%, at least 70%, at least 80%, or at least 90% sequence identity to SEQ ID NO: 6, 7, 8, 9, or 10.

In some embodiments, the synthetic regulatory element comprises a promoter and expression enhancing intron, and comprises a nucleotide sequence having at least 40%, at least 50%, at least 60%, at least 70%, at least 80%, or at least 90% sequence identity to SEQ ID NO: 15, 16, 17, 18, 19, or 20.

The methods disclosed herein for making synthetic regulatory elements are fundamentally different from previous approaches for designing synthetic regulatory elements. In the methods of the present invention, regulatory polynucleotide sequences are generated by a computational algorithm rather than by combining sequences from a defined group of sub-sequences (i.e., known cis-elements, consensus motifs, discrete n-mers, etc.). The algorithm can be probabilistic in nature and is used to design polynucleotide sequences to be similar to members of a set of naturally occurring sequences selected to share a known or predicted expression pattern; however, the designed sequences in most cases share little extended sequence homology with the naturally occurring sequences. The algorithm does not require predetermined knowledge of functional motifs, cis-elements, transcription factor binding sites, etc. Because of these characteristics, the computational methods described herein are widely applicable to both promoter and non-promoter regulatory elements, including, for example, introns and untranslated regions (UTRs), for which little or no functional motif information is available.

In certain embodiments, the method can be described by steps that comprise obtaining at least a first set of nucleotide sequences of a genetic regulatory element or part thereof, wherein the first set of nucleotide sequences is from a selected organism, and each of the genes in the first set of genes is known or expected to be expressed in a desired manner in the target organism. The methods then comprise determining for the first set of nucleotide sequences the frequency of each word of a pre-determined word length. As discussed, the word is a short nucleotide sequence, and the word length is the number of contiguous nucleotides in the short nucleotide sequence. Each word's position-dependent or position-independent enrichment may be determined as described herein. The methods further involve designing a synthetic genetic regulatory element or part thereof by starting from an initial nucleotide sequence and generating at least one related sequence that has an improved score with a scoring function. The initial nucleotide sequence, can for example, be a nucleotide sequence from the first set of nucleotide sequences or a sequence that is generated using a scoring function described below.

The score of a nucleotide sequence is derived from a scoring function reflecting the similarity of a nucleotide sequence to the first set of regulatory elements. The score is derived from the frequencies of the "words" in the first set of regulatory elements. Typically, the desired score is a score that is higher than the scores of about 1%, 5%, or 10% of the nucleotide sequences in the first set of regulatory elements. In some embodiments, the desired score is a score that is higher than the scores of about 20%, 25%, or 30% of the gene expression elements in the first set. In other embodiments, the desired score is a score that is higher than the scores of about 40%, 50%, 60% or more of the nucleotide sequences in the first set of nucleotide sequences. The methods of the invention can optionally involve generating one or more additional related sequences until a related sequence comprising a desired score is generated.

Figure 2:
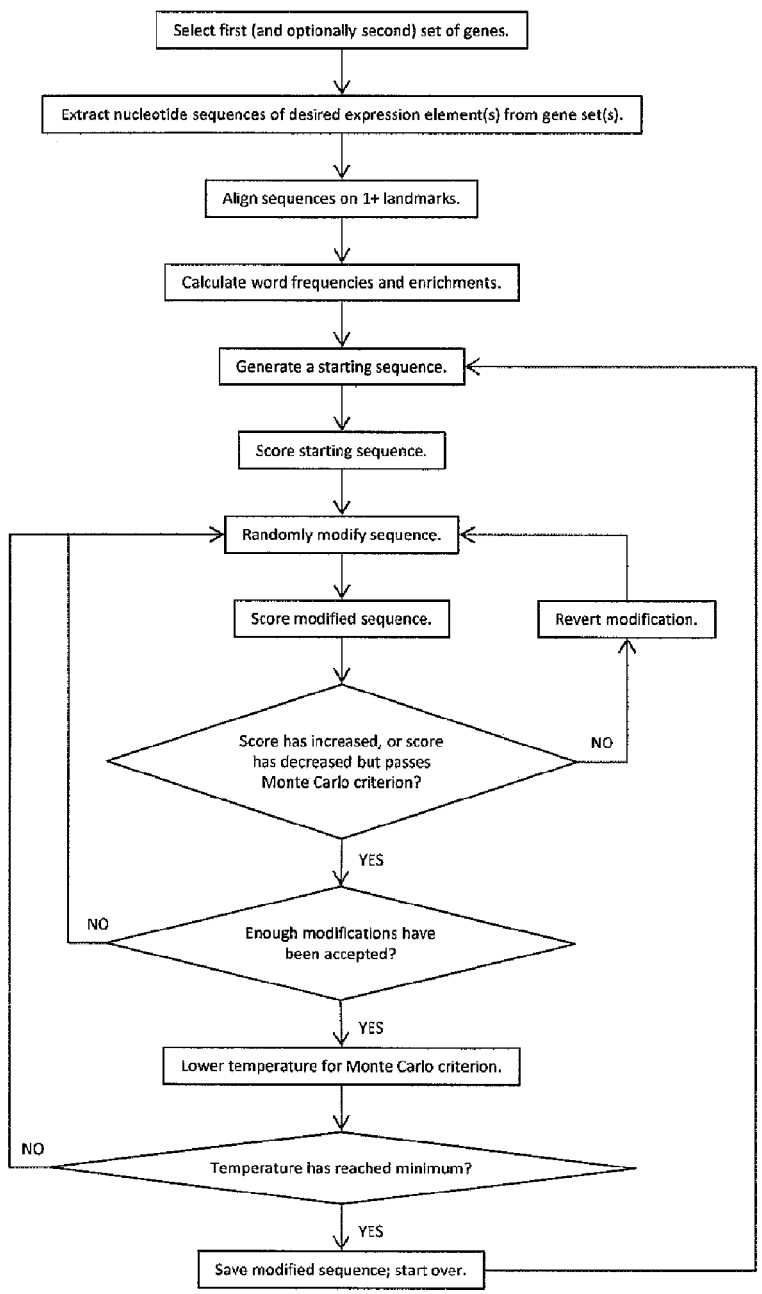
FIG. 2 is a flowchart depicting embodiments of the method for making a synthetic genetic regulatory element in accordance with the present invention.

Thus, as is described in further detail below, the methods in some embodiments can be further defined as determining: (i) the frequency of each word in a first set of genetic regulatory elements; (ii) the enrichment of each word in said genetic regulatory elements relative either to the occurrence of each word in a second set of genetic regulatory elements or to the frequency of the word over all positions in the first set of genetic regulatory elements (i.e., a second set of genetic regulatory elements is not used); and (iii) the sequence entropy of the genetic regulatory element. Typically, the methods of the present invention will involve a computer-implemented algorithm. FIGS. 1 and 2 are flowcharts that provide a non-limiting description of the steps in certain embodiments of the methods described herein.

Detailed embodiments of the computational method will now be described.

The nucleotide sequences from the first set (A) may be compared to those from a second background set (B) to determine what features of the genetic regulatory elements of A are likely to contribute to the distinctive expression pattern of those genes or elements. For example, the genetic regulatory element of interest may be a promoter. Promoters from A and B are aligned, i.e. relative to their TSSs, and the comparison may be performed in a position-specific manner, i.e., as a function of the distance from the TSS. As a variation, the sequences can be aligned around a conserved element near the TSS, such as, for example, the TATA box. Specifically, at each position, it is determined if the word or oligomer window sequences (also referred to herein as "k-mers", e.g., 4 to 10 consecutive bases) are overrepresented in the genes of interest.

The object is to produce a nucleotide sequence S that approximately maximizes the probability of expression pattern E, i.e., to (approximately) maximize P(E|S). For convenience, k is used to denote both the length of the short sequences (typically 4-10 bp) and the sequences themselves (e.g. GCCCA). Let G represent the union of sequence sets A and B. For each position i relative to the TSS, and each k-mer k, let $G_{k,i}$ be those sequences in G that contain k-mer k at position i. (The k-mer at i and the k-mer at i+1 overlap each other by k−1 bases.) Also, let Gi be those sequences in G that contain position i (as promoters differ in length, some G may be too short to contain a position i). Then the probability P(E|k,i) that a sequence having k-mer k at position i will display expression pattern E can be calculated by Bayes' rule:

$$P(E|i) = P(E) = \frac{\|A\|}{\|G\|}$$

$$P(k|i) = \frac{\|G_{k,i}\|}{\|G_i\|}$$

$$P(k|E, i) = \frac{\|A_{k,i}\|}{\|A_i\|}$$

$$P(E|k, i) = \frac{P(k|E, i)P(E|i)}{P(k|i)} = \frac{\frac{\|A_{k,i}\|}{\|A_i\|} \cdot \frac{\|A\|}{\|G\|}}{\frac{\|G_{k,i}\|}{\|G_i\|}} = \frac{\|A_{k,i}\|}{\|A_i\|} \cdot \frac{\|A\|}{\|G\|} \cdot \frac{\|G_i\|}{\|G_{k,i}\|}$$

The probability P(E|S) of sequence S giving expression pattern E can be estimated by assuming the position-wise probabilities are independent and multiplying them together. This procedure is thus very similar to a naïve Bayes classifier. These probabilities can be normalized by the base probability of expression pattern E and log-transform them, yielding a score $Z_1(S)$ that is greater than zero if sequence S is more likely than average to display pattern E, and less than zero if S is less likely than average to display pattern E:

$$Z_1(S) = \sum_{i \in S} \log \frac{P(E|k, i)}{P(E)} = \sum_{i \in S} \log\left(\frac{\|A_{k,i}\|}{\|A_i\|} \cdot \frac{\|G_i\|}{\|G_{k,i}\|}\right)$$

where k is understood to be $k_{S,i}$, the k-mer at position i of sequence S. Thus, the term inside the logarithm is merely the fold enrichment of k-mer k in the genes of interest compared to the genome as a whole. This can also be thought of as a log-odds score.

However, two problems arise due to the statistics of small numbers. First, longer k-mers are more informative, but there are typically many more possible k-mers than genes of interest, meaning $\|A_{k,i}\|$ is rarely greater than 1, and is often zero. For instance, there are 4096 possible 6-mers, and 65,536 possible 8-mers. Second, some k-mers are inherently uncommon in the genome, such that a very small number of occurrences in A leads to a spuriously high apparent enrichment.

The first problem can be corrected by counting occurrences of k over a local window, instead of just at position i. The count is done as a kernel density estimate with a cosine kernel, with half-width at half-height of w (w=10 base pairs in most cases, but w=5 and w=15 can also be used.).

$$\langle A_{k,i} \rangle = \frac{1}{2w} \sum_{j=i-2w}^{i+2w} \frac{\cos\left(\frac{\pi(i-j)}{2w}\right) + 1}{2} \|A_{k,j}\|$$

One skilled in the art will recognize that other kernels (e.g. Gaussian, triangular, square) or methods (e.g. standard, smoothed, or averaged-shifted histograms) may be used to achieve a similar result.

The second problem can be corrected by adding pseudo-counts ρ to the actual observations; this corresponds to presuming a uniform distribution as the Bayesian prior. For most of the embodiments disclosed herein, ρ=20 was used but values from 10 to 50 have also been used. With both changes and rearranging slightly, an improved score $Z_2(S)$ can be obtained:

$$Z_2(S) = \sum_{i \in S} \log \frac{P(E|k, i)}{P(E)} = \sum_{i \in S} \log\left(\frac{\|G_i\|}{\|A_i\|} \cdot \frac{\langle A_{k,i} \rangle + \frac{\|A_i\|}{\|G_i\|}\rho}{\langle G_{k,i} \rangle + \rho}\right)$$

However, in certain cases, a gene may contain the same k-mer many times in a small region; this is particularly severe in the case of long homopolymeric, dinucleotide, and trinucleotide repeats, because each k-mer overlaps the preceding one by (k−1) out of k bases. In these cases, as little as one gene with a long repeat may cause an apparent enrichment of a k-mer like "GGGGGG". This problem can be resolved by limiting the contribution to the k-mer count from each individual gene, while still smoothing counts over a local window:

$$\widehat{A_{k,i}} = \frac{1}{2w} \sum_{a \in A} \min\left(1, \sum_{j=i-2w}^{i+2w} \frac{\cos\left(\frac{\pi(i-j)}{2w}\right) + 1}{2} \|a_{k,j}\|\right)$$

where $\|\alpha_{k,j}\|=1$ if gene a contains k-mer k at position j, and 0 otherwise. This results in a further improved score $Z_3(S)$:

$$Z_3(S) = \sum_{i \in S} \log \frac{P(E|k, i)}{P(E)} = \sum_{i \in S} \log\left(\frac{\|G_i\|}{\|A_i\|} \cdot \frac{\widehat{A_{k,i}} + \frac{\|A_i\|}{\|G_i\|}\rho}{\widehat{G_{k,i}} + \rho}\right)$$

Promoter-like sequences that maximize $Z_3(S)$ should be likely to drive gene expression following pattern E. However, simply maximizing $Z_3$ does not guarantee that a sequence will be promoter-like: there may be certain features or properties that are common to all promoters, and $Z_3$ does not detect such features. In practice, a sequence that maximizes $Z_3$ will consist almost exclusively of k-mers that are actually observed with significant frequency in natural promoters, so this is not a major concern. However, it was observed that for some species (e.g. rice), a sequence designed to maximize $Z_3$ exhibits the same motifs over and over in close succession, resulting in unnaturally low complexity. To combat this effect, the local sequence entropy at each position along the designed sequence can be restrained. Local sequence entropy can be calculated using single nucleotides, dinucleotides, trinucleotides, and so forth. In a preferred embodiment of the invention, entropy is calculated using dinucleotide composition in a window of 2ω bases (2ω=128 bp):

$$H_{S,i} = \sum_{n \in \{AA,AC,AG,\ldots,TG,TT\}} \frac{\|S_n(i-\omega, i+\omega)\|}{2\omega} \log_2\left(\frac{\|S_n(i-\omega, i+\omega)\|}{2\omega}\right)$$

where $\|S_n(i-\omega,i+\omega)\|$ is the number of occurrences of dinucleotide n in sequence S between positions i−ω and i+ω. For comparison, mean local entropy $H_0$ and its variance $\sigma_{H0}^2$ can be calculated over all sequences and all positions in A. ($H_0 \cong 3.7$ and $\sigma_{H0}^2 \cong 0.03$) A score $Z_4(S)$ that imposes a harmonic penalty on S for excessively high or low local entropy can be defined:

$$Z_4(S) = \frac{-1}{2\sigma_{H0}^2} \sum_{i \in S} (H_{S,i} - H_0)^2$$

Furthermore, one skilled in the art will recognize that other measures of sequence complexity could be substituted for entropy, with similar results.

As indicated above, there are certain embodiments where it is beneficial to include motifs that are simply common in A, rather than particularly enriched relative to G. Empirically, this also helps to avoid unnaturally low complexity, particularly in the case of introns, where a few motifs are strongly enriched in a relatively position-independent manner. The motif frequency score is defined as:

$$Z_5(S) = \sum_{i \in S} \log\left(4^k \cdot \frac{\widehat{A_{k,i}} + 4^{-k}\rho}{\|A_i\| + \rho}\right)$$

where $\rho=1$ for all work to date. This score assumes all $4^k$ possible k-mers are equally likely a priori, i.e. the expected frequency of any given motif at any given position is $4^{-k}$; thus, $Z_5(S)$ is expected to be ~ zero for a random sequence. In some cases, this assumption can exaggerate in the designed sequences any imbalance of A/T vs. G/C content present in the naturally occurring sequences. In such a case, the expected frequency can instead be determined separately for each k-mer based on the fraction of A, C, G, and T bases in the naturally occurring sequences.

Finally, the position-dependent k-mer enrichment score can be combined with the entropy restraint and the frequency score to obtain a final, position-dependent scoring function Z(S). The components are weighted by empirically determined coefficients that balance k-mer composition with sequence complexity ($\varphi_z$=0.5 and $\varepsilon_z$=0.07 in most embodiments disclosed herein, although $\varphi_z$=5 and $\varepsilon_z$=150 may be preferred for certain embodiments where the genetic regulatory element is an intron):

$$Z(S)=Z_3(S)+\varepsilon_z Z_4(S)+\varphi_z Z_5(S)$$

It is expected that a promoter sequence S with a high value of Z(S) will confer a desired expression pattern on any gene of interest coupled to it. One skilled in the art will recognize that many methods may be used to generate a sequence S with a high values of Z(S). These methods include but are not limited to function optimization methods, such as simulated annealing, genetic algorithms, tabu search, simplex algorithm, steepest descent, conjugate gradients, and dynamic programming. Such methods may or may not incorporate an element of probability, randomness, or stochasticity; and may or may not involve an iterative process.

In a preferred embodiment of the invention, the "simulated annealing" method is used to iteratively improve the score of a starting sequence. Any sequence can be used as a starting point. For example one could use a member of set A or a randomly generated sequence. In a preferred embodiment, randomly selected k-mers are stitched together to form a full-length artificial promoter. Each k-mer is randomly selected with probability proportional to its frequency in A at the appropriate position i (that is, $\widehat{A_{k,t}}/\Sigma_k \widehat{A_{k,t}}$), without regard to frequency in the genome as a whole. In the method referred to herein as "simulated annealing", bases are then mutated at random, one at a time, and each change is accepted or rejected according to the Metropolis Monte Carlo criterion. If Z(S) increases, the change is always accepted; if Z(S) decreases, the change is accepted with probability $e^{\Delta Z(S)/T}$. To design one sequence, it has been determined to be generally sufficient to conduct 5,000 Monte Carlo trials for each temperature T E {2.0, 1.0, 0.5, 0.2, 0.1, 0.01} (30,000 total trials), in descending order, which takes about three minutes on a typical personal computer.

In some embodiments, promoters are designed based on viral promoters in the same family as 35S (Caulimoviridae). In this case, there is no obvious out-group (B) against which to contrast the sequences. In such cases, a "simulated" background can be calculated, contrasting the frequency of a motif at a particular position in A against its average frequency across all positions in A and is defined as follows:

$$Z'_3(S) = \sum_{i \in S} \log \left( \frac{\sum_{j \in S}\|A_j\|}{\|A_i\|} \cdot \frac{\widehat{A_{k,t}} + \frac{\|A_i\|}{\sum_{j \in S}\|A_j\|}\rho}{\sum_{j \in S}\|A_{k,j}\| + \rho} \right)$$

and use this instead of $Z_3(S)$ to calculate Z(S). In certain embodiments of the invention, the "simulated background" method is applied even when there is an obvious out-group B.

In certain embodiments, including those involving genetic regulatory elements that are viral promoters, the TSS may be unknown. In such embodiments where the TSS is unknown or even in embodiments where the TSS is known, the promoters can be aligned on their TATA boxes instead. For viral promoters, for example, some signals (e.g., the TATA boxes) are so much stronger than others that it becomes difficult to choose a suitable bandwidth w for the kernel density estimation step: too little smoothing makes it difficult to detect more dispersed signals, but too much smoothing leads to tandem repeats of strong motifs like the TATA box. Thus, standard kernel density estimation can be replaced with an adaptive variant, such as that described by Van Kerm ((2003) "*Adaptive kernel density estimation*", 9th UK Stata Users meeting, Royal Statistical Society, London, May 19-20, 2003). The bandwidth is varied per motif and per position, based on the local density: weak signals are smoothed more, strong signals are smoothed less. This is expensive to compute for a large background set, and so fits particularly well with the "simulated background" approach, where only a small group of sequences needs to be processed. Alternately, adaptive KDE can be used for the in-group and fixed-bandwidth KDE can be used for the out-group, because the out-group is highly heterogeneous, and so no sharp peaks are expected (with the possible exception of the TATA box).

Due to the form of the scoring function, it is straight forward to use a weighted combination (min, max, sum, etc.) of such scoring functions. The component functions might be trained on different k-mer lengths or gap structures, or might be trained on different data sets. For example, a scoring function derived from genes that are highly expressed in roots might be combined with a function derived from genes that are highly expressed in shoots, leading to designs that should be highly expressed in both roots and shoots.

In certain embodiments of the invention, multiple scoring functions are combined so as to retain the most informative parts of each. For each k-mer and position, either the value of the most significant scoring function is used, or if no scoring function is significant, all are averaged.

In certain embodiments, a position-independent approach can be used to design synthetic genetic regulatory elements or portions thereof. In other embodiments, a hybrid approach can be used where the position-dependent approach described above is employed to design a first part of the nucleotide sequence of a synthetic regulatory element and a position-independent approach is employed to design a second part of the synthetic regulatory element.

The position-independent approach was based on observations made concerning promoters. However, the methods of the invention are not limited to promoters but can be used with any genetic regulatory element. For promoters, it was observed that the most significant position-specific enrichments of k-mers in promoters can occur in the approximately 200 bases prior to the TSS. Further upstream of the TSS, enrichment signals were generally weak and can be unreliable. This is consistent with the understanding in the field that there are highly position-sensitive "core promoter" elements near the TSS, and less position-specific enhancing or regulatory elements further from the TSS. Therefore, hybrid synthetic promoters were designed which optimize Z(S) in the core promoter region (about −200 to +50) and an alternative score in the upstream regulatory region (about −500 to −200). A 300 bp regulatory region was selected for experimental testing based on the sizes of naturally occurring *Arabidopsis* promoters, but longer or shorter regions are likely to function similarly.

In upstream regulatory regions, it is assumed that the exact position and strand of sequences are of little importance; therefore, the prevalence of short k-mers is analyzed over the entire length of the promoters. Given genes of interest A out of the genome G, we can simply count how many contain one or more copies of k-mer k, denoting those sets $A_k$ and $G_k$ respectively. Alternately, the total number of occurrences of k can be counted without regard to how many (or few) genes they are spread among: let there be $\alpha_k$ total occurrences of k in the genes of A, and $\gamma_k$ in G. Because there are more counts in the position-independent case than the position-dependent case, and because the counts are whole numbers, the degree of over- or under-representation of k in A is assessed via a one-tailed binomial test. The binomial test models sampling with replacement. The hypergeometric test, which models sampling without replacement, might be more statistically appropriate, but in this situation the probability estimates from the two methods are very similar, and the binomial test has other advantages described below. That is, $$q_1(k) = lpbinom\left(\|A_k\|, \|A\|, \frac{\|G_k\|}{\|G\|}\right)$$

$$q_2(k) = lpbinom\left(\alpha_k, \sum_m \alpha_m, \frac{\gamma_k}{\sum_m \gamma_m}\right)$$

$$lpbinom(x, n, p) = minabs\left(\begin{array}{c} \log \sum_{m=1}^{x} \binom{n}{m} p^m (1-p)^{n-m}, \\ -\log \sum_{m=x}^{n} \binom{n}{m} p^m (1-p)^{n-m} \end{array}\right)$$

$$minabs(a, b) = \begin{cases} a, \text{ if } |a| < |b| \\ b, \text{ otherwise} \end{cases}$$

In some embodiments of the present invention, the "binned enrichment" correction described in Linhart et al. (Genome Research, 2008, 18:1180-1189) can be used. Instead of estimating the probability of observing k-mer k as $$\frac{\|G_k\|}{\|G\|},$$

the method of Linhart et al. divides the genes into n groups by GC content and/or length, and estimates the revised probability depending on how the genes of A partition into those groups:

$$\sum_{i=1}^{n} \frac{\|A_i\|}{\|A\|} \frac{\|G_{k,i}\|}{\|G_i\|}$$

As long as the number of groups is relatively small (n~10), the probability estimates $$\frac{\|G_{k,i}\|}{\|G_i\|}$$

are still quite stable. Partitioning by GC content is particularly helpful when studying gene populations that are notably AT- or GC-rich compared to the genome as a whole.

As a further refinement, some sets of sequences are enriched in a single nucleotide, or other distributions that don't map to the AT/GC split. For these cases, the input sequences can be clustered into a small number of disjoint clusters based on their composition, e.g. by k-means clustering on features {% A, % C, % G, % T}. The corrected enrichment calculation then proceeds as above.

Rather than using an in-group and an out-group, one may be able to identify functional k-mers by looking at their conservation between in-group sequences in a species of interest and orthologous sequences in related species. The binomial test is used in an analogous manner, but the expected probability is calculated from the frequency of each k-mer in the relevant sequence-sets for each organism under consideration. Conservation evidence could be combined with in-group/out-group analysis, perhaps by converting the p-values to Z-scores and adding them (Stouffer's Method).

As a third alternative, expected probabilities (i.e., frequencies) of the various k-mers in the in-group can be computed from an nth-order Markov model of the in-group sequences (n<k). Again the binomial distribution is used to assess the p-value of the actual frequency of occurrence vs. the computed expected probability, and again this type of scoring could be combined with the others.

Scores $q_1$ and $q_2$ could be used in multiple ways: use one or the other exclusively, take the more or less extreme of the two values for each k-mer, or take a (weighted) sum of the two scores. For the examples disclosed here, the more conservative of the two p-values was used:

$$q(k) = minabs(q_1(k), q_2(k))$$

Reports in the literature and anecdotal experience suggest that multiple occurrences of the same motif can increase promoter strength. However, designing a sequence solely to maximize q(k) is likely to lead to a very small number of distinct k-mers repeated many, many times. As a compromise, we decided to score sequences by awarding diminishing returns for multiple occurrences:

$$Q_1(S) = \sum_{k \in S} \log(1 + \|S_k\|) \cdot q(k)$$

where $\|S_k\|$ is the number of times k-mer k occurs in sequence S.

Although sequences designed to optimize $Q_1(S)$ do contain a good variety of k-mers, they do not generally reflect the GC-content of natural promoters. Thus, a harmonic restraint on sequence GC-content can be added:

$$Q_2(S) = \log(1 + \|S\|) \frac{-(c_S - c_0)^2}{2\sigma_{c0}^2}$$

where $\|S\|$ is the length of S in base pairs, $c_S \in [0,1]$ is the GC-content of S, and $c_0$ and $\sigma_{c0}^2$ are the mean and variance of GC-content of the genes in A.

Analogously to the derivation Z(S), we combine the position-independent k-mer score with the GC-content restraint to obtain a final, position-independent scoring function Q(S). The components are weighted by an empirically determined coefficient that balances k-mer composition with sequence GC content ($\varepsilon_Q$=20 in this work):

$$Q(S)=Q_1(S)+\varepsilon_Q Q_2(S)$$

It is expected that a promoter sequence S with a high value of Q(S) in the upstream regulatory region will confer our target expression pattern on any gene coupled to it. To design such a sequence, a procedure closely analogous to that for position-dependent design may be followed. Again, any method may be used to generate a sequence S with a high value of Q(S). In a certain embodiments of the invention, the simulated annealing method is used to iteratively improve the score of a starting sequence. Any sequence can be used as a starting point. For example one could use a member of set A or a randomly generated sequence. In a preferred embodiment of the invention, we begin by stitching together randomly selected k-mers to form a full-length artificial promoter. In some embodiments, 1050 bp sequences, from −1000 bp to +50 bp are used. Each k-mer is randomly selected with probability proportional to its overall frequency in A (that is, $\alpha_k/\Sigma_k\alpha_k$), without regard to position or to frequency in the genome as a whole. In the simulated annealing method, bases are then mutated at random, one at a time, and each change is accepted or rejected according to the Metropolis Monte Carlo criterion. If Q(S) increases, the change is always accepted; if Q(S) decreases, the change is accepted with probability $e^{\Delta Q(S)/T}$. To design one sequence, it has been determined to be generally sufficient to conduct 10,000 Monte Carlo trials for each temperature T∈{2.0, 1.0, 0.5, 0.2, 0.1, 0.01} in descending order (60,000 total trials). Sequences designed by this procedure are not expected to function as promoters on their own, and so must be placed upstream of a (designed or natural) sequence with core promoter activity.

In some embodiments of the present invention, specific elements or consensus sites of known functional importance can be added to the designed sequences. Such elements or consensus sites include, but are not limited to, intron splice sites, intron branch points, TATA sequences, transcription factor binding sites, chromatin control sequences, consensus sequences in the 5'-untranslated region (e.g. Kozak sequences), and consensus sites in the 3'-untranslated region (polyadenylation signal).

The synthetic regulatory elements are not natural, in that they are not known to occur in nature. In some embodiments, their nucleotide sequences shares little or no extended homology to natural sequences. Extended homology in this context generally refers to 100% sequence identity extending beyond about 25 nucleotides of contiguous sequence. The synthetic regulatory element prepared according to the methods described herein may have no significant identity to a member of the set of regulatory sequences having the selected gene expression property in the target cell or organism. In some embodiments, the nucleotide sequence does not have significant level of homology to any natural regulatory sequence. For example, the level of homology, over the entire designed sequence (or the highest local alignment in some embodiments, e.g., using BLAST) may be lower than about 60%, 50%, 40%, 30% 25%, or 20% when aligned with any member of the set of regulatory elements with the selected gene expression property.

The determination of percent identity between two sequences can be accomplished using a mathematical algorithm. In some embodiments, a mathematical algorithm utilized for the comparison of two sequences is the algorithm of Karlin and Altschul (1990) *PNAS* 87:2264, modified as in Karlin and Altschul (1993) *PNAS* 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to determine levels of homology or identity. Sequence identity values for pairs of sequences may be obtained using the BLAST 2.0 suite of programs using default parameters (Altschul et al., (1997) *Nucleic Acids Res.* 25:3389-402). Sequence identity values for multiple sequence alignments can be obtained using MUSCLE (Version 3.8) using default parameters. See, Edgar (2004) *Nucleic Acids Res.* 32 (5): 1792-1797; herein incorporated by reference.

The synthetic regulatory elements in accordance with the invention are not restricted to any particular size, but in some embodiments the sequences generated or operatively connected to genes of interest are at least 25 nucleotides, at least about 30 nucleotides, at least about 40 nucleotides, at least about 50 nucleotides, at least about 60 nucleotides, at least about 70 nucleotides, at least about 80 nucleotides, at least about 90 nucleotides, at least about 100 nucleotides, at least about 150 nucleotides, at least about 200 nucleotides, at least about 250 nucleotides, at least about 300 nucleotides, at least about 350 nucleotides, at least about 400 nucleotides, at least about 450 nucleotides, at least about 500 nucleotides, at least about 550 nucleotides, at least about 600 nucleotides, or at least about 1 kb in length.

The present invention can relate to a computer system or computer-implemented product to carry out the methods described herein. In general, the system includes a source of data (e.g., databases generated or made, or link to an external database), such as nucleotide sequence and/or gene expression data. A computer system can embody a software program or processor routine to process the data by performing the position-dependent or position-independent analysis described in detail herein. The computer system employs a host processor in which the operation of software programs is executed. The software provides an output for either memory storage or to an output device. The computer system can employ a network connection. The network can be any network or combination of networks that can carry data communications. Such network can include, but is not limited to, a local area network, medium area network, and/or wide area network such as the internet. The network can support protocols and technology including, but not limited to, World Wide Web protocols and/or services. The system may be implemented as a computer, workstation, distributed computing system, embedded system, standalone electronic device, networked device, mobile device, display device, or other type of processor or computer system. When implemented as a device or as software in the device connected to other components via the network, such device implementing the output module is referred to as a "remote client." Likewise, the entire system can be implemented in software, firmware, hardware, or any combination thereof. Furthermore, the system can be used as a standalone system or in connection with a search engine, web portal, web site, or any other applications capable of presenting sequence information for analysis.

In certain embodiments, the methods further comprise synthesizing a nucleic acid molecule comprising the synthetic nucleotide sequence and/or testing the synthetic genetic regulatory element to determine if the synthetic genetic regulatory element is capable of regulating gene expression in the desired manner. An additional selection step can be employed to determine if the synthetic nucleotide sequence that was selected on the basis of its score is capable of regulating the expression of an operably linked gene of interest in the desired manner and/or in the desired cell or organism. As used herein, the term "operably linked" refers to the association of nucleic acid sequences so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

In certain embodiments, synthetic sequences designed in accordance with the invention can be incorporated into polynucleotides containing coding sequences or expressed non-coding sequences with other wildtype regulatory sequences. For example, a synthetic regulatory element comprising a promoter may be produced, and incorporated into a polynucleotide comprising a naturally-occurring intron. In some embodiments, a synthetic regulatory element comprising an intron may be produced, and incorporated into a polynucleotide comprising a naturally-occurring promoter.

Typically the function of the genetic regulatory elements are determined by transforming the organism or at least one cell thereof with a polynucleotide construct comprising the genetic regulatory element operably linked to the gene of interest. The polynucleotide construct can further comprise additional genetic regulatory elements, if desired or necessary for expression in the gene of interest in the organism or at least one cell thereof. Those of skill in the art will appreciate that determining whether the genetic regulatory element is capable of regulating the expression of an operably linked gene in the desired manner in the target organism or any other organism of interest can depend on any number of factors including, for example, the type of genetic regulatory element produced by the methods disclosed herein, the presence of additional genetic elements in the expression construct, the gene of interest to be expressed, the organism or part or cell thereof in which expression is assayed, the expression assay, the detection method (e.g., GFP visible fluorescent, detection of GFP RNA by qPCR), the environmental conditions during the assay, and the like.

For example, in certain embodiments in which the genetic regulatory element is a promoter and expression of the gene of interest is evaluated by expression of the encoded protein, about 5-15% of the genetic regulatory elements produced by the methods of the present invention may display expression detectable by confocal imaging of GFP fluorescence in *Arabidopsis thaliana* in the T1 generation in the absence of an enhancing intron in the polynucleotide construct. However, when the polynucleotide construct further comprises an enhancing intron about 60% of the genetic regulatory elements display detectable expression by confocal imaging of GFP fluorescence in the T1 generation, when assayed in *Arabidopsis thaliana* by the methods disclosed herein below. Similarly, when promoter activity is determined at the nucleic acid level, i.e. by sensitive qPCR detection, about 60% of the genetic regulatory elements display detectable promoter activity without the addition of an enhancing intron. These results indicate that the majority of synthetic promoters produced by the methods in the present invention have biological promoter activity in plants.

In determining whether the genetic regulatory element is capable of regulating the expression of an operably linked gene in the desired manner, a reporter gene may be employed. As used herein a "reporter" or a "reporter gene" refers to a nucleic acid molecule encoding a detectable marker. Preferred reporter genes include, for example, luciferase (e.g., firefly luciferase or *Renilla* luciferase), β-galactosidase, chloramphenicol acetyl transferase (CAT), and a fluorescent protein (e.g., green fluorescent protein (GFP), red fluorescent protein (DsRed), yellow fluorescent protein, blue fluorescent protein, cyan fluorescent protein, or variants thereof, including enhanced variants such as enhanced GFP (eGFP). Reporter genes are detectable by a reporter assay. Reporter assays can measure the level of reporter gene expression or activity by any number of means, including, for example, measuring the level of reporter mRNA, the level of reporter protein, or the amount of reporter protein activity. Reporter assays are known in the art or otherwise disclosed herein.

The genetic regulatory elements that are produced by the methods as disclosed herein are not limited to use in the target organism from which the one or more sets of genes as described herein were derived. In one example, a genetic regulatory element that is produced by the methods of the present invention using a first set of nucleotide sequences of a genetic regulatory element from *Arabidopsis thaliana* finds use in regulating the expression of an operably linked gene of interest in an *Arabidopsis thaliana* plant, a soybean plant, and/or in one or more other dicotyledonous plants of interest. In another example, a genetic regulatory element that is produced by the methods of the present invention using a first set of nucleotide sequences of a genetic regulatory element from rice finds use in regulating the expression of an operably linked gene of interest in a rice plant, a maize plant, and/or in one or more other monocotyledonous plants of interest. In yet another example, a genetic regulatory element that is produced by the methods of the present invention using a first set of nucleotide sequences of a genetic regulatory element from Caulimoviridae viruses finds use in regulating the expression of an operably linked gene of interest in an *Arabidopsis thaliana* plant, a soybean plant, a rice plant, a maize plant, and/or in one or more other monocotyledonous and/or dicotyledonous plants of interest. In still another example, a genetic regulatory element that is produced by the methods of the present invention using a first set of nucleotide sequences of a genetic regulatory element from *Mus musculus* finds use in regulating the expression of an operably linked gene of interest in *Homo sapiens* or cell thereof, and/or in one or more other mammals of interest or cell thereof.

In some embodiments, the synthetic regulatory element is a promoter. "Promoter" refers to a nucleic acid that is capable of controlling the expression of an operably linked coding sequence or other sequence encoding an RNA that is not necessarily translated into a protein. The promoter sequence can comprise proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, nucleic acid fragments of some variation may have identical promoter activity.

Promoters that cause a gene to be expressed in most cell types of an organism and at most times are commonly referred to as "constitutive promoters." Expression of a gene in most cell types of an organism and at most times is referred to herein as "constitutive gene expression" or "constitutive expression."

In some embodiments, the promoter is a plant promoter. A "plant promoter" is a promoter capable of initiating transcription in plant cells whether or not its origin is a plant cell. For example, it is well known that *Agrobacterium* promoters are functional in plant cells. Thus, plant promoters include promoter DNA obtained from plants, plant viruses and bacteria such as *Agrobacterium* and *Bradyrhizobium* bacteria, and synthetic promoters capable of initiating transcription in plant cells. A plant promoter can be a constitutive promoter, a non-constitutive promoter, an inducible promoter, a repressible promoter, a tissue specific promoter (e.g., a root specific promoter, a stem specific promoter, a leaf specific promoter), a tissue preferred promoter (e.g., a root preferred promoter, a stem preferred promoter, a leaf preferred promoter), a cell type specific or preferred promoter (e.g., a meristem cell specific/preferred promoter), or any other type.

A constitutive promoter is a promoter which is active under most conditions and/or during most development stages. There are several advantages to using constitutive promoters in expression vectors used in plant biotechnology, such as: high level of production of proteins used to select transgenic cells or plants; high level of expression of reporter proteins or scorable markers, allowing easy detection and quantification; high level of production of a transcription factor that is part of a regulatory transcription system; production of compounds that requires ubiquitous activity in the plant; and production of compounds that are required during all stages of plant development. For illustration, constitutive promoters include, CaMV 35S promoter, opine promoters, ubiquitin promoter, actin promoter, alcohol dehydrogenase promoter, etc. In some embodiments, the synthetic promoter prepared as described herein, is used to drive expression of a heterologous sequence, while CaMV 35S promoter is used to drive expression of a second sequence.

A non-constitutive promoter is a promoter which is active under certain conditions, in certain types of cells, and/or during certain development stages. For example, tissue specific or preferred, cell type specific or preferred, inducible promoters, and promoters under developmental control are non-constitutive promoters. Examples of promoters under developmental control include promoters that preferentially initiate transcription in certain tissues, such as stems, leaves, roots, or seeds.

An "inducible" or "repressible" promoter is a promoter which is under chemical or environmental factor control. Examples of environmental conditions that may affect transcription by inducible promoters include cold, heat, drought, light, or certain chemicals.

A "tissue specific" promoter is a promoter that initiates transcription only in certain tissues. Unlike constitutive expression of genes, tissue-specific expression is the result of several interacting levels of gene regulation. As such, sometimes it is preferable to use promoters from homologous or closely related plant species to achieve efficient and reliable expression of transgenes in particular tissues. This is one of the main reasons for the large amount of tissue-specific promoters isolated from particular plants and tissues found in both scientific and patent literature. Non-limiting tissue specific promoters include, beta-amylase gene or barley hordein gene promoters (for seed gene expression), tomato pz7 and pz130 gene promoters (for ovary gene expression), tobacco RD2 gene promoter (for root gene expression), banana TRX promoter and melon actin promoter (for fruit gene expression), and embryo specific promoters, e.g., a promoter associated with an amino acid permease gene (AAPl), an oleate 12-hydroxylase: desaturase gene from *Lesquerella fendleri* (LFAH12), an 2S2 albumin gene (2S2), a fatty acid elongase gene (FAEl), or a leafy cotyledon gene (LEC2). For example, a "root specific" promoter is a promoter that initiates transcription only in root tissues.

A "tissue preferred" promoter is a promoter that initiates transcription mostly, but not necessarily entirely or solely in certain tissues. For example, a "root preferred" promoter is a promoter that initiates transcription mostly, but not necessarily entirely or solely in root tissues.

A "cell type specific" promoter is a promoter that primarily drives expression in certain cell types in one or more organs, for example, vascular cells in roots, leaves, stalk cells, and stem cells.

A "cell type preferred" promoter is a promoter that primarily drives expression mostly, but not necessarily entirely or solely in certain cell types in one or more organs, for example, vascular cells in roots, leaves, stalk cells, or stem cells.

In some embodiments, the synthetic regulatory element is an expression-enhancing intron. An "expression-enhancing intron" or "enhancing intron" is an intron that is capable of causing an increase in the expression of a gene to which it is operably linked. While the present invention is not considered to depend on a particular biological mechanism, it is believed that the expression-enhancing introns of the present invention enhance expression through intron mediated enhancement (IME). It is recognized that naturally occurring introns that enhance expression through IME are typically found within 1 Kb of the transcription start site of their native genes (see, Rose et al. (2008) *Plant Cell* 20:543-551). Such introns are usually the first intron, whether the first intron is in the 5' UTR or the coding sequence, and need to be in a transcribed region. Introns that enhance expression solely through IME do not enhance gene expression when they are inserted into a non-transcribed region of gene, such as for example, a promoter. That is, they do not function as transcriptional enhancers. Unless stated otherwise or apparent from the context, the expression-enhancing introns of the present invention are capable of enhancing gene expression when they are found in a transcribed region of a gene but not when they occur in a non-transcribed region such as, for example, a promoter.

In other aspects, the invention provides a method for making expression vectors, transgenic cells, or non-human transgenic organisms, using the methods described herein for producing synthetic regulatory elements. The methods involve operably linking a synthetic regulatory element of the present invention to a gene of interest so as to produce an expression construct. Such genes of interest will depend on the desired outcome and can comprise nucleotide sequences that encode proteins and/or RNAs of interest. Nucleic acid molecules can be synthesized or produced using a number of methods known in the art. These include chemical synthesis and recombinant techniques. The methods further involve transforming at least one cell with the polynucleotide construct. The methods can additionally involve propagating the cell or regenerating a transgenic organism from the transformed cell.

As used herein, the phrases "recombinant construct", "expression construct", "chimeric construct", "construct", and "recombinant DNA construct" are used interchangeably. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. Screening transformants may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating.

The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide to be under the transcriptional regulation of the regulatory regions.

Where appropriate, the genes of interest may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, sulfonylurea, glyphosate, glufosinate, L-phosphinothricin, triazine, benzonitrile and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng.* 85:610-9 and Fetter et al. (2004) *Plant Cell* 16:215-28, cyan florescent protein (CYP) (Bolte et al. (2004) *J. Cell Science* 117:943-54 and Kato et al. (2002) *Plant Physiol.* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *PNAS* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) Cell 49:603-612; Figge et al. (1988) Cell 52:713-722; Deuschle et al. (1989) *PNAS* 86:5400-5404; Fuerst et al. (1989) *PNAS* 86:2549-2553; Deuschle et al. (1990) *Science* 248:480-483; Gossen (1993) Ph.D. Thesis, University of Heidelberg; Reines et al. (1993) *PNAS* 90:1917-1921; Labow et al. (1990) *Mol. Cell. Biol.* 10:3343-3356; Zambretti et al. (1992) *PNAS* 89:3952-3956; Baim et al. (1991) *PNAS* 88:5072-5076; Wyborski et al. (1991) Nucleic Acids Res. 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschmidt et al. (1988) *Biochemistry* 27:1094-1104; Bonin (1993) Ph.D. Thesis, University of Heidelberg; Gossen et al. (1992) *PNAS* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

In certain aspects, the invention provides a method for making a transgenic cell or non-human organism, by incorporating a synthetic regulatory element in operable association with a coding sequence or other transcribed gene into one or more cells, where the synthetic regulatory element has a statistically significant score with the scoring function described herein. The cells are propagated to make the transgenic cell or non-human organism. It is recognized that the genetic regulatory elements of the present invention and expression cassettes comprising one or more of such genetic regulatory elements can be used for the expression in both human and non-human host cells including, but not limited to, host cells from plants, animals, fungi, and algae. In one embodiment of the invention, the host cells are human host cells or a host cell line that is incapable of differentiating into a human being.

The methods of the invention involve introducing a polynucleotide construct into a plant. The term "introducing" means presenting to the plant the polynucleotide construct in such a manner that the construct gains access to the interior of a cell of the plant. The methods of the invention do not depend on a particular method for introducing a polynucleotide construct to a plant, only that the polynucleotide construct gains access to the interior of at least one cell of the plant. Methods for introducing polynucleotide constructs into plants are known in the art including, but not limited to, stable transformation methods, transient transformation methods, and virus-mediated methods. The transformation may be stable or transient.

By "stable transformation" is intended that the polynucleotide construct introduced into a plant integrates into the genome of the plant and is capable of being inherited by progeny thereof. By "transient transformation" is intended that a polynucleotide construct introduced into a plant does not integrate into the genome of the plant.

Suitable methods of introducing nucleotide sequences into plant cells and subsequent insertion into the plant genome include microinjection as Crossway et al. (1986) *Biotechniques* 4:320-334, electroporation as described by Riggs et al. (1986) *PNAS* 83:5602-5606, Agrobacterium-mediated transformation as described by Townsend et al., U.S. Pat. No. 5,563,055, Zhao et al., U.S. Pat. No. 5,981,840, Yukou et al., WO 94/000977, and Hideaki et al., WO 95/06722, direct gene transfer as described by Paszkowski et al. (1984) *EMBO J.* 3:2717-2722, and ballistic particle acceleration as described in, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); Datta et al. (1990) *Biotechnology* 8:736-740 (rice); Klein et al. (1988) *PNAS* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *PNAS* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The polynucleotides of the invention may be introduced into plants by contacting plants with a virus or viral nucleic acids. Generally, such methods involve incorporating a polynucleotide construct of the invention within a viral DNA or RNA molecule. Further, it is recognized that promoters of the invention also encompass promoters utilized for transcription by viral RNA polymerases.

The cells that have been transformed may be grown into plants in accordance with conventional techniques. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruits, roots, root tips, anthers, and the like. Progeny, variants, and mutants of the regenerated plants are also included within the scope of the invention, provided that these parts comprise the introduced polynucleotides (e.g., comprising the synthetic regulatory element).

With respect particularly to plants, genes of interest that are controlled by the synthetic regulatory element are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, yield, abiotic stress tolerance, and commercial products. Genes of interest include, generally, those involved in oil, starch, carbohydrate, or nutrient metabolism. In addition, genes of interest include genes encoding enzymes and other proteins from plants and other sources including prokaryotes and other eukaryotes.

In certain embodiments, the invention relates to transgenic plants and methods for making the same. As used herein, the term "plant" refers to any living organism belonging to the kingdom Plantae (i.e., any genus/species in the Plant Kingdom). In some embodiments, the plant is a tree, herb, bush, grass, vine, fern, moss, or green algae. The plant may be monocotyledonous (monocot) or dicotyledonous (dicot). Examples of particular plants include but are not limited to *Arabidopsis, Brachypodium*, switchgrass, corn, potato, rose, apple tree, sunflower, wheat, rice, banana, tomato, opo, pumpkin, squash, lettuce, cabbage, oak tree, *Guzmania, geranium, hibiscus, clematis, Poinsettia*, sugarcane, taro, duck weed, pine tree, Kentucky blue grass, *zoysia*, coconut tree, cauliflower, cavalo, collard, kale, kohlrabi, mustard greens, rape greens, and other *brassica* leafy vegetable crops, bulb vegetables (e.g. garlic, leek, onion (dry bulb, green, and Welch), shallot), citrus fruits (e.g. grapefruit, lemon, lime, orange, tangerine, citrus hybrids, pummelo, and other citrus fruit crops), cucurbit vegetables (e.g. cucumber, citron melon, edible gourds, gherkin, muskmelons (including hybrids and/or cultivars of *cucumis* melons), water-melon, cantaloupe), fruiting vegetables (including eggplant, ground cherry, pepino, pepper, tomato, tomatillo), grape, leafy vegetables (e.g. romaine), root/tuber and corm vegetables (e.g. potato), and tree nuts (almond, pecan, pistachio, and walnut), berries (e.g., tomatoes, barberries, currants, elderberries, gooseberries, honeysuckles, mayapples, nannyberries, Oregon-grapes, see-buckthorns, hackberries, bearberries, lingonberries, strawberries, sea grapes, lackberries, cloudberries, loganberries, raspberries, salmonberries, thimbleberries, and wineberries), cereal crops (e.g., corn (maize), rice, wheat, barley, sorghum, millets, oats, ryes, triticales, buckwheats, fonio, *quinoa*, oil palm), Brassicaceae family plants, and Fabaceae family plants, pome fruit (e.g., apples, pears), stone fruits (e.g., coffees, jujubes, mangos, olives, coconuts, oil palms, pistachios, almonds, apricots, cherries, damsons, nectarines, peaches and plums), vine (e.g., table grapes, wine grapes), fiber crops (e.g. hemp, cotton), ornamentals, and the like.

In some embodiments, the transgenic plant is of the Brassicaceae family. As used herein, Brassicaceae family refers to the plant family which is also known as the Cruiferae. The family contains over 330 genera and about 3700 species. Non-limiting examples of plants in this family include cabbage, broccoli, cauliflower, turnip, rapeseed, mustard, radish, horseradish, cress, wasabi, and watercress. Non-limiting examples of Brassicaceae plants include *Brassica oleracea* (broccoli, cabbage, cauliflower, etc.), *Brassica rapa* (turnip, Chinese cabbage, etc.), *Brassica napus* (rapeseed, etc.), *Raphanus sativus* (common radish), *Armoracia rusticana* (horseradish), *Matthiola* (stock), *Arabidopsis thaliana* (model organism), mustard, cress, wasabi, watercress and many others.

To introduce the nucleic acid molecules in *Brassica* species, nucleic acid molecules are cloned into a binary vector suitable for *Brassica* species transformation, such as the vectors described by Bhalla et al., 2008 (*Agrobacterium*-mediated transformation of *Brassica napus* and *Brassica oleracea*, Nature Protocols, 3:181-189) or similar ones.

In some embodiments, the transgenic plant is of the *Triticum* genus. *Triticum* species include *T. aestivum* (e.g., common wheat, or bread wheat, a.k.a. *Triticum aestivum* L. subsp. *aestivum*; Club wheat, a.k.a. *Triticum aestivum* subspecies *compactum* (Host) MacKey; Macha wheat, a.k.a. *Triticum aestivum* subsp. *macha* (Dek. and Men.) MacKey; *vavilovi* wheat, a.k.a. *Triticum aestivum* subsp. *vavilovi* (Tuman) Sears; Shot wheat, a.k.a. *Triticum aestivum* subsp. *sphacrococcum* (Perc.) MacKey), *T. aethiopicum*, *T. araraticum*, *T. boeoticum* (e.g., wild Einkorn, a.k.a. *Triticum boeotictim* Boiss), *T. carthlicum*, *T. compactum*, *T. dimitrium*, *T. dicoccoides* (e.g., wild emmer, a.k.a. *Triticum dicoccoides* (Koern. cx Ascb. & Graebn.) Aaronsohn.), *T. dicoccum* (e.g., Emmer), *T. durum* (e.g., durum wheat), *T. ispahanicum*, *T. karamyschevii*, *T. macha*, *T. militinae*, *T. monococcum* (e.g., Einkorn, a.k.a. *Triticum monococcum* L.), *T. polonicum*, *T. spelta*, *T. sphaerococcum*, *T. timopheevii* (e.g. timopheevi wheat, a.k.a. *Triticum timopheevii* Zbuk.), *T. turanicum* (e.g., oriental wheat, a.k.a. *Triticum turanicum* jakubz), *T. turgidum* (e.g., poulard wheat, a.k.a. *Triticum turgidum* L.), *T. urartu*, *T. vavilovii*, and *T. zhukovskyi*.

To introduce the nucleic acid molecules into wheat, for example, nucleic acid molecules are cloned into a binary vector suitable for wheat transformation, such as the vectors described by Zhang et al., 2000 (An efficient wheat transformation procedure: transformed calli with long-term morphogenic potential for plant regeneration, Plant Cell Reports (2000) 19:241-250), Cheng et al., 1997 (Genetic Transformation of Wheat Mediated by *Agrobacterium tumefaciens*, Plant Physiol. (1997) 115:971-980), Abdul et al., (Genetic Transformation of Wheat (*Triticum aestivum* L): A Review, TGG 2010, Vol. 1, No. 2, pp 1-7), Pastori et al., 2000 (Age dependent transformation frequency in elite wheat varieties, J. Exp. Bot. (2001) 52 (357): 857-863), Jones 2005 (Wheat transformation: current technology and applications to grain development and composition, Journal of Cereal Science Volume 41, Issue 2, March 2005, Pages 137-147), Galovic et al., 2010 (MATURE EMBRYO-DERIVED WHEAT TRANSFORMATION WITH MAJOR STRESS MODULATED ANTIOXIDANT TARGET GENE, Arch. Biol. Sci., Belgrade, 62 (3), 539-546), or similar ones.

In some embodiments, the transgenic plant is a species of rice. As used herein, rice refers to the species in the *Oryza* genus, including but not limited to *O. sativa* (e.g., Asian rice), *O. barthii*, *O. glaberrima* (e.g., Africa rice), *O. longistaminata*, *O. meridionalis*, *O. nivara*, *O. rufipogon* (e.g., brownbeard rice and red rice), *O. punctata*, *O. latifolia*, *O. alta*, *O. grandiglumis*, *O. eichingeri*, *O. officinalis*, *O. rhisomatis*, *O. minuta*, *O. australiensis*, *O. granulata*, *O. meyeriana*, and *O. brachyantha*.

To introduce the nucleic acid molecules into rice, for example, the nucleic acid molecules are cloned into a binary vector suitable for rice transformation, such as the vectors described by Lee et al., 2006 (Plastid transformation in the monocotyledonous cereal crop, rice (*Oryza sativa*) and transmission of transgenes to their progeny. Mol. Cells 21, 401-410), Toki et al., 2006 (*Agrobacterium*-mediated transformation of rice, The Plant Journal (2006) 47, 969-976), Nishimura et al., 2007 (A protocol for *Agrobacterium*-mediated transformation in rice, Nature Protocols 1, 2796-2802), Toriyama et al., 1985 (Cell suspension and protoplast culture in rice. Plant Science 41:179-183), Hiei, et al., 1994 (Efficient transformation of rice (*Oryza sativa* L.) mediated by *Agrobacterium* and sequence analysis of the boundaries of the T-DNA. Plant J. 6:271-282), Christou 1997 (Rice transformation: bombardment, Plant Molecular Biology 35:197-203, 1997.), Latha et al. 2006 (Tools for rice transformation: A flexible series of vectors harboring phytohormone genes and specific promoters, Indian J. Crop Science, 1(1-2): 42-48 (2006)), U.S. Pat. Nos. 6,215,051, 6,329,571, or similar experimental procedures well known to those skilled in the art.

In other embodiments, the transgenic plant is in the Fabaceae family, which include legume family, pea family, bean family or pulse family. For example, the transgenic plant may be *Glycine max* (soybean), *Phaseolus* (beans), *Pisum sativum* (pea), *Cicer arietinum* (chickpeas), *Medicago sativa* (alfalfa), *Arachis hypogaea* (peanut), *Ceratonia siliqua* (carob), and *Glycyrrhiza glabra* (licorice).

To introduce the nucleic acid molecules into soybean, for example, the nucleic acid molecules are cloned into a binary vector suitable for soybean species transformation, such as the vectors and methods described by Yi et al. 2006 (Transformation of multiple soybean cultivars by infecting cotyledonary-node with *Agrobacterium tumefaciens*, African Journal of Biotechnology Vol. 5 (20), pp. 1989-1993, 16 Oct. 2006), Paz et al., 2004 (Assessment of conditions affecting *Agrobacterium*-mediated soybean transformation using the cotyledonary node explant, Euphytica 136:167-179, 2004), U.S. Pat. Nos. 5,376,543, 5,416,011, 5,968,830, and 5,569,834, or by similar experimental procedures well known to those skilled in the art.

In some embodiments, the transgenic plant is a dicot. As used herein, the terms "dicotyledon" and "dicot" refer to a flowering plant having an embryo containing two seed halves or cotyledons. Dicotyledon plants at least include the Eudicot, Magnoliid, Amborella, Nymphacales, Austrobaileyales, Chloranthales, and Ceratophyllum groups. Eudicots include these clades: Ranunculales, sabiales, Proteales, Trochodendrales, Buxales, and Core Eudicots (e.g., Berberidopsidales, Dilleniales, Gunnerales, Caryophyllales, Santalales, Saxifragales, Vitales, Rosids and Asterids). Non-limiting examples of dicotyledon plants include tobacco, tomato, pea, alfalfa, clover, bean, soybean, peanut, members of the Brassicaceae family (e.g., camelina, Canola, oilseed rape, etc.), amaranth, sunflower, sugarbeet, cotton, oaks, maples, roses, mints, squashes, daisies, nuts; cacti, violets and buttercups.

In some embodiments, the transgenic plant is a monocot. As used herein, the term "monocotyledon" or "monocot" refer to any of a subclass (Monocotyledoncae) of flowering plants having an embryo containing only one seed leaf and usually having parallel-veined leaves, flower parts in multiples of three, and no secondary growth in stems and roots. Non-limiting examples of monocotyledon plants include lilies, orchids, corn (maize), rice, wheat, barley, sorghum, millets, oats, ryes, triticales, buckwheats, fonio, *quinoa*, grasses, such as tall fescue, goat grass, and Kentucky bluegrass; grains, such as wheat, oats and barley, irises, onions, palms.

For example, to introduce the nucleic acid molecules into corn, the nucleic acid molecules are cloned into a binary vector suitable for corn transformation, such as the vectors described by Sidorov and Duncan, 2008 (*Agrobacterium*-Mediated Maize Transformation: Immature Embryos Versus Callus, Methods in Molecular Biology, 526:47-58), Frame et al., 2002 (*Agrobacterium tumefaciens*-Mediated Transformation of Maize Embryos Using a Standard Binary Vector System, Plant Physiology, May 2002, Vol. 129, pp. 13-22), Ahmadabadi et al., 2007 (A leaf-based regeneration and transformation system for maize (*Zea mays* L.), TransgenicRes. 16, 437-448), U.S. Pat. Nos. 6,420,630, 6,919,494 and 7,682,829, or similar experimental procedures well known to those skilled in the art.

In certain embodiments, the plant is a cultivar. As used herein, the term "cultivar" refers to a variety, strain or race of plant that has been produced by horticultural or agronomic techniques and is not normally found in wild populations.

The invention further contemplates *Arabidopsis* as the target species. *Arabidopsis* is often used as a model plant in biotech research because it offers several advantages to the research setting including but limited to the following: (1) it develops, reproduces and responds to stress and disease much the same way as many crop plants; (2) it produces many seeds and is easy and cheap to grow, since the plant is small and requires little space; (3) it has a shorter life cycle; (4) the low cost of production allows extensive genetic experiments on thousands of plants at once; (5) compared to other plants, it has a small genome and its genetic information is somewhat less complex, allowing for easier genetic analysis; and (6) it is the first plant to have its genome sequenced due to an internationally coordinated program. See, e.g., *Arabidopsis*: Model plant in biotech research (November, 1998) In: The Agbiotech Infosource, Issue 40, Ag-West Biotech Inc.

The invention in certain aspects includes plant parts derived from the transgenic plants described herein. As used herein, the term "plant part" refers to any part of a plant including but not limited to the shoot, root, stem, stalk, trunk, tiller, seeds, endosperm, pedicel, tuber, rhizomes, stipules, stolon, nodules, leaves or leaf sheath, needle, cone, petals, flowers, ovules, fruit, berry, stigma, bracts, peduncle, branches, style, carpel, pericarp, petioles, internodes, bark, pubescence, pollen, stamen, pistil, sepal, anther, placenta, and the like. The two main parts of plants grown in some sort of media, such as soil, are often referred to as the "aboveground" part, also often referred to as the "shoots", and the "below-ground" part, also often referred to as the "roots".

In some embodiments, the invention provides a method of making a transgenic plant having a gene of interest under the control of a synthetic promoter that is operable in rice. The transgenic plant may or may not be a species of rice. The synthetic promoter is a high constitutive promoter, and may comprise the sequence of SEQ ID NO: 1, or a variant or fragment thereof having an equivalent (e.g., ±10%) or improved score in the algorithm described herein. The synthetic element may comprise a nucleotide sequence having an identity to SEQ ID NO:1 of at least 40%, at least 50%, at least 60%, at least 70%, at least 80%, or at least 90%. The score is based upon an analysis of the 395 rice promoters listed in Table 4, and the second set of nucleotide sequences (background elements) is the promoters of all other genes in the rice genome (MSU/TIGR rice genome, version 6.1, rice.plantbiology.msu.edu/index.shtml, Ouyang, S. et al. (2007) Nucleic Acids Res. 35:D883-D887). Both sets of sequences are taken from 1000 bp 5' of the publically annotated transcription start site (TSS) to 50 bp 3' of the TSS (i.e. −1000 to +50), aligned on the annotated TSS. The score is based on two parts. The first part, from −200 to +50, uses the position-dependent algorithm described above using the corresponding regions of the two sets of nucleotide sequences, with word size k=7, kernel width w=10, entropy window width ω=64, pseudocounts ρ=20, frequency weight $\varphi_z$=0.5, and entropy weight $\varepsilon_z$=0.07. Any other parameters are as described above. The second part, from −450 to −200, uses the position-independent algorithm described above using the full length of the two sets of nucleotide sequences, with word length k=7. The nucleotide sequences are partitioned into a total of n=9 bins by GC content (3 bins) and length (3 bins) for the purpose of calculating the probability parameter p for the binomial distribution function. The two halves of the sequences are designed independently and joined together.

In some embodiments, the invention provides a method of making a transgenic plant having a gene of interest under the control of a synthetic promoter. The synthetic promoter is a constitutive promoter, and may comprise the sequence of SEQ ID NO:2, or a variant or fragment thereof having an equivalent (±10%) or improved score in the algorithm described herein. The synthetic element may comprise a nucleotide sequence having an identity to SEQ ID NO:2 of at least 40%, at least 50%, at least 60%, at least 70%, at least 80%, or at least 90%. The score is based upon an analysis of the putative promoters of 32 virus genomes of the family Caulimoviridae, retrieved from NCBI's Viral Genomes resource (www.ncbi.nlm.nih.gov/genomes/GenomesHome.cgi). These promoter sequences are: NC_013262 2, NC_013455 1, NC_004540 1, NC_004036 1, NC_003138 1, NC_0018391 1, NC_004324 2, NC_012728 1, NC_007002 1, NC_008034 1, NC_010738 3, NC_010737 1, NC_008017 1, NC_003554 1, NC_003381 1, NC_003031 1, NC_001725 1, NC_001343 1, NC_001497 1, NC_011920 1, NC_004450 1, NC_009010 1, NC_008018 1, NC_006955 1, NC_003498 1, NC_003382 1, NC_001739 1, NC_001914 1, NC_001648 1, NC_001574 1, NC_011592 1, NC_011097 1. The "simulated background" variant of the position-dependent design algorithm is used. Sequences are taken from 300 bp 5' of the TATA box to 300 bp 3' of the TATA box (i.e. −300 to +300), aligned on the TATA box. The entire sequence (−300 to +300) is scored by the position-dependent algorithm, with word size k=10, kernel width w=15 (adaptive KDE variant), entropy window width ω=64, pseudocounts, ρ=10, frequency weight $\varphi_z$=0.5, and entropy weight $\varepsilon_z$=0.07. Any other parameters were as described above.

In some embodiments, the invention provides a method of making a transgenic plant having a gene of interest under the control of a synthetic promoter. The synthetic promoter is a high constitutive promoter, and may comprise the sequence of SEQ ID NO: 3, 4, or 5, or a variant or fragment thereof having an equivalent (±10%) or improved score in the algorithm described herein. The synthetic element may comprise a nucleotide sequence having an identity to SEQ ID NO: 3, 4 or 5 of at least 40%, at least 50%, at least 60%, at least 70%, at least 80%, or at least 90%. The score is based on analysis of promoters of 48 *Arabidopsis* genes that were highly and constitutively expressed according to the published microarray data of Brady et al. (2007) Science 318: 801-806, and that have a putative TATA box within ±50 bp of the annotated TSS. (TAIR *Arabidopsis* genome, version 9 (TAIR9), www.Arabidopsis.org/). A putative TATA box is any sequence matching the pattern TATAWAW, where W indicates T or A. The 48 *Arabidopsis* genes are listed in Table 5. The score is based on the use of the "simulated background" version of the algorithm. Sequences are taken from 1000 bp 5' of the publically annotated transcription start site (TSS) to 50 bp 3' of the TSS (i.e. −1000 to +50), aligned on the putative TATA box. The entire sequence (−450 to +50) is scored by the position-dependent algorithm using the corresponding region of the training set of nucleotide sequences, with word size k=6, kernel width w=10 (adaptive KDE variant), entropy window width $\omega$=64, pseudocounts $\rho$=10, frequency weight $\varphi_z$=0.5, and entropy weight $\varepsilon_z$=0.07. Any other parameters were as described above.

In some embodiments, the invention provides a method of making a transgenic plant having a gene of interest operably associated with a synthetic intron. The synthetic intron is an expression enhancing intron, and may comprise the sequence of SEQ ID NO: 6, 7, 8, 9, or 10, or a variant or fragment thereof having an equivalent (±10%) or improved score in the algorithm described herein. The synthetic element may comprise a nucleotide sequence having an identity to SEQ ID NO: 6, 7, 8, 9 or 10 of at least 40%, at least 50%, at least 60%, at least 70%, at least 80%, or at least 90%. The score is based on analysis of the first introns of 108 *Arabidopsis* genes that were highly and constitutively expressed according to the published microarray data of Brady et al. (2007) Science 318:801-806. The 108 *Arabidopsis* genes are listed in Table 6. The first introns occur in either the 5' UTR or the coding region, but must start within 500 bp of the annotated TSS. The second set of nucleotide sequences (background elements) is the non-first introns of all genes in the *Arabidopsis* genome. Non-first introns start at least 1000 bp from the annotated TSS. Both sets of sequences include the first and last 150 bp of each intron, plus 10 bp of the surrounding exons. For introns shorter than 300 bp, sequence duplication is used, but avoiding duplication of splice sites or branch points. The score is based on the position-dependent algorithm, with word size k=5, kernel width w=5, entropy window width $\omega$=64, pseudocounts $\rho$=50, frequency weight $\varphi_z$=5.0, and entropy weight $\varepsilon_z$=150. Any other parameters were as described above.

In some embodiments, the transgenic plant has a gene of interest under control of a synthetic promoter and synthetic intron as described above.

The methods described herein can be used in connection with basic plant breeding techniques. For example, the transgenic plant may be inbred or a single allele converted plant. As used herein, the term "inbred" or "inbred plant" includes any single gene conversions of that inbred. The phrase "single allele converted plant" refers to those plants which are developed by a plant breeding technique called backcrossing wherein essentially all of the desired morphological and physiological characteristics of an inbred are recovered in addition to the single allele transferred into the inbred via the backcrossing technique. In some embodiments, an offspring plant may be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids. Developing the transgenic plants may further include crossing. As used herein, the term "cross", "crossing", "cross pollination" or "cross-breeding" refer to the process by which the pollen of one flower on one plant is applied (artificially or naturally) to the ovule (stigma) of a flower on another plant.

In certain embodiments, the invention involves transformation of cells. As used herein, the term "transformant" refers to a cell, tissue or organism that has undergone transformation. The original transformant may be designated as "T0" or "$T_0$." Selfing the T0 produces a first transformed generation designated as "T1" or "$T_1$."

In some embodiments, the transgenic cell or organism is hemizygous for the gene of interest under control of the synthetic regulatory element. As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

In some embodiments, the cell or organism is heterozygous for the gene of interest under control of the synthetic regulatory element. As used herein, the term "heterozygote" refers to a diploid or polyploid individual cell or plant having different alleles (forms of a given gene) present at least at one locus. Similarly, the term "heterozygous" refers to the presence of different alleles (forms of a given gene) at a particular gene locus.

In other embodiments, the cell or organism is a homozygote for the gene of interest under control of the synthetic element. As used herein, the term "homozygote" refers to an individual cell or plant having the same alleles at one or more loci. Thus, the term "homozygous" refers to the presence of identical alleles at one or more loci in homologous chromosomal segments.

Any transgenic plant comprising one or more synthetic promoters and/or synthetic introns of the present invention can be used as a donor to produce more transgenic plants through plant breeding methods well known to those skilled in the art. The goal in general is to develop new, unique and superior varieties and hybrids. In some embodiments, selection methods, e.g., molecular marker assisted selection, can be combined with breeding methods to accelerate the process.

In some embodiments, said methods comprise (i) crossing any one of the plants of the present invention comprising one or more synthetic promoters and/or synthetic introns as a donor to a recipient plant line to create a F1 population; (ii) evaluating the transgene expression in the offsprings derived from said F1 population; and (iii) selecting offsprings that have functional transgene expression under the control of the synthetic promoters and/or synthetic introns.

In some embodiments, complete chromosomes of the donor plant are transferred. For example, the transgenic plant with the synthetic promoters and/or synthetic introns can serve as a male or female parent in a cross pollination to produce offspring plants, wherein by receiving the transgene from the donor plant, the offspring plants obtained the synthetic promoters and/or synthetic introns. In some embodiments, only the genomic fragment containing the transgene (e.g., having the synthetic promoters and/or synthetic introns) is incorporated into the recipient plant.

In some embodiments, the recipient plant is an elite line having one or more certain agronomically important traits. As used herein, "agronomically important traits" include any phenotype in a plant or plant part that is useful or advantageous for human use. Examples of agronomically important traits include but are not limited to those that result in increased biomass production, production of specific biofuels, increased food production, improved food quality, etc. Additional examples of agronomically important traits includes pest resistance, vigor, development time (time to harvest), enhanced nutrient content, novel growth patterns, flavors or colors, salt, heat, drought and cold tolerance, and the like. For example, the recipient plant can be a plant with increased seed weight and/or seed size. The recipient plant can also be a plant with preferred carbohydrate composition, e.g., composition preferred for nutritional or industrial applications, especially those plants in which the preferred composition is present in seeds.

*Brassica* breeding and agriculturally important traits (e.g., improving yield, biotic stress tolerance, and abiotic stress tolerance etc.) are described in, for example, Brown, J. and A. P Brown, 1997 (Gene transfer between canola (*Brassica napus* L. and *B. campestris* L.) Ann. Appl. Biol. 129:513-522); Montei, 1998, (Trend and perspectives of vegetable *brassica* breeding world-wide, World Conference on Horticultural Research, 1998); McCaughey et al., 2010 (Overview of *Brassica* Breeding and Genomics Research at AAFC); and Mark et al., 2005 (Breeding program for disease resistance in *Brassica* Crops, North Carolina Vegetable Growers Association).

Soybean breeding and agriculturally important traits are described in, for example, Pathan and Sleper 2008 (Advances in Soybean Breeding, Plant Genetics and Genomics: Crops and Models, 2008, Volume 2, Part II, 113-133); Wilcox 1987 (Soybeans: improvement, production, and uses, American Society of Agronomy, 1987, ISBN 0891180907, 9780891180906); Singh, 2010 (The Soybean: Botany, Production and Uses, CABI, 2010, ISBN 1845936442, 9781845936440); Openshaw et al. 1994, (Marker-assisted selection in backcross breeding". pp. 41-43.); Poehlman et al (1995) *Breeding Field Crop,* 4th Ed., Iowa State University Press, Ames, I A., pp. 132-155 and 321-344); and Werner et al., 2004 (Recurrent selection for yield in *Glycine max* using genetic male-sterility. Euphytica 50 (1), 19-26) and U.S. Pat. No. 7,838,740. Each of the references is incorporated herein by reference in its entirety.

Corn breeding and agriculturally important traits are described in, for example, Allard, Principles of Plant Breeding, 1960; Simmonds, Principles of Crop Improvement, 1979; Fehr, "Breeding Methods for Cultivar Development", Production and Uses, 2nd ed., Wilcox editor, 1987, Carena et al., 2010 (Quantitative Genetics in Maize Breeding, Springer, 2010 ISBN 1441907653, 9781441907653); Meghji, M. R., et al., 1984 (Inbreeding Depression, Inbred & Hybrid Grain Yields, and Other Traits of Maize Genotypes Representing Three Eras", *Crop Science,* Vol. 24, pp. 545-549), and Kriz and Larkins, 2008 (Molecular Genetic Approaches to Maize Improvement, Springer, 2008, ISBN 3540689192, 9783540689195). Each of the references is incorporated herein by reference in its entirety.

Rice breeding and agriculturally important traits are described in Virmani et al., (Two-Line Hybrid Rice Breeding Manual, International Rice Research Institute); Virmani 1997 (Hybrid Rice Breeding Manual, International Rice Research Institute, ISBN 9712201031, 9789712201035); Hu et al. (A draft sequence of the rice genome (*Oryza sativa* L. ssp. *indica*) Science 296:79-92); Yang et al., 1996 (Theories and methods of rice breeding for maximum yield. Acta Agron. Sin. 22 (3), 295-304); Wenfu et al. 2001, (Development of the new rice plant type and advances in research on breeding for super high yield. Rice research for food security and poverty alleviation. International Rice Research Institute, Manila, Philippines, pp. 43-50); Vaughan, 1994 (The wild relatives of rice, A genetic resources handbook. International Rice Research Institute, Manila, Philippines. pp. 1-137); and Guimaraes 2009 (Rice Breeding, M. J. Carena (ed.), Cereals, The Banks and the Italian Economy DOI: 10.1007/978-0-387-72297-9), and Datta 1981 (Principles and Practices of Rice Production, Int. Rice Res. Inst., 1981, ISBN 0471097608, 9780471097600). Each of the references is incorporated herein by reference in its entirety.

Wheat breeding and agriculturally important traits (e.g., improving wheat yield, biotic stress tolerance, and abiotic stress tolerance etc.) are described in Slafer and Araus, 2007, ("Physiological traits for improving wheat yield under a wide range of conditions", Scale and Complexity in Plant Systems Research: Gene-Plant-Crop Relations, 147-156); Reynolds ("Physiological approaches to wheat breeding", *Agriculture and Consumer Protection*. Food and Agriculture Organization of the United Nations); Richard et al., ("Physiological Traits to Improve the Yield of Rainfed Wheat: Can Molecular Genetics Help", published by International Maize and Wheat Improvement Center.); Reynolds et al. ("Evaluating Potential Genetic Gains in Wheat Associated with Stress-Adaptive Trait Expression in Elite Genetic Resources under Drought and Heat Stress Crop science", Crop Science 2007 47: Supplement 3: S-172-S-189); Setter et al., (Review of wheat improvement for waterlogging tolerance in Australia and India: the importance of anaerobiosis and element toxicities associated with different soils. Annals of Botany, Volume 103(2): 221-235); Foulkes et al., (Major Genetic Changes in Wheat with Potential to Affect Disease Tolerance. Phytopathology, July, Volume 96, Number 7, Pages 680-688 (doi: 10.1094/PHYTO-96-0680); Rosyara et al., 2006 (Yield and yield components response to defoliation of spring wheat genotypes with different level of resistance to *Helminthosporium* leaf blight. Journal of Institute of Agriculture and Animal Science 27. 42-48.); U.S. Pat. Nos. 7,652,204; 6,197,518; 7,034,208; 7,528,297; 6,407,311; 20,080,040826; US20090300783; US20060223707; US20110027233; US20080028480; US20090320152; US20090320151; WO/2001/029237A2; WO/2008/025097A1; and WO/2003/057848A2, each of which is incorporated by reference in its entirety for all purposes.

The invention further provides methods for developing plants in a plant breeding program using plant breeding techniques including recurrent selection, backcrossing, pedigree breeding, molecular marker (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites, etc.) enhanced selection, genetic marker enhanced selection and transformation. Seeds, plants, and parts thereof produced by such breeding methods are also part of the invention.

This invention is further illustrated by the following examples which should not be construed as limiting. The contents of all references, patents and published patent

Example 1

Preparation and Quantitative Root Expression Testing of Identified Synthetic Promoters in Stably Transformed *Arabidopsis*

To assess promoter activity of certain synthetic promoters prepared in accordance with the invention in stable transformed plants, nucleic acid molecules comprising each of the nucleotide sequences set forth in SEQ ID NOS: 1-5 (synthetic promoters SP1-SP5) were synthesized with flanking AscI and RsrII sites and cloned into a pUC57 vector by a contract DNA synthesis vendor (GenScript USA Inc., Piscataway, NJ 08854). The AscI/RsrII promoter-containing fragment from the resulting plasmid was then excised and cloned into AscI and RsrII sites of binary vector pGR716 using standard molecular biology procedures. pGR716 is a modified version of the binary vector pCambia0380. To construct pGR716, the region between the left and right T-DNA borders of pCambia0380 was replaced with an expression cassette consisting of a constitutively expressed NptII kanamycin resistance gene followed by a promoterless mGFP5-ER gene with AscI and RsrII sites 5' to the ATG start codon. The final constructs were transferred to *Agrobacterium* for transformation into *Arabidopsis* 'Columbia' ecotype plants by the floral dip method (Clough and Bent (1998) *Plant J.* 16:735) to generate polynucleotide::GFP fusions in transgenic plants. Transformed plants (T1) are selected by growth in the presence of kanamycin. Following selection, transformants are transferred to MS plates and allowed to recover.

In general, at least 12 kanamycin resistant T1s were selected per construct and allowed to set seed (T2 generation). Copy number analysis was performed on excised leaves of the T1s by qPCR. Typically, representative T2 seedlings from the 6 lowest copy number lines of each construct were visually screened for GFP fluorescence with a fluorescent microscope.

Constructs that showed GFP fluorescence in 2 or more independent transgenic lines were analyzed further. To assess expression in root tissues, T2 seedlings from two lines with observable GFP fluorescence were grown in MS media in the RootArray, a device designed for confocal imaging of living plant roots under controlled conditions, and described in U.S. Patent Publication No. 2008/0141585 which is hereby incorporated by reference in its entirety. After 5 days growth, the roots were stained with FM4-64 and imaged for GFP fluorescence in the meristematic zone, elongation zone and maturation zone with approximately 50 seedlings analyzed per line.

In order to yield quantitative results from image pixel intensities, imaging conditions and measurements were strictly controlled. The imaging normalization and calibration methods were based on two key measurements. First, on any day measurements are taken, a dilution series of an external reference fluorophore was quantitatively imaged. Second, the post-objective laser intensity was directly measured before and after each RootArray experiment in order to account for variations in laser light intensity that may have occurred.

The dilution series that was imaged each day was prepared from a reference standard. The reference standard was prepared from a concentrated stock of Alexa Fluor 488 in MES buffer (pH 6.0), with its concentration determined by spectrophotometry. Aliquots of the reference standard were stored at −20° C. as a master stock. For calibration use, a dilution series of the stock was prepared in a sealed, modified 96 well plate. The dilution series was stored at 4° C. in the dark and used for up to one month before being replaced. The Alexa Fluor standard was verified to be stable under these conditions. The dilution series was imaged at the beginning of each day to characterize the performance of the detector and optics of the microscope as described below.

Tests have shown that laser light intensity can vary up to 10% at a given setting over the course of a RootArray experiment. To correct for this, laser power is measured before and after each RootArray experiment. The laser intensity is actively adjusted to 355±15 µW at 488 nm at the beginning of each experiment. The change in intensity measured at the end of a RootArray experiment was assumed to be due to a linear transition. Therefore, the estimated light intensity for a specific RootArray image was interpolated from that image's timestamp.

To correct for variations in laser intensity and detector response a model was developed to describe how Alexa Fluor 488 fluorescence varied with laser intensity under the imaging conditions described herein. The laser correction model for Alexa Fluor 488 is based on the relative change of the dilution series slope versus the relative change of laser light intensity. Experiments have demonstrated that this relationship is independent of scan settings. This model was then adapted to GFP in root tissue with the addition of a GFP specific variable. This model is used to calculate a GFP expression index (GEI) as described in Equation 1 below.

$$GBI = \frac{\mu(rot(Img) - bkg(Img))}{\alpha_{AF}^{DS} \beta_{Sat}} \gamma_{AF}^{DS} \gamma_{AF}^{Img} \delta_{GFP}^{Img}$$

rol(Img): The pixel population for the quantification channel (green channel) over a selected region of interest. In this case each ROI is a tissue type.

bkg(Img): The background pixel value for every experimental image is characterized with a novel statistics based approach, described below.:

$\alpha_{AF}^{DS}$: Normalized slope of the dilution series standard.:

$\gamma_{AF}^{DS}$: Laser correction factor for Alexa Fluor 488 fluorophore to normalize the dilution series to the reference laser power (355 µW at 488 nm).

$\gamma_{AF}^{Img}$: Laser correction factor for Alexa Fluor 488 fluorophore at the laser power the GFP image was taken.

$\delta_{GFP}^{Img}$: Relative laser correction factor for GFP fluorophore in the experimental image.

$\beta_{Sat}$: Normalization constant to prevent pixel oversaturation of the detector when the image was acquired.

The green channel image signal passes through this function to produce the GEI, a metric of fluorescent intensity that allows for comparison across RootArrays over time. The background of each experimental image was calculated as described below and subsequently subtracted from the pixel population of the region of interest. The negative values were zeroed to create an image with minimal background noise. The mean of corrected pixel intensities was divided by the slope of the dilution series to convert the pixel output to a metric of light intensity relative to the dilution series standard. The first gamma value $\gamma_{AF}^{DS}$ is a laser correction factor that adjusts the slope of the dilution series to what it would be if the dilution series was imaged at exactly 355 µW. The next gamma $\gamma_{AF}^{Img}$ and the delta values $\delta_{GFP}^{Img}$ correct the GFP signal to what it would be if the root was imaged at exactly 355 µW. It is noted that all correction factors typically varied by less than 5% between experiments.

Regions of interest that have a strong signal near the point of pixel oversaturation of the detector did not exhibit a linear relationship with GFP expression. Therefore a normalization constant $\beta_{Sat}$ was included to limit the scope of the dynamic bit range of the detector and the GEI is capped at 1 to preserve its linear correlation with GFP expression for all reported values <1. To calculate the background of an image bkg(Img), the image was first split into a grid of squares and The average GEI for each of the 14 tissue-zone ROIs for two representative lines of five nucleic acid molecules that passed prescreening is shown in Table 1. All values for the nucleic acid molecules in Table 1 represent significant expression ($p<0.01$). The GEIs measured from seedlings containing a CaMV 35S promoter-GFP transgene are shown for comparison. The 35S promoter is widely used in plant biotechnology and considered a standard for strong promoters. These data demonstrate that the promoters of the present drive significant expression of an operably linked gene of interest, in all root tissues.

TABLE 1

GFP Expression Index (GEI) in Root Tissue for Five Synthetic Nucleic Acid Molecules with Promoter Activity

| | Meristem | | | | | | Elongation | | | | Maturation | | | |
|---|---|---|---|---|---|---|---|---|---|---|---|---|---|---|
| Promote | epi* | cor | end | ste | qc | cap | epi | cor | end | ste | epi | cor | end | ste |
| SP1-1 | 0.077 | 0.078 | 0.07 | 0.068 | 0.019 | 0.027 | 0.022 | 0.017 | 0.013 | 0.017 | 0.01 | 0.006 | 0.008 | 0.014 |
| SP1-2 | 0.242 | 0.253 | 0.208 | 0.153 | 0.065 | 0.094 | 0.040 | 0.035 | 0.027 | 0.033 | 0.016 | 0.011 | 0.016 | 0.037 |
| SP2-1 | 0.32 | 0.311 | 0.287 | 0.216 | 0.167 | 0.188 | 0.096 | 0.084 | 0.067 | 0.058 | 0.022 | 0.018 | 0.022 | 0.037 |
| SP2-2 | 0.046 | 0.038 | 0.033 | 0.019 | 0.324 | 0.257 | 0.047 | 0.01 | 0.006 | 0.005 | 0.072 | 0.043 | 0.04 | 0.073 |
| SP3-1 | 0.222 | 0.306 | 0.274 | 0.171 | 0.161 | 0.129 | 0.072 | 0.059 | 0.051 | 0.039 | 0.014 | 0.014 | 0.018 | 0.033 |
| SP3-2 | 0.336 | 0.358 | 0.341 | 0.271 | 0.318 | 0.274 | 0.088 | 0.066 | 0.055 | 0.047 | 0.021 | 0.019 | 0.024 | 0.058 |
| SP4-1 | 0.162 | 0.169 | 0.153 | 0.106 | 0.057 | 0.065 | 0.052 | 0.031 | 0.021 | 0.021 | 0.019 | 0.011 | 0.012 | 0.017 |
| SP4-2 | 0.529 | 0.556 | 0.495 | 0.381 | 0.124 | 0.212 | 0.186 | 0.13 | 0.1 | 0.093 | 0.041 | 0.031 | 0.041 | 0.054 |
| SP5-1 | 0.241 | 0.318 | 0.261 | 0.122 | 0.012 | 0.016 | 0.116 | 0.114 | 0.084 | 0.059 | 0.021 | 0.021 | 0.024 | 0.024 |
| SP5-2 | 0.366 | 10.42 | 0.389 | 0.257 | 0.048 | 0.065 | 0.136 | 0.119 | 0.1 | 0.084 | 0.025 | 0.026 | 0.035 | 0.059 |
| CaMV | 0.396 | 0.282 | 0.236 | 0.229 | 0.957 | 1 | 0.24 | 0.083 | 0.084 | 0.195 | 0.235 | 0.216 | 0.31 | 0.545 |

*In Table 1, "epi" is epidermis, "cor" is cortex, "end" is endodermis, "ste" is stele, "qc" is quiescent center, and "cap" is root cap.

the pixel population of each square is examined. A small number of squares was initially selected based on having the lowest percentile rankings in terms of standard deviation, 95th percentile pixel value, mean, median, and gradient magnitude. The pixel populations in the initial "seed" squares, which are assumed to be background, were then compared against the pixel populations of all other squares in a one-tailed unpaired t test in order to categorize each square as "background" or "non-background". The median pixel intensity of all squares determined to be "background" was then used as the bkg (Img) value in Equation 1. Tests have shown that this algorithm robustly selected background pixel populations even if there were several roots in the field of view.

The correspondence of regions of interest to different cell-types was determined from the images using a predefined root template. The template was calculated using a series of images manually segmented to find the root's "tissue percentage profile" (TPP), in which each region of interest in the template is a percentage of the root thickness at the specified location relative to the quiescent center (QC). Using different TPPs for each root zone, the images were segmented into different regions of interest (ROI) corresponding to different root cell-types. Specifically, the regions determined in all three developmental zones were the epidermis, the cortex, the endodermis, and the stele. In addition to these four regions, the root cap and the quiescent center were also determined in the meristematic zone.

To determine if a particular transgenic line exhibited significant GFP expression in an ROI, the GEI measurements for each of the 14 tissue-zone ROIs were compared to the corresponding values determined from 48 non-transgenic *Arabidopsis* Columbia ecotype seedlings grown under identical conditions. Significance was determined using a one-tailed Welch's t-test with a cutoff of $p<0.01$.

Expression of GFP in aerial tissue of the stably transformed *Arabidopsis* described above was assessed by qRT-PCR. T2 seeds from each line were grown on MS agar plates. After 4 days the segregating seedlings were screened for GFP fluorescence to identify those that carried the transgene. The GFP positive seedlings were grown an additional 7 days after which the aerial portions of approximately 10 GFP positive plants were collected in triplicate for RNA extraction and cDNA synthesis. Tissue was homogenized in liquid nitrogen via bead milling and total RNA was extracted using the Allprep DNA/RNA kit (Qiagen). cDNA was generated from total RNA using the Superscript VILO cDNA synthesis kit (Invitrogen) per the manufacturer's instructions. Multiplex qPCR TaqMan assays were conducted using either the CFX96 Real-Time PCR Detection System or the iCycler iQ Real-Time PCR Detection System (both instruments are from Bio-Rad Laboratories) with primers and probes specific for GFP and the strong, constitutively expressed, internal control gene UBC9 (AT4G27960). Three technical qRT-PCR replicates were performed on each biological replicate, and data was processed using CFX Manager software (Bio-Rad).

To determine relative GFP expression level, PCR reaction efficiency was calculated using LinRegPCR software (Ruijter) and verified using a standard curve based method. Ct and baseline threshold values were obtained from the CFX Manager software. Data analysis was performed using the statistics package R, available at the R Project for Statistical Computing. After correcting the Ct values for reaction efficiency, the relative GFP expression was calculated by subtracting the Ct of the UBC control from that of GFP, followed by averaging across all replicates. To assess statistical significance of the data, the relative GFP expression of each line was compared to that determined from non-transgenic *Arabidopsis* ecotype Columbia seedlings using a one-tailed Welch's t-test. All statistical analysis was performed on the corrected Ct values, but these values were exponentiated to a linear expression scale for presentation. To normalize the linear expression scale, the data was expressed relative to a 35S-promoter control that was included in all experiments. The 35S-promoter control value was set to 100 on this scale.

Aerial expression data for the two representative lines of the five nucleic acid molecules is shown in Table 2. All expression measurements were statistically significant (p<0.01). These data demonstrate that the synthetic promoters drive significant expression of an operably linked gene of interest.

TABLE 2 qRT-PCR Expression Data in Aerial Tissue for Five Synthetic Nucleic Acid Molecules with Promoter Activity

| Promote | Relative Expression |
| --- | --- |
| SP1-1 | 0.2 |
| SP1-2 | 0.6 |
| SP2-1 | 2.9 |
| SP2-2 | 1.7 |
| SP3-1 | 3.8 |
| SP3-2 | 6.7 |
| SP4-1 | 0.9 |
| SP4-2 | 1.4 |
| SP5-1 | 0.1 |
| SP5-2 | 0.8 |

Example 2

Preparation and Testing of Expression-Enhancing Activity of Identified Synthetic Introns in Stably Transformed *Arabidopsis*

The expression enhancement activity of synthetic introns, prepared in accordance with this disclosure, was assessed in stable transformed plants. Nucleic acid molecules comprising each of the nucleotide sequences set forth SEQ ID NOS: 6-10 were linked to the 3'-end of promoter-5'-UTR sequences from each of the *Arabidopsis* AT4G37830 and AT1G51650 genes. The promoter-UTR sequences that were used to assess expression enhancement activity comprise either 857 bp of AT4G37830 or 815 bp of AT1G5160 of sequence directly upstream of the ATG start codons of the respective genes. These promoter-UTR sequences were previously shown to drive GFP expression in all root tissues when operably linked to enhancing introns, but did not drive detectable GFP expression in the absence of enhancing introns (see, PCT/US2011/043197, which is hereby incorporated by reference in its entirety).

Each promoter-UTR-intron sequence was synthesized as a single polynucleotide with flanking AscI and RsrII sites and cloned into a pUC57 vector by a contract DNA synthesis vendor (GenScript USA Inc., Piscataway, NJ 08854). The AscI/RsrII promoter-UTR-intron containing fragment from the resulting plasmid was then excised and cloned into AscI and RsrII sites of binary vector pGR716 using standard molecular biology procedures. pGR716 is a modified version of the binary vector pCambia0380. To construct pGR716, the region between the left and right T-DNA borders of pCambia0380 was replaced with an expression cassette consisting of a constitutively expressed NptII kanamycin resistance gene followed by a promoterless mGFP5-ER gene with AscI and RsrII site 5' to the ATG start codon. The final constructs were transferred to *Agrobacterium* for transformation into *Arabidopsis* Columbia ecotype plants by the floral dip method (Clough and Bent (1998) *Plant J*. 16:735) to generate polynucleotide::GFP fusions in transgenic plants. Transformed plants (T1) were selected by growth in the presence of kanamycin. Following selection, transformants were transferred to MS plates and allowed to recover.

In general, about 20-40 kanamycin resistant T1s were visually screened under a fluorescent microscope for GFP fluorescence in root tissues. Average expression of each promoter and intron combination was scored by eye using the following scale: "−" for no detectable expression; 1 to 5 "+" s for minimal to very strong expression, respectively; and "nd" if not tested (see Table 3). Note that in the absence of an intron, neither promoter is capable of driving detectable GFP expression.

TABLE 3

Expression Enhancement of Two Promoters by Operably Linking Five Synthetic Introns Combinations

| Intron | AT4G37830 | AT1G51650 |
| --- | --- | --- |
| SI 1 | ++ | ++ |
| SI 2 | ++++ | +++ |
| SI 3 | +++ | Ind |
| SI 4 | +++ | +++ |
| SI 5 | +++ | ++ |
| None | − | − |

*nd = not determined

The data shown in Table 3 demonstrate that expression-enhancing introns of the present invention can be operably linked to promoters to enhance their expression activity.

Example 3

Construction of Genetic Regulatory Elements

The genetic regulatory element comprising SEQ ID NO: 1 (SP1) was made as follows. The set of regulatory elements was the promoters of 395 rice genes that were highly and constitutively expressed according to the published microarray data of Hirose et al. (2007) *Plant Cell Physiol*. 48:523-539 and Jain et al. (2007) Plant Physiology 143:1467-1483. The 395 rice genes that were used are listed in Table 4. The second set of nucleotide sequences (background elements) was the promoters of all other genes in the rice genome (MSU/TIGR rice genome, version 6.1, rice.plantbiology.msu.edu/index.shtml, Ouyang, S. et al. (2007) *Nucleic Acids Res*. 35: D883-D887). Both sets of sequences were taken from 1000 bp 5' of the publically annotated transcription start site (TSS) to 50 bp 3' of the TSS (i.e. −1000 to +50), aligned on the annotated TSS. The sequence was designed in two parts. The first part, from −200 to +50, was designed using the position-dependent algorithm described above using the corresponding regions of the two sets of nucleotide sequences, with word size k=7, kernel width w=10, entropy window width ω=64, pseudocounts ρ=20, frequency weight $\varphi_z$=0.5, and entropy weight $\varepsilon_z$=0.07. Any other parameters were as described above. Any designed sequence with the sequence "ATG" 3' of the expected TSS was rejected post-design. The second part, from −450 to −200, was designed using the position-independent algorithm described above using the full length of the two sets of nucleotide sequences, with word length k=7. Nucleotide sequences were partitioned into a total of n=9 bins by GC content (3 bins) and length (3 bins) for the purpose of calculating the probability parameter p for the binomial distribution function. The two halves of the sequences were designed independently and joined together afterwards.

TABLE 4

Set of 395 Constitutively Expressed Rice Genes[1]

| | | | |
|---|---|---|---|
| Os01g04650 | Os01g04730 | Os01g05490 | Os01g05900 |
| Os01g06010 | Os01g07370 | Os01g07760 | Os01g10820 |
| Os01g14950 | Os01g15010 | Os01g15110 | Os01g15270 |
| Os01g16890 | Os01g17190 | Os01g19840 | Os01g21440 |
| Os01g22490 | Os01g22520 | Os01g22990 | Os01g24690 |
| Os01g36890 | Os01g36890 | Os01g36950 | Os01g37800 |
| Os01g38620 | Os01g40690 | Os01g46610 | Os01g46926 |
| Os01g47340 | Os01g47660 | Os01g48420 | Os01g48420 |
| Os01g48770 | Os01g53520 | Os01g56890 | Os01g59440 |
| Os01g59790 | Os01g59990 | Os01g60410 | Os01g61814 |
| Os01g61814 | Os01g61814 | Os01g62230 | Os01g67054 |
| Os01g67134 | Os01g68790 | Os01g68950 | Os01g69250 |
| Os01g70170 | Os01g71230 | Os01g72080 | Os02g01560 |
| Os02g02890 | Os02g02890 | Os02g03860 | Os02g06640 |
| Os02g06640 | Os02g06640 | Os02g06700 | Os02g07260 |
| Os02g07790 | Os02g08090 | Os02g08544 | Os02g10200 |
| Os02g10700 | Os02g11050 | Os02g12800 | Os02g18550 |
| Os02g21970 | Os02g30050 | Os02g30624 | Os02g32030 |
| Os02g32350 | Os02g33080 | Os02g33710 | Os02g37420 |
| Os02g37862 | Os02g38920 | Os02g39630 | Os02g39720 |
| Os02g42320 | Os02g43930 | Os02g46962 | Os02g47140 |
| Os02g48560 | Os02g48660 | Os02g48660 | Os02g48720 |
| Os02g49530 | Os02g52250 | Os02g52290 | Os02g54160 |
| Os02g54470 | Os02g54990 | Os02g55370 | Os02g55430 |
| Os02g56960 | Os02g57510 | Os03g01910 | Os03g03390 |
| Os03g04750 | Os03g06240 | Os03g08440 | Os03g08500 |
| Os03g10340 | Os03g10340 | Os03g12670 | Os03g12670 |
| Os03g13170 | Os03g13380 | Os03g16110 | Os03g16690 |
| Os03g17010 | Os03g21940 | Os03g22270 | Os03g22340 |
| Os03g22460 | Os03g22810 | Os03g22890 | Os03g23010 |
| Os03g23010 | Os03g27820 | Os03g29460 | Os03g30430 |
| Os03g37970 | Os03g38000 | Os03g40180 | Os03g40270 |
| Os03g40920 | Os03g40920 | Os03g40920 | Os03g40920 |
| Os03g40920 | Os03g44620 | Os03g46770 | Os03g46770 |
| Os03g48080 | Os03g50290 | Os03g50885 | Os03g50885 |
| Os03g51600 | Os03g51600 | Os03g52690 | Os03g52690 |
| Os03g53190 | Os03g53270 | Os03g54980 | Os03g55150 |
| Os03g56790 | Os03g57790 | Os03g58150 | Os03g58204 |
| Os03g58840 | Os03g59310 | Os03g59710 | Os03g59740 |
| Os03g59740 | Os03g60590 | Os04g01290 | Os04g18090 |
| Os04g28180 | Os04g30780 | Os04g31070 | Os04g32560 |
| Os04g32710 | Os04g32950 | Os04g35300 | Os04g36700 |
| Os04g37690 | Os04g38870 | Os04g42090 | Os04g42270 |
| Os04g42600 | Os04g42930 | Os04g45070 | Os04g46390 |
| Os04g47690 | Os04g50990 | Os04g52090 | Os04g52180 |
| Os04g53620 | Os04g53740 | Os04g54430 | Os04g55920 |
| Os04g56520 | Os04g57220 | Os04g58110 | Os05g01600 |
| Os05g02260 | Os05g02780 | Os05g02990 | Os05g03150 |
| Os05g04510 | Os05g04630 | Os05g05700 | Os05g05940 |
| Os05g06310 | Os05g06350 | Os05g06430 | Os05g06770 |
| Os05g07700 | Os05g07700 | Os05g11710 | Os05g14180 |
| Os05g23720 | Os05g24550 | Os05g24970 | Os05g27780 |
| Os05g27940 | Os05g28190 | Os05g28290 | Os05g33880 |
| Os05g34070 | Os05g34540 | Os05g34770 | Os05g37330 |
| Os05g38520 | Os05g38550 | Os05g41060 | Os05g41110 |
| Os05g41480 | Os05g41900 | Os05g41930 | Os05g42424 |
| Os05g42424 | Os05g42424 | Os05g43252 | Os05g43280 |
| Os05g44050 | Os05g45660 | Os05g45660 | Os05g47980 |
| Os05g48960 | Os05g49030 | Os05g49200 | Os05g49890 |
| Os06g01700 | Os06g02144 | Os06g02540 | Os06g04030 |
| Os06g04290 | Os06g05880 | Os06g07969 | Os06g09390 |
| Os06g12690 | Os06g15360 | Os06g23290 | Os06g36160 |
| Os06g37180 | Os06g37440 | Os06g41010 | Os06g42720 |
| Os06g43650 | Os06g43850 | Os06g44374 | Os06g45120 |
| Os06g46770 | Os06g46770 | Os06g46770 | Os06g46770 |
| Os06g47350 | Os06g48350 | Os06g48750 | Os06g49480 |
| Os06g50154 | Os06g51150 | Os06g51150 | Os06g51220 |
| Os06g51510 | Os07g05580 | Os07g07350 | Os07g08760 |
| Os07g08840 | Os07g08840 | Os07g12650 | Os07g13530 |
| Os07g14270 | Os07g25420 | Os07g32420 | Os07g32800 |
| Os07g34589 | Os07g34589 | Os07g36254 | Os07g37770 |
| Os07g39400 | Os07g39870 | Os07g40580 | Os07g41790 |
| Os07g42950 | Os07g43730 | Os07g46750 | Os07g47290 |

TABLE 4-continued

Set of 395 Constitutively Expressed Rice Genes[1]

| | | | |
|---|---|---|---|
| Os07g47510 | Os07g47580 | Os07g47710 | Os07g48780 |
| Os07g49400 | Os07g49400 | Os08g02340 | Os08g02400 |
| Os08g03290 | Os08g03290 | Os08g03579 | Os08g03640 |
| Os08g06040 | Os08g06140 | Os08g09240 | Os08g09250 |
| Os08g18110 | Os08g22354 | Os08g23710 | Os08g27850 |
| Os08g31810 | Os08g33920 | Os08g37320 | Os08g37444 |
| Os08g37490 | Os08g39140 | Os08g42000 | Os08g44450 |
| Os09g02700 | Os09g07510 | Os09g08430 | Os09g15770 |
| Os09g17730 | Os09g20350 | Os09g24540 | Os09g26420 |
| Os09g26880 | Os09g30412 | Os09g32976 | Os09g33480 |
| Os09g33810 | Os09g33986 | Os09g33986 | Os09g38030 |
| Os09g39400 | Os09g39500 | Os09g39540 | Os10g08550 |
| Os10g08550 | Os10g08930 | Os10g10500 | Os10g11260 |
| Os10g20630 | Os10g21230 | Os10g25770 | Os10g27174 |
| Os10g30580 | Os10g31000 | Os10g32920 | Os10g33230 |
| Os10g37420 | Os10g39410 | Os10g42710 | Os11g03380 |
| Os11g03400 | Os11g06390 | Os11g06750 | Os11g06890 |
| Os11g09280 | Os11g11390 | Os11g21990 | Os11g23854 |
| Os11g26850 | Os11g26910 | Os11g29190 | Os11g38959 |
| Os11g38959 | Os11g40140 | Os11g40510 | Os11g43900 |
| Os11g43900 | Os11g44810 | Os11g47760 | Os11g47760 |
| Os12g01390 | Os12g03090 | Os12g07010 | Os12g12360 |
| Os12g21754 | Os12g32240 | Os12g32240 | Os12g32380 |
| Os12g32950 | Os12g36640 | Os12g36640 | Os12g36640 |
| Os12g37419 | Os12g38000 | Os12g41220 | Os12g42180 |
| Os12g42884 | Os12g42884 | Os12g43600 | |

[1]The nucleotide sequences for the rice genes in this table can be obtained online from the Michigan State University Rice Genome Annotation Project (rice.plantbiology.msu.edu/index.shtml).
See, Ouyang et al. (2007) Nucleic Acids Res. 35:D883-D887.

SEQ ID NO: 2 (SP2) was made as follows. The first set of nucleotide sequences (set of regulatory elements with a selected property) was the putative promoters of 32 virus genomes of the family Caulimoviridae, retrieved from NCBI's Viral Genomes resource (www.ncbi.nlm.nih.gov/genomes/GenomesHome.cgi). These putative promoter sequences are publicly available. There was no second set of sequences; the "simulated background" variant of the position-dependent design algorithm was used. Sequences were taken from 300 bp 5' of the TATA box to 300 bp 3' of the TATA box (i.e. −300 to +300), aligned on the TATA box. Putative TATA boxes were identified from literature references and/or by homology to the 35S promoter of cauliflower mosaic virus. The entire sequence (−300 to +300) was designed by the position-dependent algorithm, with word size k=10, kernel width w=15 (adaptive KDE variant), entropy window width ω=64, pseudocounts ρ=10, frequency weight $\varphi_z$=0.5, and entropy weight $\varepsilon_z$=0.07. Any other parameters were as described above. Any designed sequence with the sequence "ATG" 3' of the expected TSS was rejected post-design.

SEQ ID NOS: 3, 4, and 5 (SP3, SP4, and SP5) were made as follows. The first set of nucleotide sequences (set of regulatory elements with the selected property) was the promoters of 48 Arabidopsis genes that were highly and constitutively expressed according to the published microarray data of Brady et al. (2007) Science 318:801-806, and that had a putative TATA box within ±50 bp of the annotated TSS. (TAIR Arabidopsis genome, version 9 (TAIR9), www.Arabidopsis.org/) A putative TATA box was any sequence matching the pattern TATAWAW (SEQ ID NO:39), where W indicates T or A. The 48 Arabidopsis genes that were used are listed in Table 5. There was no second set of sequences; the "simulated background" variant of the position-dependent design algorithm was used. Sequences were taken from 1000 bp 5' of the publically annotated transcription start site (TSS) to 50 bp 3' of the TSS (i.e. −1000 to +50), aligned on the putative TATA box. The entire sequence (−450 to +50) was designed by the position-dependent algorithm using the corresponding region of the training set of nucleotide sequences, with word size k=6, kernel width w=10 (adaptive KDE variant), entropy window width ω=64, pseudocounts ρ=10, frequency weight $\varphi_z$=0.5, and entropy weight $\varepsilon_z$=0.07. Any other parameters were as described above. Any designed sequence with the sequence "ATG" 3' of the expected TSS was rejected post-design.

TABLE 5

Set of 48 Constitutively Expressed *Arabidopsis* Genes[2]

| | | | |
|---|---|---|---|
| AT1G02780 | AT1G04270 | AT1G07590 | AT1G07770 |
| AT1G07890 | AT1G07920 | AT1G07930 | AT1G07940 |
| AT1G14320 | AT1G15930 | AT1G20440 | AT1G20450 |
| AT1G26630 | AT1G43170 | AT1G52300 | AT1G56070 |
| AT1G66580 | AT1G67430 | AT1G77940 | AT1G78380 |
| AT2G09990 | AT2G19730 | AT2G30870 | AT2G36530 |
| AT2G45070 | AT3G04400 | AT3G09200 | AT3G09500 |
| AT3G09820 | AT3G11940 | AT3G17380 | AT3G18740 |
| AT3G18780 | AT3G52590 | AT3G55440 | AT3G60245 |
| AT4G01850 | AT4G05320 | AT4G09320 | AT4G13940 |
| AT4G33865 | AT4G34110 | AT4G36130 | AT5G02500 |
| AT5G15200 | AT5G19760 | AT5G20290 | AT5G40730 |

[2]The nucleotide sequences for the *Arabidopsis* genes in Tables can be obtained online from The *Arabidopsis* Information Resource (TAIR *Arabidopsis* genome, version 9; www.Arabidopsis.org/).
See, Swarbreck et al. (2008) Nucleic Acids Res. 36:D1009-D1014.

SEQ ID NOS: 6, 7, and 10 (SI1, SI2, and SI5) were made as follows. The first set of nucleotide sequences (set of elements with the selected property) was the first introns of 108 *Arabidopsis* genes that were highly and constitutively expressed according to the published microarray data of Brady et al. (2007) Science 318:801-806. The 108 *Arabidopsis* genes that were used are listed in Table 6. First introns could occur in either the 5' UTR or the coding region, but had to start within 500 bp of the annotated TSS. The second set of nucleotide sequences (background elements) was the non-first introns of all genes in the *Arabidopsis* genome. Non-first introns had to start at least 1000 bp from the annotated TSS. Both sets of sequences included the first and last 150 bp of each intron, plus 10 bp of the surrounding exons. For introns shorter than 300 bp, sequence was duplicated as necessary, but avoiding duplication of splice sites or branch points. The entire sequence was designed by the position-dependent algorithm, with word size k=5, kernel width w=5, entropy window width ω=64, pseudocounts ρ=50, frequency weight $\varphi_z$=5.0, and entropy weight $\varepsilon_z$=150. Any other parameters were as described above. Consensus 5' splice sites (CAG/GT) and 3' splice sites (AG/GT) were added to the ends of the designs manually post-design, if necessary replacing any splice sites that had formed as part of the design process.

TABLE 6

Set of 108 Constitutively Expressed *Arabidopsis* Genes

| | | | |
|---|---|---|---|
| AT1G02780 | AT1G04270 | AT1G04410 | AT1G07590 |
| AT1G07600 | AT1G07770 | AT1G07890 | AT1G07920 |
| AT1G07930 | AT1G07940 | AT1G08830 | AT1G13440 |
| AT1G14320 | AT1G15930 | AT1G20440 | AT1G22840 |
| AT1G26630 | AT1G41880 | AT1G43170 | AT1G47420 |
| AT1G48830 | AT1G49140 | AT1G51650 | AT1G52300 |
| AT1G54410 | AT1G56070 | AT1G65930 | AT1G66580 |
| AT1G67350 | AT1G67430 | AT1G72020 | AT1G76200 |
| AT1G77940 | AT1G78040 | AT1G78380 | AT2G16850 |
| AT2G18020 | AT2G19730 | AT2G20820 | AT2G30860 |
| AT2G30870 | AT2G33040 | AT2G36530 | AT2G37270 |
| AT2G45070 | AT2G46330 | AT2G47115 | AT2G47170 |
| AT2G47730 | AT3G01280 | AT3G04400 | AT3G08580 |

TABLE 6-continued

Set of 108 Constitutively Expressed *Arabidopsis* Genes

| | | | |
|---|---|---|---|
| AT3G08610 | AT3G09200 | AT3G09500 | AT3G09820 |
| AT3G09840 | AT3G10860 | AT3G11940 | AT3G17380 |
| AT3G17390 | AT3G18410 | AT3G18740 | AT3G18780 |
| AT3G48140 | AT3G49010 | AT3G52590 | AT3G52730 |
| AT3G52930 | AT3G55440 | AT3G55750 | AT3G60245 |
| AT4G00860 | AT4G01850 | AT4G05320 | AT4G09320 |
| AT4G11150 | AT4G13940 | AT4G16720 | AT4G27960 |
| AT4G29390 | AT4G33865 | AT4G34050 | AT4G35100 |
| AT4G36130 | AT4G37830 | AT4G38800 | AT4G39200 |
| AT5G02500 | AT5G03300 | AT5G08690 | AT5G14030 |
| AT5G15200 | AT5G18380 | AT5G19510 | AT5G19760 |
| AT5G20290 | AT5G42980 | AT5G48810 | AT5G50850 |
| AT5G53300 | AT5G53560 | AT5G56670 | AT5G60390 |
| AT5G64350 | AT5G65020 | ATCG00830 | ATCG01310 |

SEQ ID NOS: 8 and 9 (SI3 and SI4) were made as follows. The first set of nucleotide sequences (set of regulatory elements with a selected property) was the first introns of 141 *Arabidopsis* genes that were highly and constitutively expressed according to the published microarray data of Brady et al. (2007) Science 318:801-806; Schmid et al. (2005) Nature Genetics 37:501-506; and Kilian et al. (2007) Plant J. 50:347-363. The 141 *Arabidopsis* genes that were used are listed in Table 7. First introns could occur in either the 5' UTR or the coding region, but had to start within 500 bp of the annotated TSS. The second set of nucleotide sequences was the non-first introns of all genes in the *Arabidopsis* genome. Non-first introns had to start at least 1000 bp from the annotated TSS. Both sets of sequences included the first and last 150 bp of each intron, plus 10 bp of the surrounding exons. For introns shorter than 300 bp, sequence was duplicated as necessary, but avoiding duplication of splice sites or branch points. The entire sequence was designed by the position-dependent algorithm, with word size k=7, kernel width w=5, entropy window width ω=64, pseudocounts ρ=50, frequency weight $\varphi_z$=5.0, and entropy weight $\varepsilon_z$=150. Any other parameters were as described above. Consensus 5' splice sites (CAG/GT), 3' splice sites (AG/GT), and branch points (CTAAT) were added to the appropriate locations in SEQ ID NO: 8 manually post-design, if necessary replacing any splice sites that had formed as part of the design process. No modification to the splice sites or branch point of SEQ ID NO: 9 was made post-design.

TABLE 7

Set of 141 Constitutively Expressed *Arabidopsis* Genes

| | | | |
|---|---|---|---|
| AT1G01100 | AT1G02500 | AT1G02780 | AT1G04270 |
| AT1G04410 | AT1G07590 | AT1G07600 | AT1G07770 |
| AT1G07890 | AT1G07920 | AT1G07930 | AT1G07940 |
| AT1G08830 | AT1G13440 | AT1G14320 | AT1G15930 |
| AT1G19910 | AT1G20440 | AT1G22840 | AT1G26630 |
| AT1G31812 | AT1G41880 | AT1G43170 | AT1G47420 |
| AT1G48830 | AT1G49140 | AT1G51650 | AT1G52300 |
| AT1G54410 | AT1G56070 | AT1G57720 | AT1G65930 |
| AT1G66410 | AT1G66580 | AT1G67350 | AT1G67430 |
| AT1G72020 | AT1G76200 | AT1G77940 | AT1G78040 |
| AT1G78380 | AT2G16850 | AT2G18020 | AT2G19730 |
| AT2G20820 | AT2G23090 | AT2G28910 | AT2G30860 |
| AT2G30870 | AT2G31490 | AT2G33040 | AT2G36530 |
| AT2G37270 | AT2G41430 | AT2G45070 | AT2G45960 |
| AT2G46330 | AT2G47115 | AT2G47170 | AT2G47730 |
| AT3G01280 | AT3G02360 | AT3G02468 | AT3G04120 |
| AT3G04400 | AT3G05560 | AT3G08580 | AT3G08610 |
| AT3G09200 | AT3G09500 | AT3G09820 | AT3G09840 |
| AT3G10860 | AT3G11940 | AT3G16640 | AT3G17380 |
| AT3G17390 | AT3G18410 | AT3G18740 | AT3G18780 |

TABLE 7-continued

Set of 141 Constitutively Expressed *Arabidopsis* Genes

| | | | |
|---|---|---|---|
| AT3G48140 | AT3G49010 | AT3G52590 | AT3G52730 |
| AT3G52930 | AT3G55440 | AT3G55750 | AT3G57870 |
| AT3G60245 | AT4G00860 | AT4G01850 | AT4G02890 |
| AT4G05050 | AT4G05320 | AT4G09320 | AT4G11150 |
| AT4G13940 | AT4G16450 | AT4G16720 | AT4G21960 |
| AT4G27090 | AT4G27960 | AT4G29390 | AT4G33865 |
| AT4G34050 | AT4G35100 | AT4G36130 | AT4G37830 |
| AT4G38800 | AT4G39200 | AT5G02380 | AT5G02500 |
| AT5G02960 | AT5G03300 | AT5G08690 | AT5G10980 |
| AT5G14030 | AT5G15200 | AT5G18380 | AT5G19510 |
| AT5G19760 | AT5G20290 | AT5G27850 | AT5G42300 |
| AT5G42980 | AT5G43940 | AT5G46020 | AT5G47200 |
| AT5G47930 | AT5G48810 | AT5G50850 | AT5G53300 |
| AT5G53560 | AT5G54760 | AT5G56030 | AT5G56670 |
| AT5G60390 | AT5G64350 | AT5G65020 | ATCG00830 |
| ATCG01310 | | | |

Example 4

Preparation and Quantitative Root Expression Testing of Functional Variants of Synthetic Promoters or Functional Variants of Synthetic Expression-Enhancing in Stably Transformed *Arabidopsis*

2 variants were made of each of SP3, SP4, and SP5 at each of approximately 90%, 80%, and 70% identity (the % identity of the variants is shown in Table 8). The variants designated "good" maintain a high score in the algorithm disclosed herein while the variants designated "bad" have much lower scores (Table 8). The sequences referred to in Table 8 are set forth in SEQ ID NOS: 21-38. The prediction is that the "good" variants will retain promoter activity while the "bad" variants will not.

To assess the activity of functional variants of the synthetic promoters indicated in Table 8, the variant sequences were synthesized with flanking AscI and RsrII sites, cloned in front of the mGFP5-ER gene in vector pGR716, and transformed into *Arabidopsis* as described in Example 1. For each variant, 12 to 44 T1s were selected as described in Example 1 and visually assessed for GFP expression by fluorescence microscopy. Average expression of each variant was scored by eye using the following scale: "−" for no detectable expression; 1 to 5 "+" s for minimal to very strong expression, respectively (Table 8). Comparable visual expression scores for T2 seedlings from 3 to 6 independent lines of the parent SPs are also shown in Table 8 for comparison. Note that the visual expression scores for the parent sequences can be compared to the quantitative measurements reported in Table 1.

The data in Table 8 demonstrates that sequence variants of synthetic promoters prepared in accordance with the invention retain functional promoter activity in stably transformed plants when they maintain a high algorithm score, but generally do not retain promoter activity in stably transformed plants when their algorithm score is low.

TABLE 8

Expression activity of sequence variants of synthetic promoters

| Variant | SEQ ID NO | % identity | score | Expression |
|---|---|---|---|---|
| SP3 | 3 | | 714.3 | ++ |
| SP4 | 4 | | 731.4 | ++ |
| SP5 | 5 | | 716.7 | ++ |

TABLE 8-continued

Expression activity of sequence variants of synthetic promoters

| Variant | SEQ ID NO | % identity | score | Expression |
|---|---|---|---|---|
| SP3good90 | 21 | 90.5% | 683.8 | ++ |
| SP4good90 | 22 | 90.1% | 713.9 | ++ |
| SP5good90 | 23 | 91.1% | 717.9 | +++ |
| SP3good80 | 24 | 80.4% | 708.5 | + |
| SP4good80 | 25 | 80.2% | 754.9 | ++ |
| SP5good80 | 26 | 81.2% | 702.7 | ++ |
| SP3good70 | 27 | 69.7% | 677.8 | ++ |
| SP4good70 | 28 | 70.3% | 730.0 | ++ |
| SP5good70 | 29 | 71.3% | 661.2 | ++ |
| SP3bad90 | 30 | 89.7% | 249.0 | − |
| SP4bad90 | 31 | 89.9% | 325.9 | − |
| SP5bad90 | 32 | 90.5% | 216.1 | − |
| SP3bad80 | 33 | 80.6% | −11.8 | − |
| SP4bad80 | 34 | 80.8% | −67.7 | − |
| SP5bad80 | 35 | 79.8% | 44.9 | − |
| SP3bad70 | 36 | 69.7% | −127.6 | − |
| SP4bad70 | 37 | 70.3% | −212.2 | − |
| SP5bad70 | 38 | 70.3% | −204.2 | − |

To provide quantitative data on expression in specific zones and tissues from synthetic promoter variants, 12 kanamycin resistant T1s are selected per construct and allowed to set seed (T2 generation). Copy number analysis is performed on excised leaves of the T1s by qPCR. Typically, representative T2 seedlings from the 6 lowest copy number lines of each construct are advanced for further analysis.

To assess expression in root tissues, T2 seedlings from two lines with observable GFP fluorescence are grown in MS media in the RootArray, a device designed for confocal imaging of living plant roots under controlled conditions, and described in U.S. Patent Publication No. 2008/0141585 which is hereby incorporated by reference in its entirety. GFP fluorescence in the meristematic zone, elongation zone and maturation zone is imaged and quantified as described in Example 1. Expression of GFP in aerial tissue of stably transformed *Arabidopsis* is assessed by qRT-PCR as described in Example 1. Visual assessment of GFP expression at the T1 generation is confirmed by quantitative assessment of GFP expression at the T2 generation.

Example 5

Preparation and Quantitative Root Expression Testing of Synthetic Promoter Elements Operably Linked to Native Expression Enhancing Intron Sequences in Stably Transformed *Arabidopsis*

To assess the activity of representative synthetic promoters from Example 1 in the presence of known enhancing introns, the AscI/RsrII promoter containing fragments were cloned into pGR799 and pGR687. pGR799 and pGR687 are derivatives of pGR716 that contain UTR-intron sequences from *Arabidopsis* genes AT4G37830 and AT1G51650, respectively, in front of the mGFP5-ER reporter of pGR716. These intron sequences and their enhancing properties have been previously described (see PCT/US2011/043197, herein incorporated by reference). All subsequent procedures were as described in Example 1.

GFP Expression Index (GEI) in *Arabidopsis* root tissue for four synthetic nucleic acid molecules operably linked to the native enhancing introns were measured and shown in Table 9. GEIs in meristematic cells, elongation cells, and maturation cells were measured.

qRT-PCR was used to measure the relative expression levels of GFP in *Arabidopsis* aerial tissue for five synthetic nucleic acid molecules operably linked to native enhancing introns. The result is shown in Table 10.

Sequences of the native expression enhancing introns and operably linked synthetic introns-native expression enhancing introns are: SEQ ID NO: 13 (IN1); SEQ ID NO: 14 (IN2); SEQ ID NO: 15 (SP1/IN2); SEQ ID NO: 16 (SP2/IN1); SEQ ID NO: 17 (SP2/IN2); SEQ ID NO: 18 (SP3/IN1); SEQ ID NO: 19 (SP3/IN2); SEQ ID NO: 20 (SP5/IN1).

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the non-limiting exemplary methods and materials are described herein.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Nothing herein is to be construed GFP Expression Index (GEI) in Arabidopsis Root Tissue for Four Synthetic Nucleic Acid Molecules Operably Linked to Native Enhancing Introns

| Promoter/intron | Meristematic | | | | | | Elongation | | | | Maturation | | | |
|---|---|---|---|---|---|---|---|---|---|---|---|---|---|---|
| | epi* | cor | end | ste | qc | cap | epi | cor | End | ste | epi | cor | end | ste |
| SP1/IN2-1 | 0.546 | 0.441 | 0.42 | 0.362 | 0.384 | 0.62 | 0.299 | 0.2 | 0.17 | 0.143 | 0.063 | 0.091 | 0.116 | 0.206 |
| SP1/IN2-2 | 0.45 | 0.348 | 0.328 | 0.273 | 0.326 | 0.594 | 0.282 | 0.182 | 0.144 | 0.12 | 0.064 | 0.085 | 0.103 | 0.197 |
| SP2/IN1-1 | 0.061 | 0.051 | 0.044 | 0.025 | 0.266 | 0.537 | 0.089 | 0.015 | 0.009 | 0.007 | 0.115 | 0.083 | 0.085 | 0.203 |
| SP2/IN1-2 | 0.038 | 0.042 | 0.035 | 0.02 | 0.233 | 0.242 | 0.061 | 0.014 | 0.008 | 0.007 | 0.062 | 0.043 | 0.042 | 0.099 |
| SP2/IN2-1 | 0.12 | 0.077 | 0.065 | 0.042 | 0.362 | 0.383 | 0.195 | 0.049 | 0.025 | 0.016 | 0.098 | 0.091 | 0.101 | 0.157 |
| SP2/IN2-2 | 0.156 | 0.102 | 0.083 | 0.047 | 0.551 | 0.618 | 0.222 | 0.042 | 0.022 | 0.015 | 0.138 | 0.092 | 0.098 | 0.144 |
| SP3/IN1-1 | 0.387 | 0.335 | 0.311 | 0.258 | 0.331 | 0.393 | 0.211 | 0.146 | 0.123 | 0.119 | 0.063 | 0.073 | 0.084 | 0.146 |
| SP3/IN1-2 | 0.714 | 0.637 | 0.609 | 0.505 | 0.51 | 0.68 | 0.297 | 0.204 | 0.169 | 0.151 | 0.064 | 0.073 | 0.097 | 0.208 |
| SP3/IN2-1 | 0.672 | 0.599 | 0.55 | 0.438 | 0.563 | 0.726 | 0.341 | 0.234 | 0.192 | 0.164 | 0.074 | 0.08 | 0.106 | 0.208 |
| SP3/IN2-2 | 0.218 | 0.198 | 0.178 | 0.141 | 0.152 | 0.185 | 0.105 | 0.075 | 0.062 | 0.053 | 0.029 | 0.03 | 0.036 | 0.063 |
| SP5/IN1-1 | 0.458 | 0.502 | 0.463 | 0.307 | 0.396 | 0.365 | 0.231 | 0.188 | 0.157 | 0.125 | 0.052 | 0.062 | 0.085 | 0.158 |
| SP5/IN1-2 | 0.312 | 0.279 | 0.26 | 0.193 | 0.266 | 0.316 | 0.135 | 0.106 | 0.088 | 0.072 | 0.031 | 0.035 | 0.047 | 0.095 |
| CaMV35S | 0.396 | 0.282 | 0.236 | 0.229 | 0.957 | 1 | 0.24 | 0.083 | 0.084 | 0.195 | 0.235 | 0.216 | 0.31 | 0.545 |

TABLE 10 qRT-PCR Expression Data in *Arabidopsis* Aerial Tissue for Five Synthetic Nucleic Acid Molecules Operably Linked to Native Enhancing Introns

| Promoter/intron | Relative Expression |
|---|---|
| SP1/IN2-1 | 21.0 |
| SP1/IN2-2 | 21.4 |
| SP2/IN1-1 | 10.9 |
| SP2/IN1-2 | 6.3 |
| SP2/IN2-1 | nd* |
| SP2/IN2-2 | 2.6 |
| SP3/IN1-1 | 2.4 |
| SP3/IN1-2 | 7.8 |
| SP3/IN2-1 | 1.2 |
| SP3/IN2-2 | 11.0 |
| SP5/IN1-1 | 2.1 |
| SP5/IN1-2 | 2.9 | nd = not determined

These data demonstrate that the activity of synthetic promoters designed by the methods described herein can be increased by operably linking enhancing introns to their 5'-UTR sequences (compare Tables 1 and 2 to Tables 8 and 9).

as an admission that the present invention is not entitled to antedate such publication by virtue of prior invention.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

| SUMMARY OF SEQUENCES |
|---|

```
>SEQ ID NO: 1 (SP1)
        aa ataggttttt tctcccccca cggcccacca cggcccacct aggcccaccc    60
taaaaaaacc ctaggtgggt gggcccattt tttttttttt tttttttttt ttaggtgggg   120
tgggccgtgg ggggaggtgg gccgtgggcc catgaaaaaa aaaaaatagg gttgggccca   180
cctaaaaaaa aaaccctagg gtgggcccaa aaaaaaaaaa aaaaatgggc ccaccctata   240
gggttttttt tttttttaag agtccggact tccagaagaa taataatctc ggcccacgtc   300
taaaaaagaa accacccatc cgtccatggg cccacctcag accggcccac caagacaaag   360
cccaccaacg gtgggccggc ccattggttc acagtcacgg cccacggccc acccggccca   420
ccgctctata aaccctatat aagaaaccct ccacctcctc gccctcttgg tttcctccct   480
cttccgccgc acacacccac ccagagat                                     515

>SEQ ID NO: 2 (SP2)
        gc tagcgcttat ggagcgtgat ggactgaaag agaccnctac cacgtgttga    60
cgtaagcaat gacataaaac cgatcctaat ctctcctacg aacgacagcg gagagtactg   120
ctgaaagcta tgcttttatt tttctttatt tttctcgtca gtggaataca cgttttgtcg   180
gtgtgtgtcc ttttccaaag aaagacggaa ctgcctagga caacgtcggc taccaaagca   240
caatgtaaag tagacatgat gatcgacgac gtcatgcatg acgtttaaca tgcattgtat   300
gtgtccgtca gtctataaat aggtcaagaa caaacatcga gaaaaggcag aggcgaaata   360
cccatctgcc tatctctcaa gaaataactc tctcttgttc ttcatccttt ctttcatagt   420
ttaaaaacct gaaattgggc aagccccata ggcattttgg tatcagagcg agtaaggaca   480
agtaggtaag tccctaaaat acttctatca ataaaatttc tacgccaaga agggtaagtt   540
gtacgtttat cctacaccct tgtgtttgta accaggcttg gtcaagtgca caagggtatt   600
tgagtccc                                                           615

>SEQ ID NO: 3 (SP3)
        aa cataacttgt atatttaaac ataaagataa accttcttag agagaacata    60
tttaaattgt gttatccatt acttttaata aggaaatata atcttttcag tttgaattga   120
aaataacttt atcaaaattt atgacaaata caaataaaaa ccaaaacaaa aaaagaattg   180
tgtatatgtt attgagaaac gattttatt cactcgtaca tgattcatag aaaattttaa    240
tttagtataa aaagtataaa tataatatta atcaaataaa ttcttatgaa ataaataaat   300
tcttcttcaa gggtaaatga aaccttatga gtaaagtcta ttctgcactt aaaagaaaag   360
agaattgagt atttttgga agcccatttg ggcccatttt aaaatataat aaagaaagcc    420
caataatgag aattaaaaac cctagttttt ttccctcct atataaatcg acattttgtt    480
cgttccttct cttctcttct cttcctct                                     515

>SEQ ID NO: 4 (SP4)
        aa attgttgata gaatttcaaa cataacataa cttaacatga aatcttaatt    60
aattatcaga aatacgatca ctatcatccg attttgtctt ttcgatttta ttaattttca   120
actaaaacat ctcaacagat aaaacaaaac cactttgttg ataatccaat attttaattt   180
tattgagaag atgatatgat aaagtataca gttatataca aaatgttttc tgcatatttc   240
caattttgtc aaatgtcact tttaagtgtc aaacactaat aaataaaat aaaataaata    300
atacttggat taatgagtaa aaaaatgggc ctaaacaaat tatatcacta aaaagtaatt   360
tagaaattca taattggccc atttgaccga gttttaaag ctaaaatttt aaaggcccaa    420
aacccttatt agggtttcaa cagaaaccta taaggagact ctatataaac cctctcttcg   480
ttcattaggg tttctccttc tctgaaga                                     515

>SEQ ID NO: 5 (SP5)
        ac atttcggtta tctgggtact acataaagat tgccaagtcc attgattgaa    60
ttgtgtgtgt ttttatggct cacttatacg ttgtctttt taacaaaaaa tgttttcaac    120
taatttgaat tttgtttaca aacaaataca aataaccatt ggtttctcaa gaatcaatca   180
agaattagaa atgatatgat agattttctca ataaagaca aaattttcaa ttttttcagt    240
ttttgtaaat ctacagcatc atttgtgata tgtctatcaa attttgctta aataaataaa   300
tcctcaaata ctttgaatga gtaaaaatga aataattagg cttacatagt aattaaaatag   360
gcttcaaaaa ggctaaggcc caaatttgtt aaattaagaa ttgaagtcca aaaacctatg   420
ttaaaacaat ctaggttagg gtttcttctc tcctatatat tctataaact aggtcattcc   480
attcgtcaaa ctcctctctt gcaaactc                                     515

>SEQ ID NO: 6 (SI1)
caggtaagtt tctcttcttc agctcttctt cttcttcttg gatctcgatt ttcgtgtaca    60
tttcgtagtt cgatctgatt ttcgttgttg atctagattc ttgcgatttg ggttttgttg   120
tgttgataat tttottagtg atctgataga ttgtttatag tgtttcagat tgtttagaaa   180
tcttctatga atttaggttt gatcggtttc ttgatcgatt tgatgatttc tatcaattga   240
ttagtggatc tgttttgttg tgatttctaa tattgatctg ttttgtttgc tttttttcga   300
tgcaggt                                                            307

>SEQ ID NO: 7 (SI2)
caggtaaaat ttctcctctc ctttcctctc tctcttctga ttctgatttc gttttcgctc    60
gatttggatc gtatttgtcg ttagttttta atcgtttgga ttcttggttg gtgtttgttt   120
gaatttcag ttgtagatct ttatagatct ctgtgtttta tgcatttaca tttaagattt    180
tagaaattgt tctagattgg tcttttttgtt tagattcatc tgatcaattc aatgattgat   240
tgtttgaatt gtgatttgat aagtttctac ttgatctgt atattgattt gtttgttcct    300
tgcaggt                                                            307

>SEQ ID NO: 8 (SI3)
caggtttaca tctttattcc ttgtgttctc ttatacttga atctttcatt ttggttttcg    60
atttgggttt ttcgatttgt ttagattaat ctgatttgag ctgtgtttat cattgtttcg   120
atctgtgata ttgaccaaat gatttgtgtt ttggttttct tagcttgtat tattattgat   180
```

SUMMARY OF SEQUENCES

```
tgaattcatt tcccattgat atttcgtttc tttttagcat tccaatctcc attgtttttt      240
ctgattatgc ttgtggatct ttacattttc aaaactttgt ggtctaatgt ttttttggtt      300
taggt                                                                  305

>SEQ ID NO: 9 (SI4)
tcaaggtact actttctcat ccctotttca tacttttatt ctcttttgca ttttgatttg       60
gttttactct gagttttcta tctctcgatc tttgatttaa tctaattagg ttttttctag      120
atctagatct agatttgaaa atttaatagc tgttggtctt ccttgatttt tgtttagctt      180
gagtttatg tatagaatgg tgtttctctt tgaatctgtt gcatttctct tatgaatctg       240
attaatcttt tgatttgtgt ttatcgtttc ttaaataaac ttgttgtttg gttttgagtt      300
tgcagagagg                                                             310

>SEQ ID NO: 10 (SI5)
caggtaaact tttcttctcc tcttctagat ctctcttctc tcgatttctg aattatttcg       60
taatttccga tctctgattt ttggtgttag attttgtttt ctgtgatcga tttgatttga      120
ttttcagttg tagagtaaag cttgtttgtt gtttgagggt tagatatatc agattatgat      180
ttccgatatt gttgtttctc tgtttcgttt tgattcatca tottatcgt ggatttagat       240
tatttagtgt gattcgtatg tactctgatt gaatttgtgt gatctttgtg tttggttttt      300
gtgcaggt                                                               308

>SEQ ID NO: 11 (AT4G37830 promoter)
tgcgagtggg cgaattccgg agcactctga ttggctgaaa aaatagaaat agtagtgatg       60
ttgctcctcc tctcctcctc tattattaat ttttcgtcgt tottcttctg aaagttgtgt      120
ggttttaga ggtcaccaaa aaaaatctat tttgagatac ttaaaaatatt tcgttttgca      180
ttttgttgtg cagccatttg ttacacaggt tgaagcttat aactgaaaat tggattcaaa      240
gaatcgtaga tgaagaaatc gaagtgagtt gaatattttc tgaacatatg aaaattggaa      300
caagttttt ctcattttgc tagtttcctg ttttttatgtt ttcttgactt taggagatga      360
catatggagg tgaactatac aaaggttgtt gcaacgataa cattctcctt aattcagttt      420
ttgcaactcg gttacaagca ctcagtggac ttttggccaa gacaattttt ttttttttt      480
ctctctctct aaaatgttat agatacgaat cctttgttga ataaaggaaa aagttgaaca      540
tttgattaca cataagactt taacataatc caacttttttt ttatatgaag ctacaaacaa      600
gatttaaaac atcaaagatt ccatctaaac ttcattcatc ttcaatcttc aacatccttc      660
aatgactagt atgtatgtac ataagtaaaa ttgttgataa gaaaacaaaa caatgatggg      720
ctaaaatagc ccataaaagg cccattaaac ttgggtttag actttagatt caacgacgcc      780
agattagtga gtcacataac cctcttggaa agagtctcaa cacttgcaga gaaaagaac      840
aaggaagatc ccggaaa                                                      857

>SEQ ID NO: 12 (AT1G51650 promoter)
ggaggaggat atgattgttg cttcaacaac tatatatgga tttgataaca atccttatc       60
ctcggaagat aaaccaaatt tottaccaaa cccaccaaaa taagtaatta ccagtgttct      120
tcttcaaag acttctataa accaaaacaa gatcacatat aatcattaac ttaaagcaaa      180
acccaaagtc ttgttttatt tgttagtcag ctcaaccatc tttatctgaa actaaactgt      240
ttctctcttc tttgttctg acaagtcaat gagattggtg tcttctctct gttgcacatt      300
taatattaac ttttgaaaaa ctacaaaacg aaacaaaaca aagaaaagca gacatttaca      360
cgaaattatg cagacatata cacgaaattc aatctacctg aaaatgagaa taagttttga      420
gtaaatttcg tggagactcc tggaaataag tttgttgtt ttcctatttt tatgtaactt       480
cgcttaaatt tctaattgcc taatcaaggt attaaaatag caaagcttgg tttggctcag      540
tcttcgcgta aactccaaga aacaatcata aaaacaaata aaaagacaa gaaaccaaaa      600
aaaaaaaaaa agttgagaga tttcagtaga tgaaagttgg atagaagatt cgtgtagtta      660
gctacttaat gggccgttaa aatatttaat aaggccgcatt gggtctaaac tgtgttagga      720
ttactagggc acagaatcgg tctctgtccc atttcgcgaa cttctcccctt agaatcggaa      780
cggacgaaga aggaagacaa ggaagaagat cggag                                 815

>SEQ ID NO: 13 (IN1)
cagtgagtcacataaccctcttggaaagagtctcaacacttgcagagaaaaagaacaaggaagatcccggaaacagg
taatttctctcctctctattttaccattttccattgacgacgatctaggttttctgatttgattttggagaacgcc
tcgatgagtttatagattcgtagattggttttgagattcagtatatttcaccggattccaatttttgaaccgata
cctaatttttgaatgatttggtagatcggattggtcaaatttgaaattgattttctccataatatctgaagcgtctt
attggatcaaatctacaacatttctctgttgaaaggatcgattttttttttcttggaacatgataacttttgattat
tcatcaaagttttgttcttttttaatatttcacaggt > SEQ ID NO: 14 (IN2)
cagatttcgcgaactttctccttagaatcggaacggacgaagaaggaagacaaggaagaagatcggaggtaagcctt
ttcgatcctttaatcgtcgatgttggatcttagatctggattcttcacgttcttgtgttctcgattcctgatttgtt
tttgagtaatttgttggaataatctgatttcctaaaagttatcggaattaagtggaaagtgaatcatctgcttctgg
atttgatcttcgattttgcatttaaccttcctctgcttctggatttgatcagtttcaatactatcttcatacaatgt
tgttatgtccaaattgttgaattttttcattagagttagcttcagagaaaacaacaaaactagtagtatgtgtgaaa
caagaacatgaagaagatggaaagctgattgggaacattgcatttagatgtcttttctcgtttatgtttggatctca
attcttcatgttcttgtgtgtcattgaaattgttggaatacgtagatatcagagtaggtcattttgggaaagct
attgaatttaagaggaagatgaatcattttaacaagctccatcgatttgcgcttaatctgtctctcttctgcttct
ggatttgattaatttcattctattttgttttctcataagttgttgttatgttcaaattgttgaatttggaatgattt
catttctcaaataggggtttactgagacaatgattccagatttagtctatctgaaaatggttcagcttttcttcttgtt
gatccatttgtctaacattctctcatgtttttgttttttccttgacaggt > SEQ ID NO: 15 (SP1/IN2)
aaatagggttttctccccccacggcccaccacggcccacctaggcccaccctaaaaaaaccctaggtgggtgggcc
cattttttttttttttttttttttaggtggggtgggccgtggggggaggtgggccgtgggcccatgaaaaaaaa
```

| SUMMARY OF SEQUENCES |
|---|
| aaaatagggttgggcccacctaaaaaaaaaacccctagggtgggcccaaaaaaaaaaaaaaaaatgggcccaccctat<br>agggttttttttttttttaagagtccggacttccagaagaataataatctcggcccacgtctaaaaaagaaaccacc<br>catccgtccatgggcccacctcagaccggcccaccaagacaaagcccaccaaccggtgggccggcccattggttcaca<br>gtcacggcccacggcccacccggcccaccgctctataaaccctatataagaaaccctccacctcctcgccctcttgg<br>tttcctccctcttccgccgcacacacccacccagagatcggaccgcagatttcgcgaactttctccttagaatcgga<br>acggacgaagaaggaagacaaggaagaagatcggaggtaagccttttcgatcctttaatcgtcgatgttggatctta<br>gatctggattcttcacgttcttgtgttctcgattcctgatttgttttttgagtaattgttggaataatctgatttcc<br>taaaagttatcggaattaagtggaaagtgaatcatctgcttctggatttgatcttcgattttgcatttaacctttcc<br>tctgcttctggatttgatcagttcaatactatcttcatacaatgttgttatgtccaaattgttgaattttcattta<br>gagttagcttcagagaaaacaacaaaactagtagtatgtgtgaaacaagaacatgaagaagatggaaagctgattgg<br>gaacattgcatttagatgtcttttctcgtttatgtttggatctcaattcttcatgttcttgttgtgtgtcattgaaa<br>ttgttggaatacgtagatatcagagtaggtcattttgggaaagctattgaatttaagaggaagatgaatcattttaa<br>caagctccatcgattttgcgcttaatctgtctctcttctgcttctggatttgattaatttcattctatttttgtttc<br>tcataagttgttgttatgttcaaattgttgaatttggaatgatttcattctcaaatagggtttactgagacaatga<br>ttccagatttagtctatctgaaaatggttcagctttcttcttgttgatccatttgtctaacattctctcatgttttt<br>gttttccttgacaggt |

> SEQ ID NO: 16 (SP2/IN1)
gctagcgcttatggagcgtgatggactgaaagagacccctaccacgtgttgacgtaagcaatgacataaaaccgatc
ctaatctctcctacgaacgacagcggagagtactgctgaaagctatgcttttattttctttattttctcgtcagt
ggaatacacgttttgtcggtgtgtgtccttttccaaagaaagacggaactgcctaggacaacgtcggctaccaaagc
acaatgtaaagtagacatgatgatcgacgacgtcatgcatgacgtttaacatgcattgtatgtgtccgtcagtctat
aaataggtcaagaacaaacatcgagaaaaggcagaggcgaaatacccatctgcctatctctcaagaaataactctct
cttgttcttcatcctttctttcatagtttaaaaacctgaaattgggcaagccccataggcattttggtatcagagcg
agtaaggacaagtaggtaagtccctaaaatacttctatcaataaaatttctacgccaagaagggtaagttgtacgtt
tatcctacaccttgtgtttgtaaccaggcttggtcaagtgcacaagggtatttgagtccccggaccgcagtgagtc
acataaccctcttgaaagagtctcaacacttgcagagaaaagaacaaggaagatcccggaaacaggtaatttctc
tcctctctatttttaccattttcattgacgacgatctaggttttctgatttgattttggagaacgcctcgatgagt
ttatagattcgtagattggttttgagattcagtataatttcacccggattccaatttttgaaccgatacctaatttt
gaattgatttggtagatcgattggtcaaatttgaaattgattttctccataatatctgaagcgtcttattggatca
aatctacaacatttctctgttgaaaggatcgatttttttttttcttggaacatgataacttttgattattcatcaaag
ttttgttctttttaatatttcacaggt > SEQ ID NO: 17 (SP2/IN2)
gctagcgcttatggagcgtgatggactgaaagagacccctaccacgtgttgacgtaagcaatgacataaaaccgatc
ctaatctctcctacgaacgacagcggagagtactgctgaaagctatgcttttattttctttattttctcgtcagt
ggaatacacgttttgtcggtgtgtgtccttttccaaagaaagacggaactgcctaggacaacgtcggctaccaaagc
acaatgtaaagtagacatgatgatcgacgacgtcatgcatgacgtttaacatgcattgtatgtgtccgtcagtctat
aaataggtcaagaacaaacatcgagaaaaggcagaggcgaaatacccatctgcctatctctcaagaaataactctct
cttgttcttcatcctttctttcatagtttaaaaacctgaaattgggcaagccccataggcattttggtatcagagcg
agtaaggacaagtaggtaagtccctaaaatacttctatcaataaaatttctacgccaagaagggtaagttgtacgtt
tatcctacaccttgtgtttgtaaccaggcttggtcaagtgcacaagggtatttgagtccccggaccgcagatttcg
cgaactttctccttagaatcggaacggacgaagaaggaagacaaggaagaagatcggaggtaagccttttcgatcct
ttaatcgtcgatgttggatcttagatctggattcttcacgttcttgtgttctcgattcctgatttgttttgagtaa
tttgttggaataatctgatttcctaaaagttatcggaattaagtggaaagtgaatcatctgcttctggatttgatct
tcgattttgcatttaacctttcctctgcttctggatttgatcagttcaatactatcttcatacaatgttgttatgtc
caaattgttgaattttcatttagagttagctcagagaaaacaacaaaactagtagtatgtgtgaaacaagaacat
gaagaagatggaaagctgattgggaacattgcatttagatgtcttttctcgtttatgtttggatctcaattcttcat
gttcttgttgtgtgtcattgaaattgttggaatacgtagatatcagagtaggtcattttgggaaagctattgaattt
aagaggaagatgaatcattttaacaagctccatcgattttgcgcttaatctgtctctcttctgcttctggatttgat
taatttcattctatttttgtttctcataagttgttgttatgttcaaattgttgaatttggaatgatttcattctca
aatagggtttactgagacaatgattccagatttagtctatctgaaaatggttcagctttcttcttgttgatccattt
gtctaacattctctcatgttttttgttttccttgacaggt > SEQ ID NO: 18 (SP3/IN1)
aacataacttgtatatttaaacataaagataaaccttcttagagagaacatatttaaattgtgttatccattacttt
taataaggaaatataatcttttcagtttgaattgaaaataactttatcaaaatttatgacaaatacaaatAAaaacc
aaaacaacaaaagaattgtgtatatgttattgagaaacgattttattcactcgtacatgattcatagaaaattta
atttagtataaaaagtataaatataatattaatcaaatAAattcttatgaaatAAatAAattcttcttcaagggtaa
atgaaaccttatgagtaaagtctattctgcacttaaaagaaaagagaattgagtattttttggaagcccatttgggc
ccatttaaaatataataaagaaagcccaataatgagaattaaaaacccagttttcttccctcctatataaatcg
acattttgttcgttccttctcttctcttctcttcctctcggaccgcagatttcgcgaactttctccttagaatcgga
acggacgaagaaggaagacaaggaagaagatcccggaaacaggtaatttctctcctctctattttaccattttc
cattgacgacgatctaggttttctgatttgattttggagaacgcctcgatgagtttatagattcgtagattggtttt
gagattcagtataatttcacccggattccaatttttgaaccgatacctaattttgaattgatttggtagatcgattg
gtcaaatttgaaattgattttctccataatatctgaagcgtcttattggatcaaatctacaacatttctctgttga
aaggatcgatttttttttcttggaacatgataacttttgattattcatcaaagttttgttctttttaatatttcac
aggt > SEQ ID NO: 19 (SP3/IN2)
aacataacttgtatatttaaacataaagataaaccttcttagagagaacatatttaaattgtgttatccattacttt
taataaggaaatataatcttttcagtttgaattgaaaataactttatcaaaatttatgacaaatacaaatAAaaacc
aaaacaacaaaagaattgtgtatatgttattgagaaacgattttattcactcgtacatgattcatagaaaattta
atttagtataaaaagtataaatataatattaatcaaatAAattcttatgaaatAAatAAattcttcttcaagggtaa
atgaaaccttatgagtaaagtctattctgcacttaaaagaaaagagaattgagtattttttggaagcccatttgggc
ccatttaaaatataataaagaaagcccaataatgagaattaaaaacccagttttcttccctcctatataaatcg
acattttgttcgttccttctcttctcttctcttcctctcggaccgcagatttcgcgaactttctccttagaatcgga

| SUMMARY OF SEQUENCES |
|---|
| acggacgaagaaggaagacaaggaagaagatcggaggtaagccttttcgatcctttaatcgtcgatgttggatctta<br>gatctggattcttcacgttcttgtgttctcgattcctgatttgttttgagtaatttgttggaataatctgatttcc<br>taaaagttatcggaattaagtggaaagtgaatcatctgcttctggatttgatcttcgattttgcatttaacctttcc<br>tctgcttctggatttgatcagttcaatactatcttcatacaatgttgttatgtccaaattgttgaatttttcattta<br>gagttagcttcagagaaaacaacaaaactagtagtatgtgtgaaacaagaacatgaagaagatggaaagctgattgg<br>gaacattgcatttagatgtcttttctcgtttatgtttggatctcaattcttcatgttcttgttgtgtgtcattgaaa<br>ttgttggaatacgtagatatcagagtaggtcattttgggaaagctattgaatttaagaggaagatgaatcattttaa<br>caagctccatcgattttgcgcttaatctgtctcttctgcttctggatttgattaatttcattctatttttgttttc<br>tcataagttgttgttatgttcaaattgttgaatttggaatgatttcatttctcaaatagggtttactgagacaatga<br>ttccagatttagtctatctgaaaatggttcagctttcttcttgttgatccatttgtctaacattctctcatgttttt<br>gtttttccttgacaggt |

> SEQ ID NO: 20 (SP5/IN1)
acatttcggttatctgggtactacataaagattgccaagtccattgattgaattgtgtgtgttttatggctcactt
atacgttgtctttttaacaaaaaatgttttcaactaatttgaattttgtttacaaacaaatacaaataaccattgg
tttctcaagaatcaatcaagaattagaaatgatatgatagatttctcaataaaagacaaaattttcaattttttcag
tttttgtaaatctacagcatcatttgtgatatgtctatcaaattttgcttaaataaataaatcctcaaatactttga
atgagtaaaaatgaaataattaggcttacatagtaattaaataggcttcaaaaaggctaaggcccaaatttgttaaa
ttaagaattgaagtccaaaaacctatgttaaaacaatctaggttagggtttcttctctcctatatattctataaact
aggtcattccattcgtcaaactcctctcttgcaaactccgaccgcagtgagtcacataaccctcttggaaagagtc
tcaacacttgcagagaaaaagaacaaggaagatcccggaaacaggtaattctctcctctctatttttaccattttc
cattgacgacgatctaggttttctgatttgatttggagaacgcctcgatgagttttatagattcgtagattggtttt
gagattcagtataatttcaccggattccaatttttgaaccgatacctaattttgaattgatttggtagatcgattg
gtcaaatttgaaattgatttttctccataatatctgaagcgtcttattggatcaaatctacaacatttctctgttga
aaggatcgatttttttttttcttggaacatgataacttttgattattcatcaaagttttgttcttttaatatttcac
aggt >SEQ ID 21 (SP3good90)
TAAATAAATTGTCTTTGTCAACATAAAGATAAACCTTCTTAGAGAGAACATATTTAAATTTTGTTATCCATTACTTT
TAATAAGGAAAAAATATCTTTTCAGTTTGAATTGAAATCCACTTCAACCACGCTTTTGACAAATACAAATCCAAACC
AAAACAACAAAAGAATTGTGTATATGTTATTGAGAAACGATTTTTCTTCACTCGTACATGATTCGTACAAAAATCTA
ATTTAGTATAAAAAGTATATATAATATTAATCAAATAAAGTCTTATGAAATAAATACATTCTTCTTCAAGGGTAA
ATGAAACCTAATGAGTAAAGTCTATTCTGCACTTCAAAGAAAATAGAATTGGGTATTCATGGGAAGCCCATTTGGGC
CCATTTTAAAATGGGGCAAATAAAGCCCAATAATGAGAATAAAAAACCCTAGTTTTCTTCCCCTCCTATATAAATCG
ACATTTCATTCGTTCCTTCTCTTCTCTTCTTTT >SEQ ID 22 (SP4good90)
AAATTGTTGATAGAATTCCGAACAGAACATAACTTAACTTGAAATATAAATCAATTATCAGAAATACGTTCACGTTC
ATCCGATTTTGTCTTTTCGATTGTATAACTTGTCAACTTCGACATCTCAACAGATAAAACAAAACCACTTTGTTGAG
AATCCAAAACTAGGTTTTGATTGAGAAGATGATATGATTCAGAATACAGTTATATACAAAATGTTTTCTGCATATTT
CCAATTTTGTCAAATGTCACTATTCATTGTCAAACACTATTCAATTAAATTAGATGAAACAATACTTGGATTAATGA
GTTAAAAAATGGGCCTAAGTTAGTTATATCACTCAAAAGTAATTGAGCAATTCATAATTGGCCCATTTGACCGAGTT
TGTAAAGCTAAAATTTTAAAGGCCCAAAACCCAGATTAGGGTTTCAACAGAAACCTATAAGGAGACTCTATATAAAC
TCTCTCTTCGTTCATTAGGGTTTCTCCTTCTCTGAAGA >SEQ ID 23 (SP5good90)
ATTGCTGGGTTATCTGGGTACTACATAAAGATTGCCAAGTCCATTGATAGAATTGTGTGTGTTTTGATGGCTCACTT
ATACGTTGTCTGTTCTAACAAAATATGTTTGCAACTAACTTCGATTTTATGAACAAACAGATACAAATAACCATTGG
TTTCTCAAGAATCCTTCAAGAGTTAGAAATGATATGATAGATTTCTCAATAAAAGACAAAATTTTACAGTTTTTCAG
TTTTTGTAACTCTACAGCATCACTTGTGATATGTCTATCAAATTTCGTTTGACTAAATAAATCCTCAAATACTTTGA
ATGAGTAAAAATGAAATAATTAGGCTTAAGTAGTAATTTGATAGGCTTCAAAACGGCTAAGGCCCAAATTTGTTAAG
TTAAGAATTGAAGTCCAAAGCCCAATATTAAAACAATCTACCCTAGGGTTTCTTCTCTCCTATATATTCTATAAACT
AGGTCTTCCCATTGGTCAAACTCCTCTCTTGCAAACTC >SEQ ID 24 (SP3good80)
TTCCAAACTTGTATGTTAGAACATAACATAAAACCTACTTAGAGAGAGAATTGCATGTGATTGTGATCCATTACTTT
TATCTGCGAAATCCGATTTTTTCAGTTTGAATTGAATGTTACTTTATGACATCTTGACAAACACAAAATTTCGCC
AAAACAACAAAAGAATTGTGTATAGGTTTTTGAGAAACGATTTTGGTGCTCTCGTACATGATTGGATGGAAAATTAA
ATTTAGTATAAAAAGTGTCACTATAATATGTGCCAAACATATACTTATGAAATAAATAAATTCTTCTTCAAGGGTAA
ATGAATCCTAGTTGGTTAACGCAATTCTGCACTAGATAGAAAGGCCTATTGAGTATTGATGGGAAGCCCATTTGGGC
CCATTTTAAGTTAAGCTAAGGAAAGCCCAATAGTGAGAATAAAAAACCCTAGTTTTCTTCCCCTCCTATATAAATCG
ACATTTTGTTCCTTCGTTCACTTCTCTTCTCTTCCTCT >SEQ ID 25 (SP4good80)
TAATTGTTGAGAGAATCCATAACATAACATAACATTACAAGAATTCTGGTTCAAATTGGAGAAATACTTTAGCTGTT
TTCTGTTTTTGTCTTTTCGATTGTTTCAGTTTTCAACTTGAACATCTCAACAGATAAAACGTAACCAACTTGTTG
AGAATCCAATAAAAGAATTTGTTTGAGAAGATGATATGATAGATAAAACAGTTATACTCAAAATGTTTTCTGCATAT
TTCCAATTTTGTCGAATGTCACTATAAAGTGTCAAACACTAAAGACAGATAAATAAATAATGATTACTTGGATTGAG
GAGCAAAAATTTGGGCCTAAACGCATTAAAAACCTCCCTATCAAGGCCCAAGATCATTATTGGCCCATTTTACCGAG
TTTATTAAGCTAAAATTTTAAAGGCCCAAAACCTATATTAGGGTTTCAACAGAAACCTATAAGGAGACTATATATAA
ACTCTCGTCTCGTTCATTAGGGTTTCTCTTGCTCATAAGA >SEQ ID 26 (SP5good80)
ATGTCTGTGTTATCTGGGTACTACATAAAGAGGCCCAAGTCAATTGAGAGAACTGTGTGTGTGTTGATGGCTCACTT
CTACGTTGAGTTTTTTAACAAAAAATCATTTCAACTAGTTTGAATTTAACAAACAAACAGATAGAAATAACCATTGG
TCTCTCAAGAATCATTCAAGTATAGAAGATGATATGATAGATTTCTCTACCAAAGACAAAATTGTCGTATTTGTCAG
TTTTTGTAAATCTACAGCTTCATTTGTGATATGTCTATCAAAGCTTGAATAATTAAATTTTTCCTCAAATCCTTGGC

| SUMMARY OF SEQUENCES |
|---|
| CTGAGTAAAAATGAAAAGAAAAGGCTTACATAGTAATTTTATAGGCTTAGATGGGCCTAAGGCCCATTATTGTAAGT<br>TAAAGAATTGAAGCCCAAACCCTAGAATTAAAACAATCCATATTAGGGTTTTGCCGCACCTATATATTCTATAAACT<br>AGGTCAACTCTTTCGTCGAACCCTTCTCTTGCAAACTC |
| >SEQ ID 27 (SP3good70)<br>ACGAGACTTTGTTTTGAGTGAGTTGAAGATAAACGTTGAGATAGAGAGATGTGTGTGTTTTTTATCCATCACTTA<br>GCCAAATGCACAAAAATGTTTTCAGTTTGAATTGGACTTCGCTTTTCCATCCTTGTTGACAAATACAAATATAATCC<br>AATACAAAACGATCAGAATTAGTTTTCCTTTTAGAAACGATTTAGATTCTCTCGTACATGATTGGAGACAACATCCA<br>ATTTAATAAACAAAGTAATTCATTGTTACTATTCAAACACAGCCGTGAGAGATAAATACATTCTTCTTCAAGGGTAA<br>ATGAAAGCCAATGAGTTAAGTCTATTCTGCACTAAAAGCAAAATAGAATTGGGTATTGACCGGAAGCCCATTTGGGC<br>CCATTTTAATTCTCACCAATAACGGCCCAATATTGAGAATTAAAAACCCTAGTTCTCTTCCCCTCCTATATATATCG<br>ACATCGCTGCCATTCGTTCCTCTCTTCTCTTCTCTTCC |
| >SEQ ID 28 (SP4good70)<br>CCATTGTTGAGAGAATCCATAACATAACTGTGACTTAACTGATCTTCCTGTGAGTGAAATACTTATCACTTC<br>ATCCGATTTTGTTTTTGCGATAGTAGTTACTCTCAACTTCGACATCTCAACAGATAAGATAATACAGAAATAGTGAG<br>AATCCAAAACGAACATCAGTTTGAGAAGATGATATGATAACAAGTACAGTTGAAGTGAAAATCTTTTCTGCATTTTT<br>AAAATCTTCACGAATGTCACTAATCTATGTCAAACACTATTCACTGAAATACGATTTGGTGATACTTTGAGGAAGGG<br>GTTAAAAAATGGGCCTAAACTCTAAAACACACTAAAAAGGCGTTTAATAGGCCATAATTGGCCCATTGGGTCGAGTA<br>TTTTAAGTTAAGGCCCAAAAGGCCCAAACCCTAAATTAGGGTTTCAAACCTAGCCTATAAGGAGACTCTATAAAAAC<br>CCGCCTCTCGTTCATTAGGGTTTCTCTTCTTCTGAAGA |
| >SEQ ID 29 (SP5good70)<br>ACTTTTCCGTATTCTGGGTACTTCAGTAAGATTGCCAAGTCCAGATAGAGAACTGAGTGTGTGTTGATGGCTCACTT<br>ATACGTTTTCTGTTTTAACAGAGAAAAATTTCAACTTGAGTGAATGTACGAAATCAACAGATACATAGATTCATTGG<br>TCTCTCAAGAATAATCAAAATATAAGGAATGATATGTTAGATTTTTCTCATAGATTCAACTTTTACATTTTTGTCAG<br>TTTTTGTTCCTCTACAGCACCACGCGTGTTTTGTGTTTCAAAGTCTTTATGATTAAATCCTCCCACAAATCCTTTAA<br>ATGAGTAAAAAGCAACGTAAAGGCTTTAGTAGAAATTTGATAGGCCTTTACAGGGCTAAGGCCCATTATTATTTGG<br>GTAAGAATTGAAGCCCTAAGGCAAGGGTTAAAACACAACCACCTAGGGTTTCTCTCTCCCTATAAACTATATAAACT<br>TGTTCATTTTGTTCGTTCCTCTCTTCTCTTGCAAACTC |
| >SEQ ID 30 (SP3bad90)<br>AACATAACTTGTATATGTAAAGATGAATGTAAACCTTCTTAGAGAGGACATATATAAATTGTGTTATCCATTACTTT<br>TAATAAGGAAATCCAAGCTTTTCAGGTCCAATTGAAAATAAGTTTATCAAAATTTATGAAAATTACAAATAAAAACC<br>AAAACAACCAAAGAATTATGTATATCTTATGGTGGAACGATTATTATTCACTCGTACATGATTCATAGCAAATTTTA<br>ATTGATTACAAAAAGTATAAATATAATATTAATAAAATAAACGCTTATGAAAAGATAAATTCTTCTTCAAGGCCAA<br>ATGAACCCTTATGAGTAACGTCTATTCTGCACTTAAAAAAAAAGAGAATTGAGTATTTTTTGAAGCCCATATGGCC<br>CCATTTTAAAATGTAATAAAGTAAGCCCAATAATGAGAATTATAAAGCTTAGTTTTCTTTCACTGCTTTATAAATCG<br>ACCTTTTGTTCGTTCCTTCCCTTCTCTTATCTTCATCT |
| >SEQ ID 31 (SP4bad90)<br>AAATTGTTGATAGAATTTCAAACATAATATAACTGAACATTAAATCTTAATTAATTATCAGAAATATGATCACTATA<br>ATCCGACTTTGTCTTTCGGATTTTATTAATTTTCAACTAAAAAATCTCAACAGATAAAACAAACCTACTCTGTCGAT<br>AATCCAATATTTTAATTTTATTGAGAAGCTCATATGACAACGTGTACAGATATCTACAAAATGTTTTCTACATATTT<br>CCAATTTTGTCACATGTCAATTTTAAGTGTCAAACACTAATAAAATAAACTAAATTAGATTATTTTCGTATTAATGA<br>GTAAAAAAATGGGCCTAAACAAATTGTATCACTAAAAAGTAATTTAGAAATTCATAAGTAGGCTATATGAGTTAGTT<br>TTTAAAGCTATAATTTTAAAGGTCCAAAACCCTTCCTAAGGTTTCGACAGAAACCTATAAGGAGACTCTATATAACT<br>CCTCCCTTCGTGCATTAGGGTATCTCATTCTCTGAAGA |
| >SEQ ID 32 (SP5bad90)<br>ACTGTTCGGTTGTCTGGGTTCTACATAAAGATTACCAAGTCCATTGATTGTATTGCGTGTTTTTTGTGGCGCACTT<br>ATACGTTGTATTTTGTAACGAAAAATGTTTCCAACTAATTTGAATTTTGTTTCCAAACAACTTCAAATAATCATTGG<br>TTTCTCAAGAGTCAACCAAGAATTAGAAATGGTATGATAGATTTCTCAATAAACAACAAAATTGTCAATTTTATCAG<br>TTTTGGTGAAGCTACAGCATCATTTGTGATCTGTCTTTCAAATTTTGCTTAAATAAATAAATCCTCAAATAGTTGGA<br>ATGAGTAAAAATGAAATAATTAGGCTTACATAGTATTTAAATAGGCTTCAATAAGGCTAAGGCCCAAATTTGTTAAA<br>TTAAGAATTGAGGTCCAAAAATCTATGTTAGAACACTGTAGGTCGGGGTTTCTACTCTCCTGTATATTCGATAAACT<br>CGGTCATTCCATTCGTCTAACTAATCTCTCGCAAACTC |
| >SEQ ID 33 (SP3bad80)<br>AACATCAAGCGTGCATTTAAACATAAAGATAAACCATCTTAGAGAGCACATATCTAAATTGTGTTAGTCATCACCTT<br>TAATTAGTATATATGATCTTTTCACTACCAATGGAGGATTACTTTAGCTCAATTTATGGGACTGGCATAGGATATCC<br>AAAACAATAACAGAACTGTGGCTATGCAAATGGGGAACGATTTTTATTCACTTGTGCATGATTTCTAGAAGGTTTTT<br>ATTTTGTATAAAAAGTATAAACATAATATTAATCAAATAAATGCTTTTGAAATACATAAATACTTCTGCAAGGGTAA<br>ATGCAACCTAATCTGTAACGTCTATTCTGCTTGTAAGAAAATAGAGATGTGATTATATTTTGGAAGCCCATATGGTG<br>ACATCTTAAAATATAATAAAGAAATCCGAATAATGCGAGTTAAACACCGTAGTTTTCTTCCCCTGTCATATAGATCG<br>ACATTTAGATCGTTCCTTCTCTTAGGCTGTCTTCCTCT |
| >SEQ ID 34 (SP4bad80)<br>AAATCGCTGTTATAATTTCAAACATAACAGACCATAAAATTAAATTTTACTTAATTCTCATATATACGATAACTATC<br>ATCCTATGTTGTGTTTTCGCTATTATTAATCTTCAACTAAATCATATAAATTGGCAAGGCAAACCCACTTTTTGAT<br>AATCCAATCTTTTAATTTTATTGAGAAGGTTATATGCTAAAGTATACCGTTATATACAAAATGCTTTCTCCATATTT<br>GAGATTGTGTTGGAAGTCCCACTTAGGTGTCGAACGCTAAAAAAATCAAATATCGTAACTCATACTTTGATTAATGA<br>GTACTACCATGGTCCTAAACAAATGATAACAATAAGAAGTAATTTAGAAATTCATAAGTGGCTCATCTAATTGAGTT<br>TTTTAAGCTACAATTATAAGGGGCCAACACCCTTCTTTGGCTTTATACAATAACCTCTAAGGAGGCTCTCTTTAAAC<br>CCTCTATTCGGTCATTAGGCTCTTGCCTTCTCTGAAGA |

SUMMARY OF SEQUENCES

>SEQ ID 35 (SP5bad80)
ACACTCGGATTATTTGAGTACTCCATTAGGATTGCCGTCTCCCTAGATTGAATTATGTGTGATTTTCTCGCCCACTT
GTACGTTGTCTTGTTCCACAAAAAATCTTTTTTATTAATTTGACTATCGTTTCTAAACAAATACACATAACGATTGG
ATCCCCTAGAGTCAATGAAGAATTACAAATGATATGGTAGATTTCTAAAGAAAAGACAAAATTGTCATTTTTTTCAG
TGTATGTATATCTTCAGAGCCATTTGTGTTAGGTCTAGCAAGTTCTGCTTAAATAAATAAATCCTCATATACTTAGA
GTGCCTAAAAAGTAAAGTATTAGTCTTAAATGGTCGTTAGACTAACCCCAAAAGGTCAAGGCTTAAATTTGTTATA
TCAAGTATTTAAGTCAAAAAAACCTATCTTTAAGGAATCAAGGTTAAGGTTGCTTAACTCCCATTTATCCTATAAACT
TGGTCATTCCATTCGTCAAATTCCGCTCTTGCAAATTC >SEQ ID 36 (SP3bad70)
AACCTAATTTGCGTATACAAATATAGCGATTCACCTTCTTAGAAACAACATACTTAGTAGGTGTCATAAAGTGCATG
TAATAAGGATGTATAATCTTTTTATTCTGAATTTTAGATAACACTATTAATATTAATGACAAATATAAACAGAATCA
TAGACACAACAAGCAAGGAGTAAATGGGATCGAGAAACGATTTTTCTTTACTCGTACGTCATCGATAGAAACTTAGA
ACGCCCTCTCAAACGTTTAAGTATAATACCAACCAGACAAATTCACATGAAGTTAAAAATACTTCTTTTGGGGTAA
ATGAAACCTAACGAGGAAAGCCTTTTCGCTACTTAAACATAAAGAGACATGAGCGTATATGGCTTCCCGTTAATCC
CCAATTTAAAATTTATCACACTTAGCCGGATTACGTGAGTATAAAATTCTCGCCTTCGTGCCCTCCTTTATAGATCG
AGACTTTTTTCTTTAGTTCTAGCTTCTTGACTATCCTT >SEQ ID 37 (SP4bad70)
CAATTGCTGAAAGAATTTCAGTCATAACATAACTCAACATGATTTCCTAATCCACTATTTAATATACGTGCCCCATC
CTCCAGGTTAGTCTCCTCGCCTTGAGTAATTTTTAAGTATAAAATCATGACAGATGAAAGAAATGCACTTTGGTGAG
GATCCAATATTGTAATATAATTTAGACATTGATATGAAAAAGGCTTCAAGTATTTACATAAGGACTCATGCATATAT
TGAATTTCGCTTAGCGTCAGTCTCGCAGCTGAAAGACTAATAAAATACAATACGATAAATAATACTTGGATTAATGA
GTACAAAAATACGCCTAGTCGACTGTGATTGGCAAAAATAATTTAGAAATCGCTAATCAACCAAGTTGACTCATTT
TTTTAGGCCTAAATTTCACAGTTCCTACCCTCTGATTACTGTTACAATAGAGTCCTATAGGAATTCTCTATCTAAAG
CTCGTGATCGTTACACAGGGTGTCACTTTCTGTGAAAA >SEQ ID 38 (SP5bad70)
AGGTCGGACCTATCTTGGGACGACATAGCCATTGCCAATAGGCACAATCGTATTCTGTGCGTTTTAATGGCTCCCTT
ATTGTTTGCCTTTTTTAAAAAGATATCTGTTCACCTAATTGCTATTATGTTCACGCACACTTTCCAAGAACGATAGG
TATCTCAAGAAACAGTCAATAAGTAGAACTACTATGATAGTCATCTTATTAAAAGACCAAATCTTGAATCTTTTCAG
TTTTTTTGAATCTATAGCATCTTTGGGGTTACGTCTTTCAACCATGGCTTAAATAAAAACTTGCGCAAAAACTTTGG
ATTGCTAAATATAAACTTATTATCGGTACATGGTGATTATAAAGGCTTCAAAAACGCAAAGCCCGTAGTTGGTTAAT
CTCAGAGTTGCGATTGAGAATAATATATTTAAACAGACTCGGTAGGCGTCACCTCTCTCCGATTGAATCAGTAAACT
AAATCAACCCTTTCTGGAAACCGCTCTCCTGCAAACGC >SEQ ID NO: 39 (TATA box)
TATAWAW, where W indicates T or A

What is claimed is:

1. A method for making a synthetic promoter for controlling transgene expression, the method comprising:
(a) accessing a database including:
(i) genomic data representative of multiple genes, wherein the multiple genes are genes from at least one plant, and wherein the genomic data include a gene sequence for each of the multiple genes, and
(ii) gene expression property data indicative of the presence of one or more gene expression property for ones of the multiple genes;
(b) selecting, by a processor, a first set of gene sequences from the multiple genes, based on the gene expression property data indicating the one or more gene expression property is present for each gene in the first set of gene sequences;
(c) extracting, by the processor, from each gene sequence in the first set of gene sequences, a promoter sequence A;
(d) selecting, by the processor, a second set of gene sequences from the multiple genes, based on the gene expression property data indicating the one or more gene expression property is absent for each gene in the second set of gene sequences;
(e) extracting, by the processor, from each gene sequence in the second set of gene sequences, a promoter sequence B;
(f) aligning, by the processor, the promoter sequences A and B based on a landmark into a sequence alignment, the landmark including one of a TATA box and a transcription start site (TSS);
(g) selecting, by the processor, a test promoter sequence S;
(h) calculating, by the processor, a score, using the sequence alignment, for the test promoter sequence S, based on a scoring function, as:

$$Z_1(S) = \sum_{i \in S} \log\left(\frac{\|A_{k,i}\|}{\|A_i\|} \cdot \frac{\|G_i\|}{\|G_{k,i}\|}\right);$$

wherein G is a union of the first and second sets of promoter sequences A and B, and for each position i relative to the landmark and each k-mer k, $G_{k,i}$ are sequences in G that contain k-mer k at position i;
(i) modifying, by the processor, the test promoter sequence S, at random, to form a modified test promoter sequence S';
(j) calculating, by the processor, a score for the modified test promoter sequence S', based on said scoring function; and
(k) in response to the calculated score for the modified test promoter sequence S' being improved over the calculated score for the test promoter sequence S, storing, by the processor, in a memory, the modified test promoter sequence S', thereby permitting synthesis of the modified test promoter sequence S'.

2. The method of claim 1, further comprising:
synthesizing the modified test promoter sequence S'; and
introducing the synthesized modified test promoter sequence S' in operable association with a coding sequence.

3. The method of claim 1, further comprising synthesizing the modified test promoter sequence S'; and
wherein the synthesized modified test promoter sequence S' includes a homology of less than about 30 percent relative to any of the promoter sequences A extracted from the first set.

4. The method of claim 1, wherein the k-mer k has a size of from 5 to 10 nucleotides.

5. The method of claim 1, further comprising calculating a sequence complexity of the modified test promoter sequence S', and constraining the sequence complexity of the modified test promoter sequence S' to an approximate sequence complexity of one or more of the promoter sequences A.

6. The method of claim 1, further comprising modifying said modified test promoter sequence S' to comprise one or more consensus sequences.

7. The method of claim 6, wherein said one or more consensus sequences are selected from a TATA sequence, a transcription factor binding site, a chromatin control sequence, a consensus sequence in a 5'-untranslated region, and a consensus sequence in 3' untranslated region.

8. The method of claim 1, wherein the k-mer k includes between 4 and 10 consecutive bases.

9. The method of claim 1, wherein the scoring function is expressed as:

$$\sum_{i \in S} \log\left(\frac{\|G_i\|}{\|A_i\|} \cdot \frac{\langle A_{k,i} \rangle + \frac{\|A_i\|}{\|G_i\|}\rho}{\langle G_{k,i} \rangle + \rho}\right),$$

wherein $\rho$ is a number of pseudo-counts.

10. The method of claim 1, wherein the scoring function is further expressed as:

$$Z_3(S) = \sum_{i \in S} \log \frac{P(E \mid k, i)}{P(E)} = \sum_{i \in S} \log\left(\frac{\|G_i\|}{\|A_i\|} \cdot \frac{\hat{A}_{k,i} + \frac{\|A_i\|}{\|G_i\|}\rho}{\hat{G}_{k,i} + \rho}\right),$$

wherein $\rho$ is a number of pseudo-counts.

11. The method of claim 1, wherein calculating the score includes calculating the score further based on:

$$Z(S) = Z_3(S) + \varepsilon_z Z_4(S) + \varphi_z Z_5(S),$$

wherein:

$$Z_3(S) = \sum_{i \in S} \log \frac{P(E \mid k, i)}{P(E)} = \sum_{i \in S} \log\left(\frac{\|G_i\|}{\|A_i\|} \cdot \frac{\hat{A}_{k,i} + \frac{\|A_i\|}{\|G_i\|}\rho}{\hat{G}_{k,i} + \rho}\right),$$

wherein $\rho$ is a number of pseudo-counts, wherein:

$$Z_4(S) = \frac{-1}{2\sigma_{H0}^2} \sum_{i \in S} (H_{S,i} - H_0)^2,$$

and
wherein:

$$Z_5(S) = \sum_{i \in S} \log\left(4^k \cdot \frac{\hat{A}_{k,i} + 4^{-k}\rho}{\|A_i\| + \rho}\right).$$

12. The method of claim 1, further comprising, for the synthesis of the modified test promoter sequence S':
providing a first oligonucleotide comprising at least a first portion of the modified test promoter sequence S' and a second oligonucleotide that is complementary to at least a second portion of the modified test promoter sequence, wherein the first oligonucleotide comprises a base pair sequence that is complementary with a sequence in the second oligonucleotide; and
generating a double stranded DNA sequence by polymerase chain reaction (PCR); and
wherein the double stranded DNA sequence comprises the modified test promoter sequence S'.

13. The method of claim 12, further comprising:
providing a third oligonucleotide comprising at least a third portion of the modified test promoter sequence S' and a fourth oligonucleotide comprising at least a fourth portion of the modified test promoter sequence S', wherein a 3'-terminus of the third oligonucleotide comprises a nucleotide sequence that overlaps with a sequence on a 5' terminus of the first oligonucleotide, and wherein the 3'-terminus of the fourth oligonucleotide comprises a nucleotide sequence that overlaps with a sequence on the 5' terminus of the second oligonucleotide; and
extending the double stranded DNA sequence by PCR; and
wherein the extended double stranded DNA sequence comprises the modified test promoter sequence S'.

14. The method of claim 1, further comprising repeating steps (i)-(k), wherein the modified test promoter sequence S' for a prior iteration of steps (i)-(k) is the test promoter sequence S in a next iteration of steps (i)-(k), until the modified promoter sequence S' includes a homology of less than a threshold percentage, relative to any of the promoter sequences A extracted from the first set.

\* \* \* \* \*